United States Patent
Suh et al.

(10) Patent No.: US 9,593,098 B2
(45) Date of Patent: Mar. 14, 2017

(54) COMPOUNDS AND COMPOSITIONS FOR MODULATING EGFR MUTANT KINASE ACTIVITIES

(71) Applicant: Yuhan Corporation, Seoul (KR)

(72) Inventors: Byung-Chul Suh, Lexington, MA (US); Paresh Devidas Salgaonkar, Medford, MA (US); Jaekyoo Lee, North Andover, MA (US); Jong Sung Koh, Gyeonggi-Do (KR); Ho-Juhn Song, Andover, MA (US); In Yong Lee, Belmont, MA (US); Jaesang Lee, Belmont, MA (US); Dong Sik Jung, Chungcheongnam-Do (KR); Jung-Ho Kim, Gyeonggi-Do (KR); Se-Won Kim, Gyeonggi-Do (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 14/881,930

(22) Filed: Oct. 13, 2015

(65) Prior Publication Data

US 2016/0102076 A1   Apr. 14, 2016

Related U.S. Application Data

(60) Provisional application No. 62/063,394, filed on Oct. 13, 2014.

(51) Int. Cl.
| | |
|---|---|
| *A61K 31/506* | (2006.01) |
| *C07D 403/04* | (2006.01) |
| *C07D 403/14* | (2006.01) |
| *C07D 409/14* | (2006.01) |
| *C07D 413/14* | (2006.01) |

(52) U.S. Cl.
CPC ......... *C07D 403/04* (2013.01); *C07D 403/14* (2013.01); *C07D 409/14* (2013.01); *C07D 413/14* (2013.01); *A61K 31/506* (2013.01)

(58) Field of Classification Search
CPC ........................... A61K 31/506; C07D 403/04
See application file for complete search history.

(56) References Cited

U.S. PATENT DOCUMENTS 8,673,925 B1 * 3/2014 Goldstein ............ A61K 31/519
514/262.1
2010/0029610 A1   2/2010 Singh et al.

FOREIGN PATENT DOCUMENTS

| CN | 104788427 A | * | 7/2015 | |
| CN | 104788427 (A) | | 7/2015 | |
| WO | WO-2011060295 A1 | | 5/2011 | |
| WO | WO-2013014448 A1 | | 1/2013 | |
| WO | WO 2014040555 A1 | * | 3/2014 | .......... C07D 403/12 |

OTHER PUBLICATIONS

Finlay, M. Raymond V., et al. "Discovery of a Potent and Selective EGFR Inhibitor (AZD9291) of Both Sensitizing and T790M Resistance Mutations That Spares the Wild Type Form of the Receptor." J. Med. Chem 57 (2014): 8249-8267.
International Search Report (ISR) in PCT/KR2015010784 issued Apr. 29, 2016.
Written Opinion of the International Searching Authority in PCT/KR2015010784 issued Apr. 29, 2016.

* cited by examiner

*Primary Examiner* — Alexander R Pagano
(74) *Attorney, Agent, or Firm* — Mintz Levin Cohn Ferris Glovsky and Popeo, P.C.; Kongsik Kim; Linyu L Mitra

(57) ABSTRACT

The present invention provides a new group of protein kinase inhibitors, aminopyrimidine derivatives, and pharmaceutically acceptable salts thereof that are useful for treating cell proliferative disease and disorder such as cancer and immune disease. The present invention provides methods for synthesizing and administering the protein kinase inhibitor compounds. The present invention also provides pharmaceutical formulations comprising at least one of the protein kinase inhibitor compounds together with a pharmaceutically acceptable carrier, diluent or excipient therefore. The invention also provides useful intermediates generated during the syntheses of the aminopyrimidine derivatives.

20 Claims, 1 Drawing Sheet

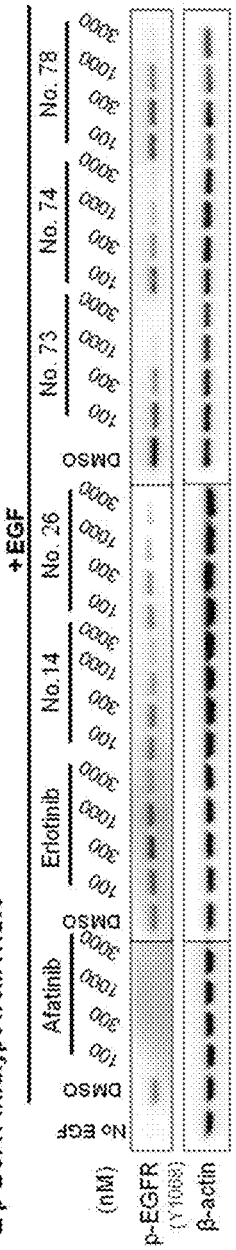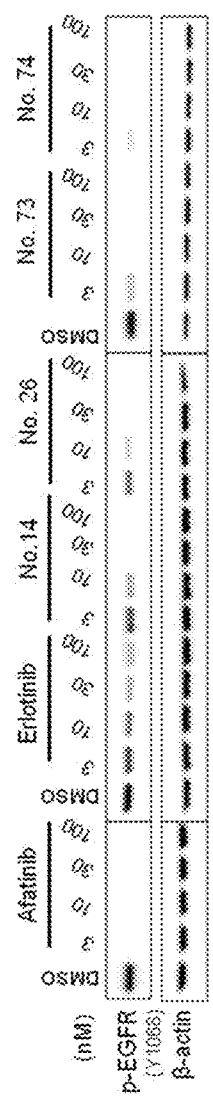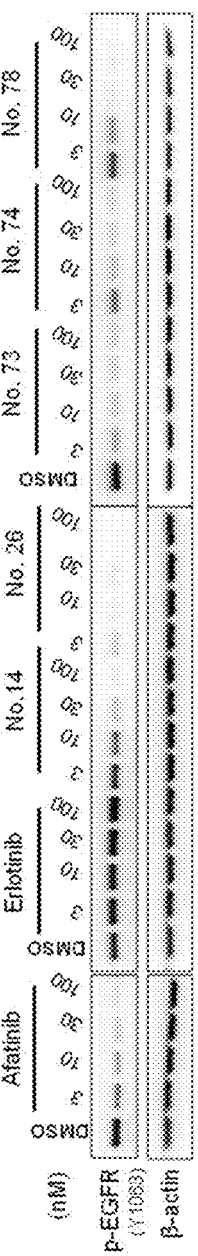

COMPOUNDS AND COMPOSITIONS FOR MODULATING EGFR MUTANT KINASE ACTIVITIES

CROSS REFERENCE TO RELATED APPLICATIONS

This application claims priority to U.S. provisional application No. 62/063,394 filed on Oct. 13, 2014, which is incorporated herein by reference.

TECHNICAL FIELD

The present invention relates to novel chemical compounds and pharmaceutically acceptable compositions thereof which display inhibition activity against certain mutated forms of EGFR.

BACKGROUND

Protein kinases catalyze the transfer of the terminal phosphate from ATP or GTP to the hydroxyl group of tyrosine, serine and/or threonine residues of proteins. Protein kinases are categorized into families by the substrates they phosphorylate, for example, protein tyrosine kinases (PTK), and protein serine/threonine kinases. Phosphorylation via protein kinase(s) results in a functional change of the target protein (substrate) by changing enzyme activity, cellular location or association with other proteins. Protein kinases play vital role in variety of cellular processes; cell proliferation, cell survival, metabolism, carbohydrate utilization, protein synthesis, angiogenesis, cell growth and immune response.

Misregulation of the protein kinases has been implicated in numerous diseases and disorders such as central nervous system disorders (e.g., Alzheimer's disease), inflammatory and autoimmune disorders (e.g., asthma, rheumatoid arthritis, Crohn's disease, and inflammatory bowel syndrome, and psoriasis), bone diseases (e.g., osteoporosis), metabolic disorders (e.g., diabetes), blood vessel proliferative disorders, ocular diseases, cardiovascular disease, cancer, restenosis, pain sensation, transplant rejection and infectious diseases.

Among them, overexpression and misregulation of EGFR is commonly found in breast, lung, pancreas, head and neck, as well as bladder tumors. EGFR is a transmembrane protein tyrosine kinase member of the erbB receptor family. Upon binding of a growth factor ligand such as epidermal growth factor (EGF), the receptor can dimerize with EGFR or with another family member such as erbB2 (HER2), erbB3 (HER3) and erbB4 (HER4). The dimerization of erbB receptors leads to the phosphorylation of key tyrosine residues in the intracellular domain and sequentially to stimulation of numerous intracellular signal transduction pathways involved in cell proliferation and survival. Misregulation of erbB family signaling promotes proliferation, invasion, metastasis, angiogenesis, and tumor survival and has been described in many human cancers such as lung and breast.

Therefore, the erbB family is a rational target for anticancer drug development and a number of compounds targeting EGFR or erbB2 are now clinically available, including gefitinib (IRESSA™) and erlotinib (TARCEVA™), the first generation inhibitor. It was reported that the most common EGFR activating mutations, L858R and del E746-A750 were sensitive to treatment of gefitinib or erlotinib but ultimately acquired resistance to therapy with gefitinib or erlotinib arises predominantly by mutation of the gatekeeper residue T790M, which is detected in approximately half of clinically resistant patients, resulting in double mutants, L858R/T790M and del E746-A750/T790M.

Biological and clinical importance of EGFR mutants has been recognized in the field and several second generation drugs such as BIBW2992 (Afatinib), HKI-272 and PF0299804 are in development and effective against the T790M resistance mutation but show concurrent strong inhibition of wildtype (WT) EGFR, which causes severe adverse effect. Therefore, a strong need still exists for compounds which potently inhibit EGFR single and double mutants as well as are selective over WT EGFR to provide an effective and safe clinical therapy for the diseases associated with or mediated by EGFR mutants.

Another example of misregulation of the protein kinases that has been implicated in numerous diseases and disorders is Janus kinase (JAK) 3. In contrast to the relatively ubiquitous expression of Janus family member, JAK1, JAK2 and Tyk2, JAK3 is predominantly expressed in hematopoietic lineage such as NK cells, T cells and B cells and intestinal epithelial cells. Targeting JAK3 could be a useful strategy to generate a novel class of immunosuppressant drugs. Due to primary expression in hematopoietic cells, so a highly selective JAK3 inhibitor should have precise effects on immune cells and minimal pleiotropic defects. The selectivity of a JAK3 inhibitor would also have advantages over the current widely used immunosuppressant drugs, which have abundant targets and diverse side effects. A JAK3 inhibitor could be useful for treating autoimmune diseases, and JAK3 mediated leukemia and lymphoma.

For example, somatic mutations of JAK3 were also identified in a minority of acute megakaryoblastic leukaemia (AMKL) patients both in Down syndrome children and non-Down syndrome adults, and in a patient with acute lymphoblastic leukaemia. In addition, JAK3 activation was identified in several lymphoproliferative disorders, including mantle cell lymphoma, Burkitt's lymphoma, human T-cell leukemia/lymphoma, virus-1-induced adult T-cell lymphoma/leukemia and anaplastic large cell lymphoma. It was shown that constitutive activation of the JAK3/STAT pathway has a major role in leukemia and lymphoma cell growth and survival and in the invasive phenotype. Therefore, the constitutive activation of JAK3, which can result from JAK3-activating mutations, is a frequent feature of several leukemia and lymphoma so that selective inhibition of JAK3 could be therapeutic target.

Therefore, a strong need exists for compounds which selectively and potently inhibit JAK3 wildtype and mutants as well as are selective over other JAK family members to provide an effective and safe clinical therapy for the diseases associated with or mediated by JAK3.

A need also exists for methods of administering such compounds, pharmaceutical formulations and medicaments to patients or subjects in need thereof.

SUMMARY

The present invention relates to novel chemical compounds and pharmaceutically acceptable compositions thereof which display inhibition activity against certain mutated forms of EGFR.

The invention provides pyrimidine derivatives represented by Formula (I) and their use for the treatment or prevention of a number of different cancers associated with one or more EGFR mutations.

Such compounds have general Formula (I) as well as pharmaceutically acceptable salts, diastereomers, enantiomers, racemates, hydrates or solvates thereof,

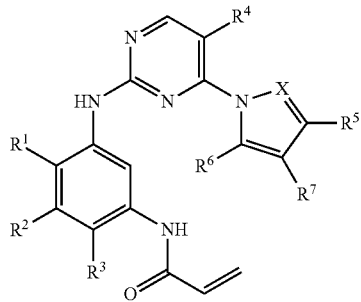

I wherein:

X is CH or N;

$R^1$ is H, $R^8$ or —$OR^8$;

$R^2$ is hydrogen, $C_{1-6}$ alkyl, 6-10 membered monocyclic or bicyclic aryl, or 5-10 membered heteroaryl comprising 1-4 heteroatoms selected from N, O, and S, wherein the aryl or heteroaryl is optionally and independently substituted at one or more carbon atoms with $R^{13}$; and wherein the heteroaryl having one or more nitrogen atoms is optionally and independently substituted at one or more nitrogen atoms with $R^8$;

$R^3$ is hydrogen, 4-7 membered monocyclic heterocyclyl comprising 1-2 heteroatoms selected from N, O and S, and optionally substituted with oxo, 5-6 membered heteroaryl comprising 1-3 heteroatoms selected from N, O and S, $NR^9R^{10}$, $NR^{11}R^{12}$, or phenyl, wherein the heteroaryl or phenyl is optionally and independently substituted at one or more carbon atoms with $R^{13}$; and wherein the heterocyclyl or heteroaryl having one or more nitrogen atoms is optionally and independently substituted at one or more nitrogen atoms with $R^8$;

$R^4$ is hydrogen, $C_{1-4}$ alkyl, $C_{3-5}$ cycloalkyl, F, Cl, Br, CN, or $CF_3$;

$R^5$ is hydrogen, $CF_3$, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with $R^{13}$;

$R^6$ is hydrogen or $C_{1-6}$ alkyl;

$R^7$ is hydrogen, —$CH_2OH$, —$CH_2OR^8$, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;

$R^8$ is selected from $C_{1-6}$ alkyl or $C_{3-7}$ cycloalkyl;

$R^9$ is selected from $C_{1-6}$ alkyl, $C_{3-7}$ cycloalkyl or 4-7 membered heterocyclyl comprising 1-2 heteroatoms selected from N, O and S, wherein the $C_{1-6}$ alkyl or $C_{3-7}$ cycloalkyl is optionally substituted with halogen or —$OR^8$, and wherein the 4-7 membered heterocyclyl having one nitrogen atom is optionally and independently substituted with —$R^8$, —$C(O)R^8$, —$C(O)OR^8$, or $C(O)NHR^8$;

$R^{10}$ is $C_{1-6}$ alkyl, $C_{3-7}$ cycloalkyl, or $(CH_2)_nNR^9R^9$, wherein each n is independently 1 or 2;

$R^{11}$ and $R^{12}$, taken together with nitrogen atom to which they are bonded form, independently for each occurrence, i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbons (e.g., at one, two, or three carbon atoms) with halogen, hydroxyl, —$OR^8$, —$NR^9R^{10}$, or —$NR^{11}R^{12}$; or ii) a 5-8 membered saturated or partially saturated monocyclic group having 1 or 2 heteroatoms, in addition to the nitrogen atom to which $R^{11}$ and $R^{12}$ are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms (e.g., at one, two, or three carbon or nitrogen atoms) with —$R^8$, —$C(O)R^8$, —$C(O)OR^8$, —$C(O)NHR^8$, —$SO_2R^8$, —$SO_2NH_2$, or —$SO_2NR^8{}_2$; and $R^{13}$ is selected from halogen, CN, $CF_3$, $R^8$, —$OR^8$ or $C_{2-4}$ alkenyl;

or a pharmaceutically acceptable salt thereof.

The present invention also relates to compositions comprising these compounds, methods of making these compounds, methods of inhibiting enzyme activity, particularly one or more EGFR mutant and JAK3 kinase activity, through use of these compounds, and a method of treating disease or disease symptoms in a mammal, particularly where inhibition of the kinase activity, can affect disease outcome.

BRIEF DESCRIPTION OF THE DRAWINGS

FIG. 1 shows visualization of Western blots showing the results of inhibition of phosphorylation level of mutant EGFR as compared to wildtype EGFR.

DETAILED DESCRIPTION

The present invention provides a group of aminopyrimidine derivatives and pharmaceutically acceptable salts thereof that are useful for inhibiting one or more protein kinases and for treating diseases and disorders that are mediated by the protein kinase, for example, cell proliferative disease and disorder such as cancer, autoimmune diseases, infection, cardiovascular disease, and neurodegenerative disease and disorder. The present invention also provides methods for synthesizing and administering the aminopyrimidine derivatives. The present invention also provides pharmaceutical formulations comprising at least one of the compounds of Formula (I) together with a pharmaceutically acceptable carrier, diluent or excipient therefor. The invention also provides useful intermediates generated during syntheses of the aminopyrimidine derivative compounds.

The present invention provides compositions and methods for modulating the activity of the epidermal growth factor receptor (EGFR) mutants and/or Janus kinase 3 (JAK3). In one aspect, the invention provides compounds which act as inhibitors of EGFR mutants or JAK3.

In a first embodiment, provided herein is a compound of Formula (I), individual stereoisomer, or mixture of isomers.

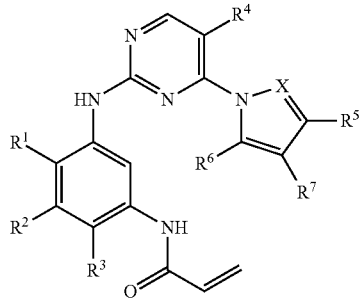

I wherein:

X is CH or N;

$R^1$ is H, $R^8$ or —$OR^8$;

$R^2$ is hydrogen, $C_{1-6}$ alkyl, 6-10 membered monocyclic or bicyclic aryl, or 5-10 membered heteroaryl comprising 1-4 heteroatoms selected from N, O, and S, wherein the aryl or heteroaryl is optionally and independently substituted at one or more carbon atoms with $R^{13}$; and wherein the heteroaryl having one or more nitrogen atoms is optionally and independently substituted at one or more nitrogen atoms with $R^8$;

$R^3$ is hydrogen, 4-7 membered monocyclic heterocyclyl comprising 1-2 heteroatoms selected from N, O and S, and optionally substituted with oxo, 5-6 membered heteroaryl comprising 1-3 heteroatoms selected from N, O and S, $NR^9R^{10}$, $NR^{11}R^{12}$, or phenyl, wherein the heteroaryl or phenyl is optionally and independently substituted at one or more carbon atoms with $R^{13}$; and wherein the heterocyclyl or heteroaryl having one or more nitrogen atoms is optionally and independently substituted at one or more nitrogen atoms with $R^8$;

$R^4$ is hydrogen, $C_{1-4}$ alkyl, $C_{3-5}$ cycloalkyl, F, Cl, Br, CN, or $CF_3$;

$R^5$ is hydrogen, $CF_3$, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with $R^{13}$;

$R^6$ is hydrogen or $C_{1-6}$ alkyl;

$R^7$ is hydrogen, —$CH_2OH$, —$CH_2OR^8$, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;

$R^8$ is selected from $C_{1-6}$ alkyl or $C_{3-7}$ cycloalkyl;

$R^9$ is selected from $C_{1-6}$ alkyl, $C_{3-7}$ cycloalkyl or 4-7 membered heterocyclyl comprising 1-2 heteroatoms selected from N, O and S, wherein the $C_{1-6}$ alkyl or $C_{3-7}$ cycloalkyl is optionally substituted with halogen or —$OR^8$, and wherein the 4-7 membered heterocyclyl having one nitrogen atom is optionally and independently substituted with —$R^8$, —$C(O)R^8$, —$C(O)OR^8$, or $C(O)NHR^8$;

$R^{10}$ is $C_{1-6}$ alkyl, $C_{3-7}$ cycloalkyl, or $(CH_2)_nNR^9R^9$, wherein each n is independently 1 or 2;

$R^{11}$ and $R^{12}$, taken together with nitrogen atom to which they are bonded form, independently for each occurrence, i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbons (e.g., at one, two, or three carbon atoms) with halogen, hydroxyl, —$OR^8$, —$NR^9R^{10}$, or —$NR^{11}R^{12}$; or ii) a 5-8 membered saturated or partially saturated monocyclic group having 1 or 2 heteroatoms, in addition to the nitrogen atom to which $R^{11}$ and $R^{12}$ are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms (e.g., at one, two, or three carbon or nitrogen atoms) with —$R^8$, —$C(O)R^8$, —$C(O)OR^8$, —$C(O)NHR^8$, —$SO_2R^8$, —$SO_2NH_2$, or —$SO_2NR^8{}_2$; and $R^{13}$ is selected from halogen, CN, $CF_3$, $R^8$, —$OR^8$ or $C_{2-4}$ alkenyl;

or a pharmaceutically acceptable salt thereof.

In a second embodiment, provided herein is a compound of Formula (II) or pharmaceutically acceptable salt thereof;

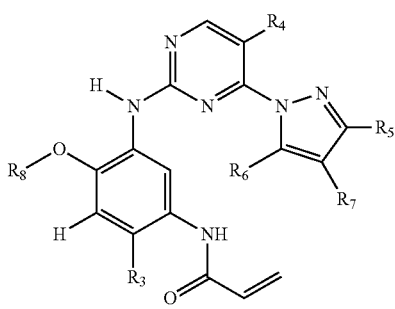

II wherein:

$R^3$ is hydrogen, 4-7 membered monocyclic heterocyclyl comprising 1-2 heteroatoms selected from N, O and S, and optionally substituted with oxo, 5-6 membered heteroaryl comprising 1-3 heteroatoms selected from N, O and S, $NR^9R^{10}$, $NR^{11}R^{12}$, or phenyl, wherein the heteroaryl or phenyl is optionally and independently substituted at one or more carbon atoms with $R^{13}$; and wherein the heterocyclyl or heteroaryl having one or more nitrogen atoms is optionally and independently substituted at one or more nitrogen atoms with $R^8$;

$R^4$ is hydrogen, $C_{1-4}$ alkyl, $C_{3-5}$ cycloalkyl, F, Cl, Br, CN, or $CF_3$;

$R^5$ is hydrogen, $CF_3$, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with $R^{13}$;

$R^6$ is hydrogen or $C_{1-6}$ alkyl;

$R^7$ is hydrogen, —$CH_2OH$, —$CH_2OR^8$, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;

$R^8$ is selected from $C_{1-6}$ alkyl or $C_{3-7}$ cycloalkyl;

$R^9$ is selected from $C_{1-6}$ alkyl, $C_{3-7}$ cycloalkyl or 4-7 membered heterocyclyl comprising 1-2 heteroatoms selected from N, O and S, wherein the $C_{1-6}$ alkyl or $C_{3-7}$ cycloalkyl is optionally substituted with halogen or —$OR^8$, and wherein 4-7 membered heterocyclyl having one nitrogen atom is optionally and independently substituted with —$R^8$, —$C(O)R^8$, —$C(O)OR^8$, or $C(O)NHR^8$;

$R^{10}$ is $C_{1-6}$ alkyl, $C_{3-7}$ cycloalkyl, or $(CH_2)_nNR^9R^9$, wherein each n is independently 1 or 2;

$R^{11}$ and $R^{12}$, taken together with nitrogen atom to which they are bonded form, independently for each occurrence, i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbons (e.g., at one, two, or three carbon atoms) with halogen, hydroxyl, —OR$^8$, —NR$^9$R$^{10}$, or —NR$^{11}$R$^{12}$; or ii) a 5-8 membered saturated or partially saturated monocyclic group having 1 or 2 heteroatoms, in addition to the nitrogen atom to which R$^{11}$ and R$^{12}$ are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms (e.g., at one, two, or three carbon or nitrogen atoms) with —R$^8$, —C(O)R$^8$, —C(O)OR$^8$, —C(O)NHR$^8$, —SO$_2$R$^8$, —SO$_2$NH$_2$, or —SO$_2$NR$^8{}_2$; and R$^{13}$ is selected from halogen, CN, CF$_3$, R$^8$, —OR$^8$ or C$_{2-4}$ alkenyl.

In a third embodiment, provided herein is a compound of Formula (III) or pharmaceutically acceptable salt thereof:

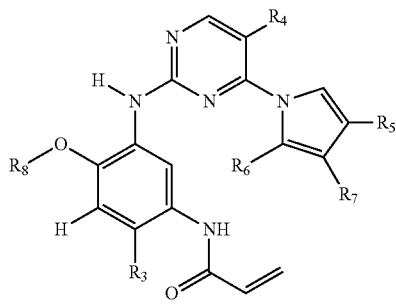

III wherein:
R$^3$ is hydrogen, 4-7 membered monocyclic heterocyclyl comprising 1-2 heteroatoms selected from N, O and S, and optionally substituted with oxo, 5-6 membered heteroaryl comprising 1-3 heteroatoms selected from N, O and S, NR$^9$R$^{10}$, NR$^{11}$R$^{12}$, or phenyl, wherein the heteroaryl or phenyl is optionally and independently substituted at one or more carbon atoms with R$^{13}$; and wherein the heterocyclyl or heteroaryl having one or more nitrogen atoms is optionally and independently substituted at one or more nitrogen atoms with R$^8$;

R$^4$ is hydrogen, C$_{1-4}$ alkyl, C$_{3-5}$ cycloalkyl, F, Cl, Br, CN, or CF$_3$;

R$^5$ is hydrogen, CF$_3$, C$_{1-6}$ alkyl, C$_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with R$^{13}$;

R$^6$ is hydrogen or C$_{1-6}$ alkyl;

R$^7$ is hydrogen, —CH$_2$OH, —CH$_2$OR$^8$, C$_{1-3}$ alkyl, (CH$_2$)$_n$NR$^9$R$^{10}$, (CH$_2$)$_n$NR$^{11}$R$^{12}$, C(O)NR$^9$R$^{10}$, or C(O)NR$^{11}$R$^{12}$, wherein each n is independently 1 or 2;

R$^8$ is selected from C$_{1-6}$ alkyl or C$_{3-7}$ cycloalkyl;

R$^9$ is selected from C$_{1-6}$ alkyl, C$_{3-7}$ cycloalkyl or 4-7 membered heterocyclyl comprising 1-2 heteroatoms selected from N, O and S, wherein the C$_{1-6}$ alkyl or C$_{3-7}$ cycloalkyl is optionally substituted with halogen or —OR$^8$, and wherein 4-7 membered heterocyclyl having one nitrogen atom is optionally and independently substituted with —R$^8$, —C(O)R$^8$, —C(O)OR$^8$, or C(O)NHR$^8$;

R$^{10}$ is C$_{1-6}$ alkyl, C$_{3-7}$ cycloalkyl, or (CH$_2$)$_n$NR$^9$R$^9$, wherein each n is independently 1 or 2;

R$^{11}$ and R$^{12}$, taken together with nitrogen atom to which they are bonded form, independently for each occurrence, i) a 3-8 membered saturated or partially saturated monocyclic group having no heteroatom other than the nitrogen atom to which R$^{11}$ and R$^{12}$ are bonded, wherein said 3-8 membered saturated or partially saturated monocyclic group is optionally and independently substituted at one or more carbons (e.g., at one, two, or three carbon atoms) with halogen, hydroxyl, —OR$^8$, —NR$^9$R$^{10}$, or —NR$^{11}$R$^{12}$; or ii) a 5-8 membered saturated or partially saturated monocyclic group having 1 or 2 heteroatoms, in addition to the nitrogen atom to which R$^{11}$ and R$^{12}$ are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms (e.g., at one, two, or three carbon or nitrogen atoms) with —R$^8$, —C(O)R$^8$, —C(O)OR$^8$, —C(O)NHR$^8$, —SO$_2$R$^8$, —SO$_2$NH$_2$, or —SO$_2$NR$^8{}_2$; and R$^{13}$ is selected from halogen, CN, CF$_3$, R$^8$, —OR$^8$ or C$_{2-4}$ alkenyl.

In certain embodiments of the compounds of Formula (I), (II), or (III), R$^1$ is —OCH$_3$; R$^4$ is H, —CH$_3$, F, or Cl; R$^5$ is hydrogen, C$_{1-6}$ alkyl, C$_{3-7}$ cycloalkyl, pyridinyl, thiophenyl, furanyl, N-methyl pyrrolidinyl, N-methyl pyrazolyl, or phenyl; R$^8$ is methyl; and n is 1.

In certain further embodiments, R$^2$ is H; R$^6$ is H; R$^3$ is morpholino, N-methyl piperazinyl, piperidinyl, azetidinyl, pyrrodinyl, 4-acetylpiperidinyl, N,N-dimethylamino, 1,4-oxazepan-4-yl, or 4-methyl-1,4,-diazepan-1-yl; and R$^7$ is —(CH$_2$)NR$^9$R$^{10}$ or —(CH$_2$)NR$^{11}$R$^{12}$.

In further embodiments, R$^9$ is methyl, ethyl, propyl, cyclopropylmethyl, or cyclobutylmethyl; and R$^{10}$ is methyl, ethyl, propyl, cyclopropylmethyl, oxetanyl, oxethanemethyl, N-methyazetinyl, N,N-dimethylethyl, or methoxyethyl; and NR$^{11}$R$^{12}$ is azetidinyl, 3-hydroxy azetidinyl, 3-methoxy azetidinyl, pyrrolidinyl, (S)-3-hydroxy pyrrolidinyl, (R)-3-hydroxy pyrrolidinyl, (3R,4S)-3,4-dihydroxypyrrolidinyl, (3S,4R)-3-hydroxy-4-methoxypyrrolidinyl, piperidinyl, morpholinyl, N-methylpiperazinyl, azamorpholinyl, N-methylazapiperazinyl, N-acetyl piperazinyl, or thiomorpholinyl.

In certain further embodiments, R$^5$ is hydrogen, methyl, isopropyl, t-butyl, cyclopropyl, 2-thiophenyl, 2-furanyl, 3-furanyl, 3-pyridyl, 4-pyridyl or phenyl.

In certain embodiments of the compound of Formula (I), (II), or (III), R$^7$ is —(CH$_2$)NR$^9$R$^{10}$ or —(CH$_2$)NR$^{11}$R$^{12}$.

In certain further embodiments, R$^9$ is methyl, ethyl, propyl, cyclopropylmethyl, or cyclobutylmethyl; and R$^{10}$ is methyl, ethyl, propyl, cyclopropylmethyl, oxetanyl, oxethanemethyl, N-methyazetinyl, N,N-dimethylethyl, or methoxyethyl; and NR$^{11}$R$^{12}$ is azetidinyl, 3-hydroxy azetidinyl, 3-methoxy azetidinyl, pyrrolidinyl, (S)-3-hydroxy pyrrolidinyl, (R)-3-hydroxy pyrrolidinyl, (3R,4S)-3,4-dihydroxypyrrolidinyl, (3S,4R)-3-hydroxy-4-methoxypyrrolidinyl, piperidinyl morpholinyl, N-methylpiperazinyl, azamorpholinyl, N-methylazapiperazinyl, N-acetyl piperazinyl, or thiomorpholinyl.

In a fourth embodiment, provided herein is a compound of Formula (IV) or a pharmaceutically acceptable salt thereof:

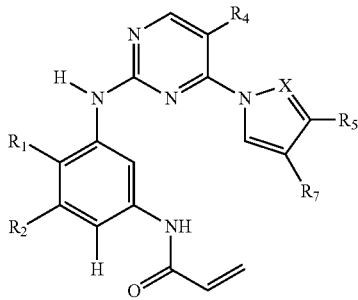

wherein:

X is CH or N;

$R^1$ is H, $R^8$ or —$OR^8$;

$R^2$ is hydrogen; $C_{1-6}$ alkyl; 6-10 membered monocyclic or bicyclic aryl; or 5-10 membered heteroaryl comprising 1-4 heteroatoms selected from N, O, and S, wherein the aryl or heteroaryl is optionally and independently substituted at one or more carbon atoms with $R^{13}$, and wherein the heteroaryl having one or more nitrogen atoms is optionally and independently substituted at one or more nitrogen atoms with $R^8$;

$R^4$ is hydrogen, $C_{1-4}$ alkyl, $C_{3-5}$ cycloalkyl, F, Cl, Br, CN, or $CF_3$;

$R^5$ is hydrogen, $CF_3$, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein heteroaryl or aryl is optionally and independently substituted at one or more carbon atoms with $R^{13}$;

$R^7$ is hydrogen, —$CH_2OH$, —$CH_2OR^8$, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;

$R^8$ is selected from $C_{1-6}$ alkyl or $C_{3-7}$ cycloalkyl;

$R^9$ is selected from $C_{1-6}$ alkyl, $C_{3-7}$ cycloalkyl or 4-7 membered heterocyclyl comprising 1-2 heteroatoms selected from N, O and S, wherein the $C_{1-6}$ alkyl or $C_{3-7}$ cycloalkyl is optionally substituted with halogen or —$OR^8$, and wherein the 4-7 membered heterocyclyl having one nitrogen atom is optionally and independently substituted with —$R^8$, —$C(O)R^8$, —$C(O)OR^8$, or $C(O)NHR^8$;

$R^{10}$ is $C_{1-6}$ alkyl, $C_{3-7}$ cycloalkyl, or $(CH_2)_nNR^9R^9$, wherein each n is independently 1 or 2;

$R^{11}$ and $R^{12}$, taken together with nitrogen atom to which they are bonded form, independently for each occurrence, i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbons (e.g., at one, two, or three carbon atoms) with halogen, hydroxyl, —$OR^8$, —$NR^9R^{10}$, or —$NR^{11}R^{12}$; or ii) a 5-8 membered saturated or partially saturated monocyclic group having 1 or 2 heteroatoms, in addition to the nitrogen atom to which $R^{11}$ and $R^{12}$ are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted with —$R^8$, —$C(O)R^8$, —$C(O)OR^8$, —$C(O)NHR^8$, —$SO_2R^8$, —$SO_2NH_2$, or —$SO_2NR^8{}_2$; and $R^{13}$ is selected from halogen, CN, $CF_3$, $R^8$, —$OR^8$ or $C_{2-4}$ alkenyl.

In certain embodiments of the compound of Formula (IV), $R^1$ is H; $R^2$ is furanyl, thiophenyl, N-methyl pyrazolyl, or phenyl; $R^4$ is H, —$CH_3$, F, or Cl; $R^5$ is hydrogen, $C_{1-6}$ alkyl, $C_{3-7}$ cycloalkyl, pyridinyl, thiophenyl, furanyl, N-methyl pyrrolyl, N-methyl pyrazolyl, or phenyl; and n is 1.

In certain further embodiments, $R^5$ is hydrogen, methyl, isopropyl, t-butyl, cyclopropyl, 2-thiophenyl, 2-furanyl, 3-furanyl, 3-pyridyl, 4-pyridyl or phenyl.

In certain further embodiments, $R^7$ is —$(CH_2)NR^9R^{10}$ or —$(CH_2)NR^{11}R^{12}$.

In still further embodiments, $R^9$ is methyl, ethyl, propyl, cyclopropylmethyl, or cyclobutylmethyl; and $R^{10}$ is methyl, ethyl, propyl, cyclopropylmethyl, oxetanyl, oxethanemethyl, N-methyazetinyl, N,N-dimethylethyl, or methoxyethyl; and $NR^{11}R^{12}$ is azetidinyl, 3-hydroxy azetidinyl, 3-methoxy azetidinyl, pyrrolidinyl, (S)-3-hydroxy pyrrolidinyl, (R)-3-hydroxy pyrrolidinyl, (3R,4S)-3,4-dihydroxypyrrolidinyl, (3S,4R)-3-hydroxy-4-methoxypyrrolidinyl, piperidinyl morpholinyl, N-methylpiperazinyl, azamorpholinyl, N-methylazapiperazinyl, N-acetyl piperazinyl, or thiomorpholinyl.

In certain embodiments of the compound of Formula (IV), $R^5$ is hydrogen, methyl, isopropyl, t-butyl, cyclopropyl, 2-thiophenyl, 2-furanyl, 3-furanyl, 3-pyridyl, 4-pyridyl or phenyl.

In a fifth embodiment, provided herein is a compound of Formula (I), Formula (II), or Formula (III), or a pharmaceutically acceptable salt thereof, wherein $R^1$ is —$OCH_3$; and n is 1.

In a sixth embodiment, provided herein is a compound of Formula (IV), or a pharmaceutically acceptable salt thereof, wherein $R^1$ is H; and n is 1.

In certain embodiments, the compound is a compound described herein or a pharmaceutically acceptable salt thereof.

In another aspect, the invention provides a method of treating protein kinase-mediated disease in a subject in need thereof, comprising administering to said subject a therapeutically effective amount of a compound of the invention (such as a compound of Formula (I)) or a pharmaceutically acceptable salt thereof, that is effective in treating abnormal cell growth and immune disease.

In another aspect, the invention provides a method of inhibiting at least one mutant of EGFR selectively as compared to wild type EGFR, in biological sample or in a patient, comprising contacting the biological sample with or administering to the patient a compound according of the invention, or a composition thereof (e.g., a pharmaceutical composition comprising the compound of the invention and a pharmaceutically acceptable carrier). In certain embodiments, the at least one mutant is Del E746-A750, L858R or T790M. In certain embodiments, the at least one mutant is at least one double mutant selected from Del E746-A750/T790M or L858R/T790M.

In another aspect, the invention provides a method of inhibiting Janus kinase 3 (JAK3) selectively as compared to other kinases, in biological sample or in a patient, comprising contacting the biological sample with or administering to the patient a compound of the invention, or a composition thereof, that is effective in treating abnormal cell growth including leukemia and lymphoma (B-cell & T-cell) and immune diseases including arthritis, rheumatoid arthritis and autoimmune diseases.

In another aspect, the invention provides a use of a compound of the invention (such as a compound of Formula (I)) or a pharmaceutically acceptable salt thereof for the manufacture of a medicament for treating protein kinase-mediated disease. Further, the invention provides a use of a compound of the invention or a pharmaceutically acceptable salt thereof for the manufacture of a medicament for inhibiting at least one mutant of EGFR selectively as compared to wild type EGFR.

In another aspect, the invention provides a pharmaceutical composition for treating protein kinase-mediated disease, comprising a compound of the invention (such as a compound of Formula (I)) or a pharmaceutically acceptable salt thereof as active ingredients. Further, the invention provides a pharmaceutical composition for inhibiting at least one mutant of EGFR selectively as compared to wild type EGFR, comprising a compound of the invention or a pharmaceutically acceptable salt thereof as active ingredients.

The term "alkyl," used alone or as part of a larger moiety such as "arylalkyl" or "cycloalkyl" refers to a straight or branched hydrocarbon radical having from 1 to 15 carbon atoms or from 1-8 carbon atoms (unless stated otherwise) and includes, for example, methyl, ethyl, n-propyl, iso-propyl, n-butyl, sec-butyl, iso-butyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, and oxygen.

The term "heterocycloalkyl" means a non-aromatic monocyclic or polycyclic ring comprising carbon and hydrogen atoms and at least one heteroatom, preferably, 1 to 4 heteroatoms selected from nitrogen, sulfur, oxygen, sulfone, or sulfoxide. A heterocycloalkyl group can have one or more carbon-carbon double bonds or carbon-heteroatom double bonds in the ring group as long as the ring group is not rendered aromatic by their presence.

Examples of heterocycloalkyl groups include azetidinyl, aziridinyl, pyrrolidinyl, piperidinyl, piperazinyl, homopiperazinyl, morpholino, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halogen" includes fluoro, chloro, bromo, and iodo.

As used herein, the term "alkoxy" refers to the alkyl groups above bound through oxygen, examples of which include methoxy, ethoxy, iso-propoxy, tert-butoxy, and the like. In addition, alkoxy also refers to polyethers such as —O—$(CH_2)_2$—O—$CH_3$, and the like. An alkoxy can be unsubstituted or substituted with one or more suitable substituents.

As used herein, the term "aryl" refers to unsubstituted or substituted aromatic monocyclic or polycyclic groups and includes, for example, phenyl and naphthyl. The term "aryl" also includes a phenyl ring fused to a non-aromatic carbocyclic or heterocyclic ring. The term "aryl" may be interchangeably used with "aryl ring," aromatic group," and "aromatic ring." Heteroaryl groups have 4 to 14 atoms, 1 to 9 of which are independently selected from the group consisting of oxygen, sulfur and nitrogen. Heteroaryl groups have 1-3 heteroatoms in a 5-8 membered aromatic group. An aryl or heteroaryl can be a mono- or bicyclic aromatic group. Typical aryl and heteroaryl groups include, for example, phenyl, quinolinyl, indazoyl, indolyl, dihydrobenzodioxynyl, 3-chlorophenyl, 2,6-dibromophenyl, pyridyl, pyrimidinyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like. An aryl or heteroaryl can be unsubstituted or substituted with one or more suitable substituents.

As used herein, the term "haloalkyl" refers to any alkyl radical having one or more hydrogen atoms replaced by a halogen atom. Examples of haloalkyl include —$CF_3$, —$CHF_2$, —$CH_2F$, and the like.

As used herein, the term "hydroxyl" or "hydroxy" refers to —OH.

As used herein, the term "amino" refers to —$NH_2$.

As used herein, the term "hydroxyalkyl" refers to any hydroxyl derivative of alkyl radical. The term "hydroxyalkyl" includes any alkyl radical having one or more hydrogen atoms replaced by a hydroxy group.

A "substituent" as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halogen, alkyl, haloalkyl, aryl, hydroxy, alkoxy, hydroxyalkyl, amino, and the like.

In certain aspects, the invention also provides (i) a method of preparing a compound of formula (c) by reacting a compound of formula (a) with a compound of formula (b) in the presence of the first base in the first organic solvent (see Scheme 1); (ii) a method of preparing a compound of formula (e) by reacting the compound of formula (c) with heteroaryl intermediates (d) in the presence of the second base, in the second organic solvent (see Scheme 1); (iii) a method of preparing a compound of formula (f) by reductive amination of the compound of formula (e) and an amine derivatives by using a reducing agent in the third solvent (see Scheme 1); (iv) a method of preparing a compound of Formula (I) by reduction of the compound of formula (f) by using a reducing agent in the fourth solvent and followed by amide formation in the presence of acryloyl chloride, the third base in the fifth solvent (see Scheme 1). The invention also provides a method of preparing a compound of Formula (I) according to Scheme 1.

Scheme 1

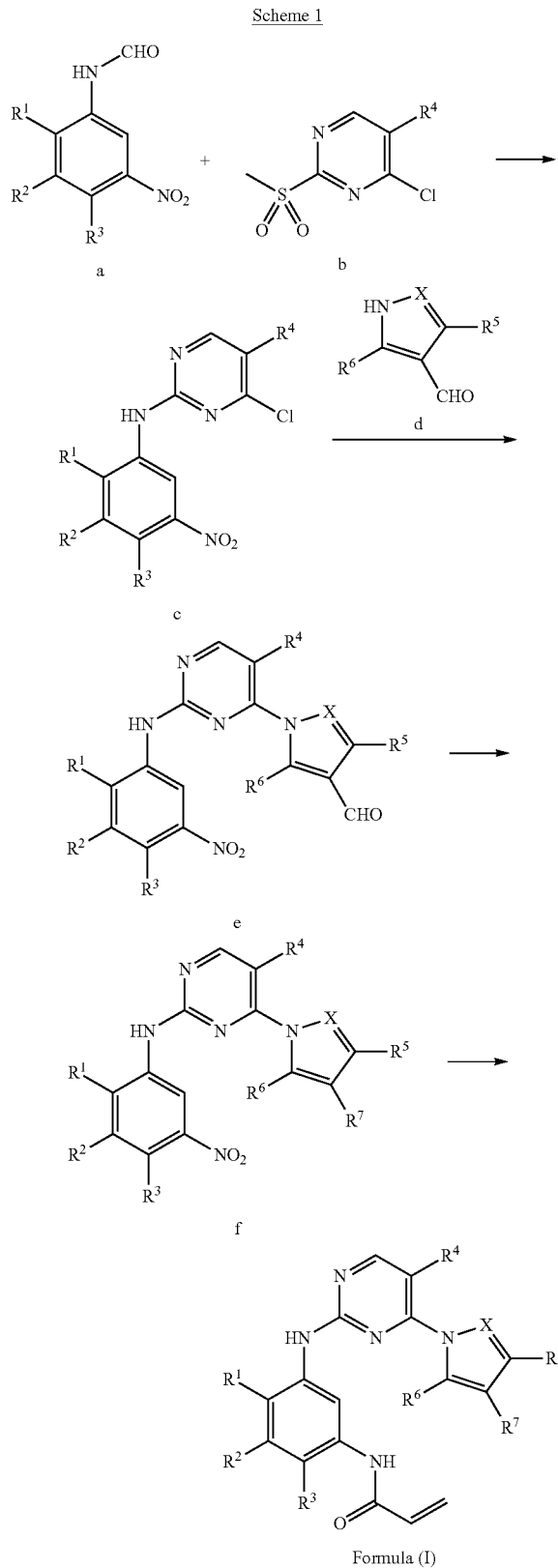

Scheme 2

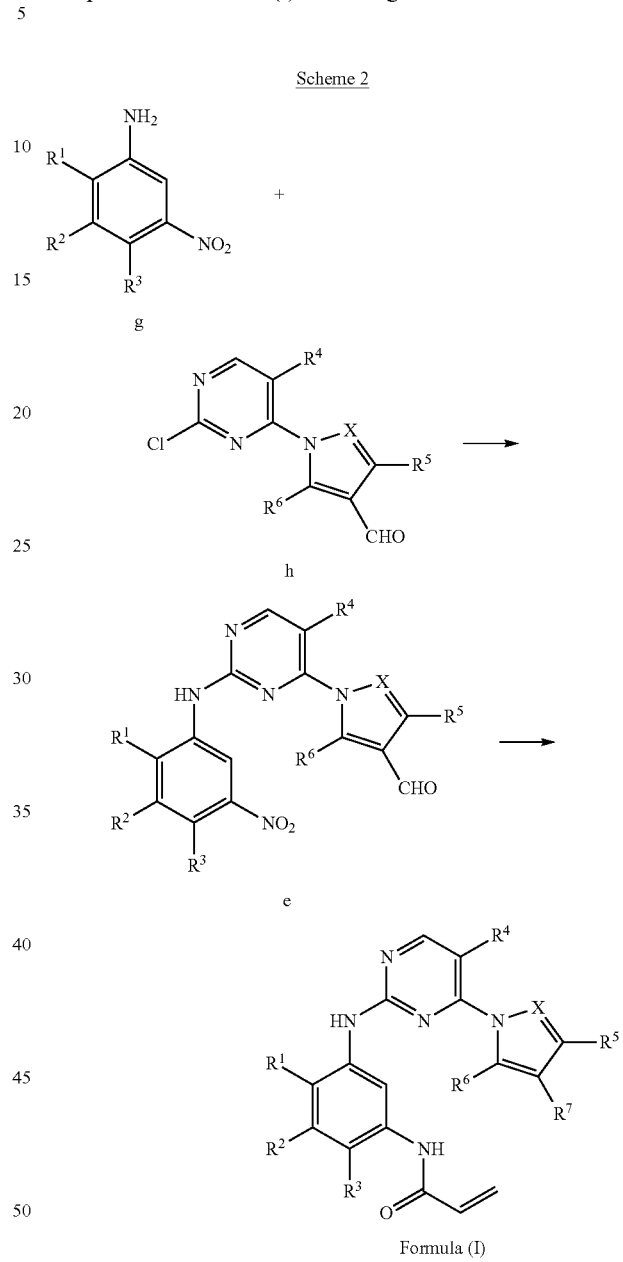

the presence of the fourth base in the first solvent, a ligand, a palladium catalyst in the first organic solvent (see Scheme 2). The invention also provides a method of preparing a compound of Formula (I) according to Scheme 2.

In certain aspects, the invention also provides a method of preparing a compound of formula (e) by reaction of the compound of formula (h) with aniline intermediates (g) in In certain aspects, the invention also provides (i) a method of preparing a compound of formula (j) from the compound of formula (i) with aniline intermediates (g) with the procedure as described in WO2013/109882 A1; (ii) a method of preparing a compound of formula (j) from the compound of formula (j) by oxidation with mCPBA or Oxone® as described in WO2013/109882 A1; (iii) a method of preparing the compound of formula (e) from a compound of formula (k) by reaction with the compound of formula (d) in the presence of the second base in the second organic solvent (see Scheme 3). The invention also provides a method of preparing a compound of Formula (I) according to Scheme 3.

Scheme 3

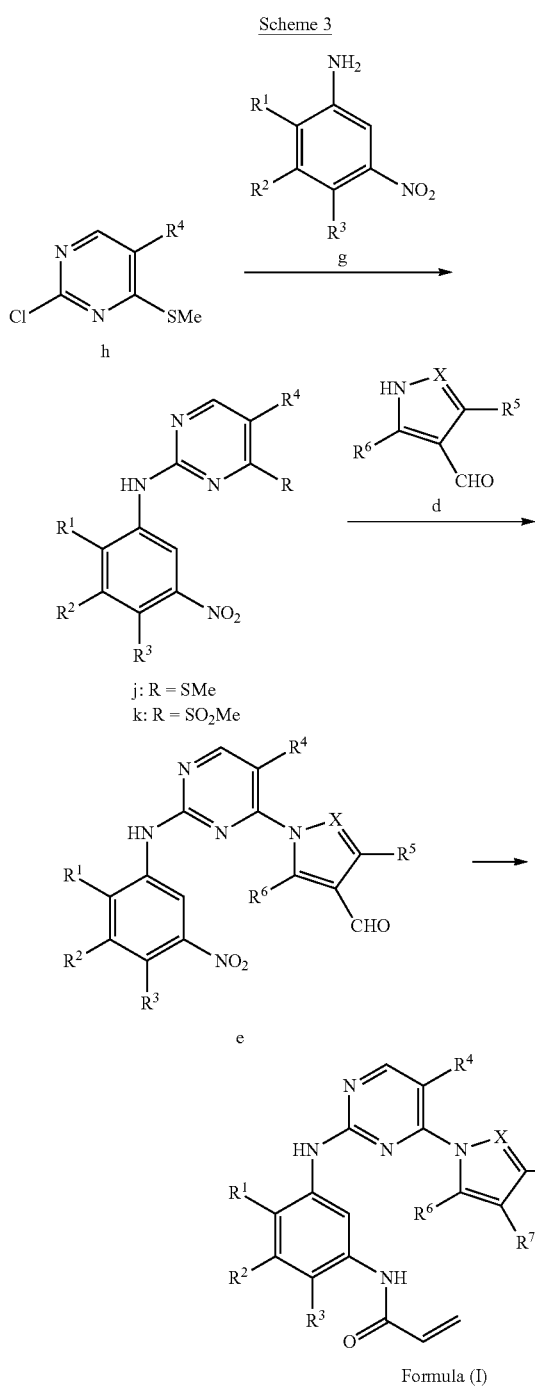

j: R = SMe
k: R = SO₂Me

Formula (I)

With reference to Schemes 1-3, while appropriate reaction solvents can be selected by one of ordinary skill in the art, the first organic solvent is generally selected from relatively polar, aprotic solvents such as acetone, tetrahydrofuran, N,N-dimethylformamide, N,N-dimethylacetamide, dichloromethane, dichloroethane, or acetonitrile; the second organic solvent is generally selected from aprotic solvents such as toluene, dioxane, tetrahydrofuran, N,N-dimethylformamide, N,N-dimethylacetamide or N-methylmorpholine; the third organic solvent is generally selected from relatively polar, solvents such as tetrahydrofuran, methanol, ethanol, dichloromethane, dichloroethane, N,N-dimethylacetamide or N,N-dimethylformamide; the fourth solvent is generally selected from relatively polar, protic solvents such as methanol, ethanol, tert-butanol or water, and the fifth solvent is generally selected from solvents such as dichloromethane, tetrahydrofuran, N,N-dimethylformamide, N,N-dimethylacetamide, or water.

With reference to Schemes 1-3, while bases and other reactants can be selected by one of ordinary skill in the art, the first and the second bases are generally selected from bases such as $K_2CO_3$, $Cs_2CO_3$, NaOH, KOH, NaH, tert-BuOK, ter-BuONa, triethylamine, or diisopropylethylamine; the third base is generally selected from bases such as triethylamine, diisopropylethylamine, NaH, NaHCO₃, tert-BuOK, tert-BuONa, $Cs_2CO_3$, or $K_2CO_3$; the fourth base is selected generally from bases such as NaH, n-BuLi, $Cs_2CO_3$, triethylamine, or diisopropylethylamine; a palladium catalyst is generally selected from Pd(OAc)₂, Pd₂(dba)₃, Pd(PPh₃)₄, or Pd(dppf)Cl₂; a ligand is generally selected from BINAP, Xantphos, or S-Phos; the oxidizing agent is selected from oxidizing agents such as m-chloroperbenzoic acid (mCPBA) or Oxone®; and the reducing agent is generally selected from NaBH(OAc)₃, NaBH₄, or NaBH(CN)₃.

Representative compounds of Formula (I) are listed below:

N-(3-(4-(4-(azetidin-1-ylmethyl)-3-methyl-1H-pyrazol-1-yl)pyrimidin-2-ylamino)-4-methoxyphenyl)acrylamide, N-(3-(4-(4-((3-hydroxyazetidin-1-yl)methyl)-3-methyl-1H-pyrazol-1-yl)pyrimidin-2-ylamino)-4-methoxyphenyl)acrylamide, N-(3-(4-(4-(azetidin-1-ylmethyl)-3-methyl-1H-pyrazol-1-yl)pyrimidin-2-ylamino)phenyl)acrylamide, N-(3-(4-(4-((3-hydroxyazetidin-1-yl)methyl)-3-methyl-1H-pyrazol-1-yl)pyrimidin-2-ylamino)phenyl)acrylamide, N-(3-(4-(4-((3-hydroxyazetidin-1-yl)methyl)-3-methyl-1H-pyrazol-1-yl)pyrimidin-2-ylamino)-5-methylphenyl)acrylamide, N-(5-(4-(4-((dimethylamino)methyl)-3-(4-fluorophenyl)-1H-pyrazol-1-yl)pyrimidin-2-ylamino)-4-methoxy-2-morpholinophenyl)acrylamide, N-(5-(4-(3-tert-butyl-4-((dimethylamino)methyl)-1H-pyrazol-1-yl)-5-methylpyrimidin-2-ylamino)-4-methoxy-2-morpholinophenyl)acrylamide, N-(3-(4-(4-((3-hydroxyazetidin-1-yl)methyl)-3-methyl-1H-pyrazol-1-yl)-5-methylpyrimidin-2-ylamino)-4-methoxyphenyl)acrylamide, N-(4-methoxy-3-(4-(3-methyl-1H-pyrazol-1-yl)pyrimidin-2-ylamino)phenyl)acrylamide, N-(3-(4-(4-((3-hydroxyazetidin-1-yl)methyl)-3-methyl-1H-pyrazol-1-yl)-5-methylpyrimidin-2-ylamino)-5-methylphenyl)acrylamide, N-(3-(4-(4-((3-hydroxyazetidin-1-yl)methyl)-1H-pyrazol-1-yl)-5-methylpyrimidin-2-ylamino)-4-methoxyphenyl)acrylamide, N-(5-(4-(4-(azetidin-1-ylmethyl)-3-methyl-1H-pyrazol-1-yl)pyrimidin-2-ylamino)-2-morpholinophenyl)acrylamide, N-(2-(4-acetylpiperazin-1-yl)-5-(4-(4-(azetidin-1-ylmethyl)-3-methyl-1H-pyrazol-1-yl)pyrimidin-2-ylamino)phenyl)acrylamide, N-(5-(4-(4-(azetidin-1-ylmethyl)-3-methyl-1H-pyrazol-1-yl)pyrimidin-2-ylamino)-4-methoxy-2-morpholinophenyl)acrylamide, N-(5-(4-(4-((3-hydroxyazetidin-1-yl)methyl)-3-methyl-1H-pyrazol-1-yl)pyrimidin-2-ylamino)-4-methoxy-2-morpholinophenyl)acrylamide, N-(5-(4-(4-(azetidin-1-ylmethyl)-3-methyl-1H-pyrazol-1-yl)pyrimidin-2-ylamino)-2-((2-(dimethylamino)ethyl)(methyl)amino)-4-methoxyphenyl)acrylamide, N-(5-(4-(4-(azetidin-1-ylmethyl)-3-methyl-1H-pyrazol-1-yl)pyrimidin-2-ylamino)-4-methoxy-2-(4-methylpiperazin-1-yl)phenyl)acrylamide, N-(5-(4-(4-(azetidin-1-ylmethyl)-3-methyl-1H-pyrazol-1-yl)pyrimidin-2-ylamino)-4-methoxy-2-(piperidin-1-yl)phenyl)acrylamide, N-(5-(4-(4-((3-hydroxyazetidin-1-yl)methyl)-1H-pyrazol-1-yl)-5-methylpyrimidin-2-ylamino)-4-methoxy-2-morpholinophenyl)acrylamide, N-(5-(4-(4-(((3R,4S)-3,4-dihydroxypyrrolidin-1-yl)methyl)-1H-pyrazol-1-yl)-5-methylpyrimidin-2-ylamino)-4-methoxy-2-morpholinophenyl)acrylamide, N-(5-(4-(4-(((3S,4R)-3-hydroxy-4-methoxypyrrolidin-1-yl)methyl)-1H-pyrazol-1-yl)-5-methylpyrimidin-2-ylamino)-4-methoxy-2-morpholinophenyl)acrylamide, N-(5-(4-(4-((dimethylamino)methyl)-1H-pyrazol-1-yl)-5-methylpyrimidin-2-ylamino)-4-methoxy-2-morpholinophenyl)acrylamide, N-(4-methoxy-5-(5-methyl-4-(4-((methyl(1-methylazetidin-3-yl)amino)methyl)-1H-pyrazol-1-yl)pyrimidin-2-ylamino)-2-morpholinophenyl)acrylamide, N-(5-(4-(4-((3-hydroxyazetidin-1-yl)methyl)-3-methyl-1H-pyrazol-1-yl)-5-methylpyrimidin-2-ylamino)-4-methoxy-2-morpholinophenyl)acrylamide, N-(5-(4-(4-(((3R,4S)-3,4-dihydroxypyrrolidin-1-yl)methyl)-3-methyl-1H-pyrazol-1-yl)-5-methylpyrimidin-2-ylamino)-4-methoxy-2-morpholinophenyl)acrylamide, N-(5-(4-(4-(((3S,4R)-3-hydroxy-4-methoxypyrrolidin-1-yl)methyl)-3-methyl-1H-pyrazol-1-yl)-5-methylpyrimidin-2-ylamino)-4-methoxy-2-morpholinophenyl)acrylamide, (R)—N-(5-(4-(4-((3-hydroxypyrrolidin-1-yl)methyl)-3-methyl-1H-pyrazol-1-yl)-5-methylpyrimidin-2-ylamino)-4-methoxy-2-morpholinophenyl)acrylamide, (S)—N-(5-(4-(4-((3-hydroxypyrrolidin-1-yl)methyl)-3-methyl-1H-pyrazol-1-yl)-5-methylpyrimidin-2-ylamino)-4-methoxy-2-morpholinophenyl)acrylamide, N-(5-(4-(4-((3-hydroxyazetidin-1-yl)methyl)-3-methyl-1H-pyrazol-1-yl)-5-methylpyrimidin-2-ylamino)-4-methoxy-2-(4-methylpiperazin-1-yl)phenyl)acrylamide, N-(5-(4-(4-((3-hydroxyazetidin-1-yl)methyl)-3-methyl-1H-pyrazol-1-yl)-5-methylpyrimidin-2-ylamino)-4-methoxy-2-(piperidin-1-yl)phenyl)acrylamide, N-(2-((2-(dimethylamino)ethyl)(methyl)amino)-5-(4-(4-((3-hydroxyazetidin-1-yl)methyl)-3-methyl-1H-pyrazol-1-yl)-5-methylpyrimidin-2-ylamino)-4-methoxyphenyl)acrylamide, N-(5-(4-(4-(azetidin-1-ylmethyl)-1H-pyrazol-1-yl)-5-methylpyrimidin-2-ylamino)-4-methoxy-2-morpholinophenyl)acrylamide, N-(4-methoxy-5-(5-methyl-4-(4-(morpholinomethyl)-1H-pyrazol-1-yl)pyrimidin-2-ylamino)-2-(4-methylpiperazin-1-yl)phenyl)acrylamide, N-(5-(4-(4-(azetidin-1-ylmethyl)-1H-pyrazol-1-yl)pyrimidin-2-ylamino)-4-methoxy-2-morpholinophenyl)acrylamide, (S)—N-(5-(4-(4-((3-(dimethylamino)pyrrolidin-1-yl)methyl)-1H-pyrazol-1-yl)pyrimidin-2-ylamino)-4-methoxy-2-morpholinophenyl)acrylamide, N-(5-(4-(4-(azetidin-1-ylmethyl)-1H-pyrazol-1-yl)-5-methylpyrimidin-2-ylamino)-4-methoxy-2-(4-methylpiperazin-1-yl)phenyl)acrylamide, N-(2-(4-acetylpiperazin-1-yl)-5-(4-(4-(azetidin-1-ylmethyl)-1H-pyrazol-1-yl)-5-methylpyrimidin-2-ylamino)-4-methoxyphenyl)acrylamide, N-(5-(4-(4-(azetidin-1-ylmethyl)-1H-pyrazol-1-yl)pyrimidin-2-ylamino)-2-(dimethylamino)-4-methoxyphenyl)acrylamide, (R)—N-(5-(4-(4-((3-(dimethylamino)pyrrolidin-1-yl)methyl)-1H-pyrazol-1-yl)pyrimidin-2-ylamino)-4-methoxy-2-morpholinophenyl)acrylamide, N-(5-(4-(4-(azetidin-1-ylmethyl)-1H-pyrazol-1-yl)-5-methylpyrimidin-2-ylamino)-4-methoxy-2-(1,4-oxazepan-4-yl)phenyl)acrylamide, N-(5-(4-(4-(azetidin-1-ylmethyl)-1H-pyrazol-1-yl)-5-methylpyrimidin-2-ylamino)-4-methoxy-2-(4-methyl-1,4-diazepan-1-yl)phenyl)acrylamide, N-(5-(4-(4-(azetidin-1-ylmethyl)-1H-pyrazol-1-yl)-5-methylpyrimidin-2-ylamino)-2-((2-(dimethylamino)ethyl)(methyl)amino)-4-methoxyphenyl)acrylamide, N-(2-((2-(dimethylamino)ethyl)(methyl)amino)-5-(4-(4-(((3S,4R)-3-hydroxy-4-methoxypyrrolidin-1-yl)methyl)-1H-pyrazol-1-yl)-5-methylpyrimidin-2-ylamino)-4-methoxyphenyl)acrylamide, N-(4-methoxy-5-(4-(4-((3-methoxyazetidin-1-yl)methyl)-3-methyl-1H-pyrazol-1-yl)pyrimidin-2-ylamino)-2-morpholinophenyl)acrylamide, N-(5-(4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide, N-(5-(4-(4-((dimethylamino)methyl)-3-methyl-1H-pyrazol-1-yl)pyrimidin-2-ylamino)-4-methoxy-2-morpholinophenyl)acrylamide, N-(5-(4-(4-((dimethylamino)methyl)-3-methyl-1H-pyrazol-1-yl)pyrimidin-2-ylamino)-4-methoxy-2-(4-methylpiperazin-1-yl)phenyl)acrylamide, N-(5-(4-(3-((3-hydroxyazetidin-1-yl)methyl)-4-methyl-1H-pyrrol-1-yl)-5-methylpyrimidin-2-ylamino)-4-methoxy-2-morpholinophenyl)acrylamide, N-(5-(5-chloro-4-(4-((3-hydroxyazetidin-1-yl)methyl)-3-methyl-1H-pyrazol-1-yl)pyrimidin-2-ylamino)-4-methoxy-2-morpholinophenyl)acrylamide, N-(5-(4-(4-(azetidin-1-ylmethyl)-3-methyl-1H-pyrazol-1-yl)-5-chloropyrimidin-2-ylamino)-4-methoxy-2-morpholinophenyl)acrylamide, N-(5-(5-chloro-4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide, N-(5-(5-chloro-4-(4-((dimethylamino)methyl)-3-methyl-1H-pyrazol-1-yl)pyrimidin-2-ylamino)-4-methoxy-2-morpholinophenyl)acrylamide, N-(5-(4-(4-(azetidin-1-ylmethyl)-3-methyl-1H-pyrazol-1-yl)pyrimidin-2-ylamino)-4-methoxy-2-(1H-pyrazol-1-yl)phenyl)acrylamide, N-(5-(5-chloro-4-(4-(((3R,4S)-3,4-dihydroxypyrrolidin-1-yl)methyl)-3-methyl-1H-pyrazol-1-yl)pyrimidin-2-ylamino)-4-methoxy-2-(4-methylpiperazin-1-yl)phenyl)acrylamide, N-(5-(4-(4-(azetidin-1-ylmethyl)-3-cyclopropyl-1H-pyrazol-1-yl)pyrimidin-2-ylamino)-4-methoxy-2-morpholinophenyl)acrylamide, N-(5-(4-(3-cyclopropyl-4-(((3S,4R)-3-hydroxy-4-methoxypyrrolidin-1-yl)methyl)-1H-pyrazol-1-yl)pyrimidin-2-ylamino)-4-methoxy-2-morpholinophenyl)acrylamide, N-(3-(4-(4-((3-hydroxyazetidin-1-yl)methyl)-3-methyl-1H-pyrazol-1-yl)pyrimidin-2-ylamino)-5-(1-methyl-1H-pyrazol-4-yl)phenyl)acrylamide, N-(5-(4-(4-((3-hydroxyazetidin-1-yl)methyl)-3-methyl-1H-pyrazol-1-yl)pyrimidin-2-ylamino)-4-methoxy-2-(1-methyl-1H-pyrazol-4-yl)phenyl)acrylamide, N-(5-(4-(4-(azetidin-1-ylmethyl)-3-methyl-1H-pyrazol-1-yl)pyrimidin-2-ylamino)-4-methoxy-2-(1-methyl-1,2,3,6-tetrahydropyridin-4-yl)phenyl)acrylamide, N-(5-(4-(3-(azetidin-1-ylmethyl)-4-methyl-1H-pyrrol-1-yl)-5-fluoropyrimidin-2-ylamino)-4-methoxy-2-morpholinophenyl)acrylamide, N-(5-(5-fluoro-4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide, N-(5-(4-(4-(azetidin-1-ylmethyl)-3-methyl-1H-pyrazol-1-yl)-5-fluoropyrimidin-2-ylamino)-4-methoxy-2-morpholinophenyl)acrylamide, N-(5-(4-(4-(azetidin-1-ylmethyl)-1H-pyrazol-1-yl)-5-methylpyrimidin-2-ylamino)-4-isopropoxy-2-morpholinophenyl)acrylamide, N-(5-(4-(4-(azetidin-1-ylmethyl)-1H-pyrazol-1-yl)-5-methylpyrimidin-2-ylamino)-4-methoxy-2-(1-methyl-1,2,3,6-tetrahydropyridin-4-yl)phenyl)acrylamide, N-(4-(4-(4-(azetidin-1-ylmethyl)-3-methyl-1H-pyrazol-1-yl)pyrimidin-2-ylamino)-5-methoxybiphenyl-2-yl)acrylamide, N-(5-(4-(4-(hydroxymethyl)-3-methyl-1H-pyrazol-1-yl)pyrimidin-2-ylamino)-4-methoxy-2-morpholinophenyl)acrylamide, N-(5-(4-(4-(azetidin-1-ylmethyl)-3-tert-butyl-1H-pyrazol-1-yl)-5-methylpyrimidin-2-ylamino)-4-methoxy-2-morpholinophenyl)acrylamide, N-(4-(4-(4-(azetidin-1-ylmethyl)-3-methyl-1H-pyrazol-1-yl)pyrimidin-2-ylamino)-2',5-dimethoxybiphenyl-2-yl)acrylamide, N-(5-(4-(4-(azetidin-1-ylmethyl)-3-methyl-1H-pyrazol-1-yl)pyrimidin-2-ylamino)-2-(4,4-difluoropiperidin-1-yl)-4-methoxyphenyl)acrylamide, N-(5-(4-(4-(azetidin-1-ylmethyl)-3,5-dimethyl-1H-pyrazol-1-yl)pyrimidin-2-ylamino)-4-methoxy-2-morpholinophenyl)acrylamide, N-(2-(dimethylamino)-5-(4-(4-((dimethylamino)methyl)-3-methyl-1H-pyrazol-1-yl)pyrimidin-2-ylamino)-4-methoxyphenyl)acrylamide, N-(5-(4-(4-((3-fluoroazetidin-1-yl)methyl)-3-methyl-1H-pyrazol-1-yl)pyrimidin-2-ylamino)-4-methoxy-2-morpholinophenyl)acrylamide, N-(5-(4-(4-((dimethylamino)methyl)-3-phenyl-1H-pyrazol-1-yl)pyrimidin-2-ylamino)-4-methoxy-2-morpholinophenyl)acrylamide, N-(5-(4-(3-cyclopropyl-4-((dimethylamino)methyl)-1H-pyrazol-1-yl)pyrimidin-2-ylamino)-4-methoxy-2-morpholinophenyl)acrylamide, N-(5-(4-(4-((dimethylamino)methyl)-3-methyl-1H-pyrazol-1-yl)-5-methylpyrimidin-2-ylamino)-4-methoxy-2-morpholinophenyl)acrylamide, N-(5-(4-(4-(azetidin-1-ylmethyl)-3-methyl-1H-pyrazol-1-yl)-5-methylpyrimidin-2-ylamino)-4-methoxy-2-morpholinophenyl)acrylamide, N-(5-(5-chloro-4-(4-((dimethylamino)methyl)-1H-pyrazol-1-yl)pyrimidin-2-ylamino)-4-methoxy-2-morpholinophenyl)acrylamide, N-(5-(4-(4-(azetidin-1-ylmethyl)-3-phenyl-1H-pyrazol-1-yl)pyrimidin-2-ylamino)-4-methoxy-2-morpholinophenyl)acrylamide, N-(5-(4-(4-((dimethylamino)methyl)-3-methyl-1H-pyrazol-1-yl)pyrimidin-2-ylamino)-2-(4-(2-fluoroethyl)piperazin-1-yl)-4-methoxyphenyl)acrylamide, N-(5-(4-(4-((dimethylamino)methyl)-3-p-tolyl-1H-pyrazol-1-yl)pyrimidin-2-ylamino)-4-methoxy-2-morpholinophenyl)acrylamide, N-(5-(4-(4-(azetidin-1-ylmethyl)-3-(4-fluorophenyl)-1H-pyrazol-1-yl)pyrimidin-2-ylamino)-4-methoxy-2-morpholinophenyl)acrylamide, N-(5-(4-(4-(azetidin-1-ylmethyl)-3-p-tolyl-1H-pyrazol-1-yl)pyrimidin-2-ylamino)-4-methoxy-2-morpholinophenyl)acrylamide, N-(2-(dimethylamino)-5-(4-(4-((dimethylamino)methyl)-3-phenyl-1H-pyrazol-1-yl)pyrimidin-2-ylamino)-4-methoxyphenyl)acrylamide, N-(2-(azetidin-1-yl)-5-(4-(4-((dimethylamino)methyl)-3-phenyl-1H-pyrazol-1-yl)pyrimidin-2-ylamino)-4-methoxyphenyl)acrylamide, N-(4-methoxy-2-(4-methylpiperazin-1-yl)-5-(4-(3-phenyl-1H-pyrazol-1-yl)pyrimidin-2-ylamino)phenyl)acrylamide, N-(5-(4-(3-tert-butyl-4-((dimethylamino)methyl)-1H-pyrazol-1-yl)pyrimidin-2-ylamino)-4-methoxy-2-morpholinophenyl)acrylamide, N-(2-(azetidin-1-yl)-5-(4-(4-(azetidin-1-ylmethyl)-3-phenyl-1H-pyrazol-1-yl)pyrimidin-2-ylamino)-4-methoxyphenyl)acrylamide, N-(5-(4-(4-((dimethylamino)methyl)-3-(thiophen-2-yl)-1H-pyrazol-1-yl)pyrimidin-2-ylamino)-4-methoxy-2-morpholinophenyl)acrylamide, N-(5-(4-(4-((dimethylamino)methyl)-3-(2,5-dimethylphenyl)-1H-pyrazol-1-yl)pyrimidin-2-ylamino)-4-methoxy-2-morpholinophenyl)acrylamide, N-(4-methoxy-2-morpholino-5-(4-(3-phenyl-4-(pyrrolidin-1-ylmethyl)-1H-pyrazol-1-yl)pyrimidin-2-ylamino)phenyl)acrylamide, N-(5-(4-(4-(hydroxymethyl)-3-phenyl-1H-pyrazol-1-yl)pyrimidin-2-ylamino)-4-methoxy-2-morpholinophenyl)acrylamide, N-(5-(4-(4-((ethyl(methyl)amino)methyl)-3-phenyl-1H-pyrazol-1-yl)pyrimidin-2-ylamino)-4-methoxy-2-morpholinophenyl)acrylamide, N-(5-(4-(4-((dimethylamino)methyl)-3-isopropyl-1H-pyrazol-1-yl)pyrimidin-2-ylamino)-4-methoxy-2-morpholinophenyl)acrylamide, N-(5-(4-(4-((dimethylamino)methyl)-3-phenyl-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-phenyl-1H-pyrazol-1-yl)pyrimidin-2-ylamino)-4-methoxy-2-((2-methoxyethyl)(methyl)amino)phenyl)acrylamide, N-(5-(4-(4-((dimethylamino)methyl)-3-phenyl-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-phenyl-1H-pyrazol-1-yl)pyrimidin-2-ylamino)-4-methoxy-2-(methyl(oxetan-3-yl)amino)phenyl)acrylamide, N-(5-(4-(4-((dimethylamino)methyl)-3-phenyl-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-phenyl-1H-pyrazol-1-yl)pyrimidin-2-ylamino)-4-methoxy-2-(pyrrolidin-1-yl)phenyl)acrylamide, N-(5-(4-(3-tert-butyl-4-((dimethylamino)methyl)-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-tert-butyl-1H-pyrazol-1-yl)pyrimidin-2-ylamino)-4-methoxy-2-((2-methoxyethyl)(methyl)amino)phenyl)acrylamide, N-(5-(4-(3-tert-butyl-4-((dimethylamino)methyl)-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-tert-butyl-1H-pyrazol-1-yl)pyrimidin-2-ylamino)-4-methoxy-2-(methyl(oxetan-3-yl)amino)phenyl)acrylamide, N-(5-(4-(3-tert-butyl-4-((dimethylamino)methyl)-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-tert-butyl-1H-pyrazol-1-yl)pyrimidin-2-ylamino)-4-methoxy-2-(pyrrolidin-1-yl)phenyl)acrylamide, N-(5-(4-(3-cyclopropyl-4-((dimethylamino)methyl)-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-cyclopropyl-1H-pyrazol-1-yl)pyrimidin-2-ylamino)-4-methoxy-2-((2-methoxyethyl)(methyl)amino)phenyl)acrylamide, N-(5-(4-(3-cyclopropyl-4-((dimethylamino)methyl)-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-cyclopropyl-1H-pyrazol-1-yl)pyrimidin-2-ylamino)-4-methoxy-2-(methyl(oxetan-3-yl)amino)phenyl)acrylamide, N-(5-(4-(3-cyclopropyl-4-((dimethylamino)methyl)-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-cyclopropyl-1H-pyrazol-1-yl)pyrimidin-2-ylamino)-4-methoxy-2-(pyrrolidin-1-yl)phenyl)acrylamide, N-(5-(4-(4-((dimethylamino)methyl)-3-isopropyl-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-isopropyl-1H-pyrazol-1-yl)pyrimidin-2-ylamino)-4-methoxy-2-((2-methoxyethyl)(methyl)amino)phenyl)acrylamide, N-(5-(4-(4-((dimethylamino)methyl)-3-isopropyl-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-isopropyl-1H-pyrazol-1-yl)pyrimidin-2-ylamino)-4-methoxy-2-(methyl(oxetan-3-yl)amino)phenyl)acrylamide, N-(5-(4-(4-((dimethylamino)methyl)-3-isopropyl-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-isopropyl-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-(thiophen-2-yl)-1H-pyrazol-1-yl)pyrimidin-2-ylamino)-4-methoxy-2-morpholinophenyl)acrylamide, N-(5-(4-(4-(azetidin-1-ylmethyl)-3-isopropyl-1H-pyrazol-1-yl)pyrimidin-2-ylamino)-4-methoxy-2-morpholinophenyl)acrylamide, N-(5-(4-(4-((dimethylamino)methyl)-3-phenyl-1H-pyrazol-1-yl)-5-methylpyrimidin-2-ylamino)-4-methoxy-2-morpholinophenyl)acrylamide, N-(5-(4-(4-(azetidin-1-ylmethyl)-3-phenyl-1H-pyrazol-1-yl)-5-methylpyrimidin-2-ylamino)-4-methoxy-2-morpholinophenyl)acrylamide, N-(5-(4-(3-cyclopropyl-4-((dimethylamino)methyl)-1H-pyrazol-1-yl)-5-methylpyrimidin-2-ylamino)-4-methoxy-2-morpholinophenyl)acrylamide, N-(5-(4-(4-(azetidin-1-ylmethyl)-3-cyclopropyl-1H-pyrazol-1-yl)-5-methylpyrimidin-2-ylamino)-4-methoxy-2-morpholinophenyl)acrylamide, N-(5-(4-(4-((dimethylamino)methyl)-3-isopropyl-1H-pyrazol-1-yl)-5-methylpyrimidin-2-ylamino)-4-methoxy-2-morpholinophenyl)acrylamide, N-(5-(4-(4-(azetidin-1-ylmethyl)-3-isopropyl-1H-pyrazol-1-yl)-5-methylpyrimidin-2-ylamino)-4-methoxy-2-morpholinophenyl)acrylamide, N-(5-(4-(3-tert-butyl-4-((dimethylamino)methyl)-1H-pyrazol-1-yl)pyrimidin-2-ylamino)-2-(ethyl(2-methoxyethyl)amino)-4-methoxyphenyl)acrylamide, N-(5-(4-(4-((dimethylamino)methyl)-3-(furan-3-yl)-1H-pyrazol-1-yl)pyrimidin-2-ylamino)-4-methoxy-2-morpholinophenyl)acrylamide, N-(5-(4-(4-((dimethylamino)methyl)-3-(pyridin-3-yl)-1H-pyrazol-1-yl)pyrimidin-2-ylamino)-4-methoxy-2-morpholinophenyl)acrylamide, N-(2-(4-acetylpiperazin-1-yl)-5-(4-(3-cyclopropyl-4-((dimethylamino)methyl)-1H-pyrazol-1-yl)pyrimidin-2-ylamino)-4-methoxyphenyl)acrylamide, N-(5-(4-(3-(azetidin-1-ylmethyl)-4-(furan-3-yl)-1H-pyrrol-1-yl)-5-fluoropyrimidin-2-ylamino)-4-methoxy-2-morpholinophenyl)acrylamide, N-(5-(4-(3-((dimethylamino)methyl)-4-(furan-3-yl)-1H-pyrrol-1-yl)-5-fluoropyrimidin-2-ylamino)-4-methoxy-2-morpholinophenyl)acrylamide, N-(5-(4-(3-cyclopropyl-4-((dimethylamino)methyl)-1H-pyrazol-1-yl)-5-methylpyrimidin-2-ylamino)-4-methoxy-2-(methyl(oxetan-3-yl)amino)phenyl)acrylamide, N-(2-(4-acetylpiperazin-1-yl)-5-(4-(4-(azetidin-1-ylmethyl)-3-phenyl-1H-pyrazol-1-yl)pyrimidin-2-ylamino)-4-methoxyphenyl)acrylamide, N-(2-(4-acetylpiperazin-1-yl)-5-(4-(4-((dimethylamino)methyl)-3-phenyl-1H-pyrazol-1-yl)pyrimidin-2-ylamino)-4-methoxyphenyl)acrylamide, N-(5-(4-(4-((dimethylamino)methyl)-3-(pyridin-4-yl)-1H-pyrazol-1-yl)pyrimidin-2-ylamino)-4-methoxy-2-morpholinophenyl)acrylamide, N-(2-(4-acetylpiperazin-1-yl)-5-(4-(3-cyclopropyl-4-((ethyl(methyl)amino)methyl)-1H-pyrazol-1-yl)pyrimidin-2-ylamino)-4-methoxyphenyl)acrylamide, N-(2-(4-acetylpiperazin-1-yl)-5-(4-(4-(azetidin-1-ylmethyl)-3-cyclopropyl-1H-pyrazol-1-yl)pyrimidin-2-ylamino)-4-methoxyphenyl)acrylamide, N-(2-(azetidin-1-yl)-5-(4-(4-(azetidin-1-ylmethyl)-3-cyclopropyl-1H-pyrazol-1-yl)pyrimidin-2-ylamino)-4-methoxyphenyl)acrylamide, N-(5-(4-(3-cyclopropyl-4-((ethyl(methyl)amino)methyl)-1H-pyrazol-1-yl)pyrimidin-2-ylamino)-4-methoxy-2-morpholinophenyl)acrylamide, N-(2-(azetidin-1-yl)-5-(4-(3-(azetidin-1-ylmethyl)-4-methyl-1H-pyrrol-1-yl)-5-fluoropyrimidin-2-ylamino)-4-methoxyphenyl)acrylamide, N-(5-(4-(3-(azetidin-1-ylmethyl)-4-methyl-1H-pyrrol-1-yl)-5-fluoropyrimidin-2-ylamino)-2-(dimethylamino)-4-methoxyphenyl)acrylamide, N-(2-(dimethylamino)-5-(4-(3-((dimethylamino)methyl)-4-methyl-1H-pyrrol-1-yl)-5-fluoropyrimidin-2-ylamino)-4-methoxyphenyl)acrylamide, N-(2-((2-(dimethylamino)ethyl)(methyl)amino)-5-(4-(3-((dimethylamino)methyl)-4-(trifluoromethyl)-1H-pyrrol-1-yl)-5-fluoropyrimidin-2-ylamino)-4-methoxyphenyl)acrylamide, N-(5-(4-(4-((ethyl(methyl)amino)methyl)-3-methyl-1H-pyrazol-1-yl)pyrimidin-2-ylamino)-4-methoxy-2-morpholinophenyl)acrylamide, or a pharmaceutically acceptable salt thereof.

As used herein, the term "cancer" refers to an abnormal growth of cells which tend to proliferate in an uncontrolled way and, in some cases, to metastasize. The types of cancer include, but is not limited to, solid tumors, such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

As used herein, the term "EGFR mutation" refers to mutation of T790M (resistant or oncogenic), L858R (activating), del E746-A750 (activating) or a combination thereof In certain embodiments, the invention selectively inhibits at one activating mutation and at one point mutation. In some embodiments, an at least one activating mutation is a deletion mutation, del E746-A750. In some embodiments, an at least one activating mutation is a point mutation L858R. In some embodiments, the at least one resistant mutation is a point mutation, T790M. In some embodiments, the at least one mutation of EGFR is L858R and/or T790M.

As used herein, the term "mutant selective inhibition", as used in comparison to inhibition of wildtype (WT) EGFR, refers to the state that invention inhibits at least one mutation of EGFR (i.e. at least one deletion mutation, at least one activating mutation, at least one resistant mutation, or a combination of at least one deletion mutation and at least one point mutation) in at least one assay described herein (e.g., biochemical or cellular).

As used herein, the term "selectively inhibits", as used in comparison to inhibition of other kinases, refers to that invention poorly inhibits at least one of kinase panel.

As used herein, the term "EGFR wildtype selectivity" refers to that a selective inhibitor of at least one mutation of EGFR, as defined and described above and herein, inhibits EGFR at the upper limit of detection of at least one assay as described herein (e.g. cellular as described in detail in Table 1 and Table 2). In some embodiments, the term "EGFR wildtype selectivity" means that the invention inhibits WT EGFR with an $IC_{50}$ of at least 200-1000 nM or >1000 nM.

As used herein, the term "inhibitor" refers to a compound which inhibits one or more kinase described herein. For example, the term "EGFR mutant inhibitor" refers to a compound which inhibits the EGFR mutant receptor or reduces the signaling effect.

As used herein, the term "pharmaceutically acceptable" refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein.

As used herein, the term "pharmaceutical combination" means a product that results from the mixing or combining of more than one active ingredient.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "prodrug" refers to an agent that is converted into the parent drug in vivo. Prodrugs are often useful because, in some situations, they may be easier to administer than the parent drug. Prodrugs are bio-available by oral administration whereas the parent is not. Prodrugs improve solubility in pharmaceutical compositions over the parent drug. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

As used herein, the term "protein kinase-mediated disease" or a "disorder or disease or condition mediated by inappropriate protein kinase activity" refers to any disease state mediated or modulated by protein kinases described herein. Such disease states include, but are not limited to non-small cell lung cancer (NSCLC).

As used herein, the term "EGFR mutant-mediated disease" or a "disorder or disease or condition mediated by inappropriate EGFR activity" refers to any disease state mediated or modulated by EGFR mutant kinase mechanisms. Such disease states include, but are not limited to NSCLC, metastatic brain cancer and other solid cancers.

As used herein, the term "JAK3-mediated disease" or a "disorder or disease or condition mediated by inappropriate JAK3 activity" refers to any disease state mediated or modulated by JAK3 kinase mechanisms. Such disease states include, but are not limited to rheumatoid arthritis, psoriasis and organ transplant rejection and some solid cancers.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "solvate" refers to a complex of variable stoichiometry formed by a solute (in this invention, a compound of Formula (I) or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "administration" or "administering" of the subject compound refers to providing a compound of the invention and/or prodrugs thereof to a subject in need of treatment.

As used herein, the term "carrier" refers to chemical compounds or agents that facilitate the incorporation of a compound described herein into cells or tissues.

As used herein, the term "co-administration" or "combined administration" or the like as used herein are meant to encompass administration of the selected therapeutic agents to a single patient, and are intended to include treatment regimens in which the agents are not necessarily administered by the same route of administration or at the same time.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "effective amount" or "therapeutically effective amount" refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. By way of example only, a therapeutically effective amount of a compound of the invention may be in the range of e.g., about 0.01 mg/kg/day to about 100 mg/kg/day, or from about 0.1 mg/kg/day to about 10 mg/kg/day.

Human Protein Kinase

Compounds of the present invention are screened against the kinase panel (wild type and/or mutation thereof) and inhibit the activity of at least one kinase on the kinase panel. Examples of kinases include, but are not limited to EGFR and JAK3 (JH1domain-catalytic) kinases, and mutant forms thereof. As such, the compounds and compositions of the invention are useful for treating diseases or disorders in which such kinases contribute to the pathology and/or symptomology of a disease or disorder associated with or mediated by such kinase.

Many diseases are associated with abnormal cellular responses triggered by protein kinase mediated events. These diseases include, but are not limited to, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone related diseases.

Phosphorylation regulates a variety of cellular processes such as proliferation, growth, differentiation, metabolism, apoptosis, motility, transcription, translation and other signaling processes. Aberrant or excessive PTK activity has been observed in many disease states such as benign and malignant proliferative disorders, diseases resulting from inappropriate activation of the immune system and diseases resulting from inappropriate activation of the nervous systems. Specific diseases or conditions include, but are not limited to, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, atherosclerosis, restenosis, autoimmune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, Alzheimer's disease, Parkinson's disease, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

Epidermal Growth Factor Receptor (EGFR)

The epidermal growth factor receptor (EGFR; ErbB-1; HER1 in human) is the cell-surface receptor for members of the epidermal growth factor family (EGF-family) of extracellular protein ligands. The epidermal growth factor receptor is a member of the ErbB family of receptors, a subfamily of four related receptor tyrosine kinases: EGFR (ErbB-1), HER2/c-neu (ErbB-2), Her 3 (ErbB-3) and Her 4 (ErbB-4). Mutations affecting EGFR expression or activity could result in cancer.

EGFR exists on the cell surface and is activated by binding of its specific ligands, including epidermal growth factor and transforming growth factor $\alpha$ (TGF$\alpha$). Upon activation by its growth factor ligands, EGFR undergoes a transition from an inactive monomeric form to an active homodimer. In addition to forming homodimers after ligand binding, EGFR may pair with another member of the ErbB receptor family, such as ErbB2/Her2/neu, to create an activated heterodimer. ErbB2 has no known direct activating ligand, and may be in an activated state constitutively or become active upon hetero-dimerization with other family members such as EGFR.

The dimerization of EGFR stimulates its intrinsic intracellular protein-tyrosine kinase activity. As a result, autophosphorylation of several tyrosine (Y) residues in the C-terminal domain of EGFR takes place. These include Y992, Y1045, Y1068, Y1148 and Y1173 at cytoplasmic domain. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation. Such proteins modulate phenotypes such as cell migration, adhesion, and proliferation. Activation of the receptor is important for the innate immune response in human skin. The kinase domain of EGFR can also cross-phosphorylate tyrosine residues of other receptors it is aggregated with, and can itself be activated in that manner.

Mutations that lead to EGFR overexpression (known as upregulation) or overactivity have been associated with a number of cancers, including lung cancer, anal cancers and glioblastoma multiforms. These somatic mutations involving EGFR lead to its constant activation, which produces uncontrolled cell division. In glioblastoma a more or less specific mutation of EGFR, called EGFRvIII is often observed. Mutations, amplifications or misregulations of EGFR or family members are implicated in about 30% of all epithelial cancers.

The most common form of lung cancer is non-small cell lung carcinoma (NSCLC) and in a subset of these patients lung tumor growth is caused by activating mutations in the epidermal growth factor receptor (EGFR). The most common activating mutations, accounting for 85-90% of all EGFR mutations, are the in-frame deletion in exon 19

(DelE746-A750) and the L858R point mutation in exon 21. EGFR mutations occur in 10-15% of NSCLC patients of Caucasian descent and 30-35% of NSCLC patients of East Asian descent. Clinical features likely to be associated with EGFR mutations are non-smoker and of East Asian ethnicity.

It was well known that the most common EGFR activating mutations, L858R and del E746-A750 were sensitive to treatment of gefitinib or erlotinib, which are associated with dose-limiting toxicities such as diarrhea and rash/acne in response to inhibition of wild-type EGFR in intestine and skin, respectively. Ultimately acquired resistance to therapy with gefitinib or erlotinib occurs predominantly by mutation of the gatekeeper residue T790M, which is detected in nearly half of clinically resistant patients, resulting in double mutants, L858R/T790M or del E746-A750/T790M.

Brain metastases are the most common intracranial neoplasm, occurring in 8-10% of cancer patients, and are a significant cause of cancer-related morbidity and mortality worldwide Brain metastases develop in approximately 30% of patients with non-small cell lung cancer (NSCLC). Among the various histologies of NSCLC, the relative frequency of brain metastases in patients with adenocarcinoma and large cell carcinoma was much higher than that in patients with squamous cell carcinoma.

The compounds described herein are inhibitors of EGFR mutant kinase activity and have therapeutic benefit in the treatment of disorders associated with inappropriate EGFR mutant activity, in particular in the treatment and prevention of disease states mediated by EGFR mutant. Such disease states include NSCLC, breast cancer, metastatic brain cancer and other solid cancers.

Furthermore, the compounds, compositions and methods of the present invention provides methods of regulating, and in particular inhibiting, signal transduction cascades in which EGFR mutant(s) plays a role. The method generally involves contacting a EGFR mutant-dependent receptor or a cell expressing a EGFR mutant-dependent receptor with an amount of a compound described herein, or prodrug a compound described herein, or an acceptable salt, hydrate, solvate, N-oxide and/or composition thereof, effective to regulate or inhibit the signal transduction cascade. The methods are used to regulate, and in particular inhibit, downstream processes or cellular responses elicited by activation of the particular EGFR mutant-dependent signal transduction cascade. The methods are practiced to regulate any signal transduction cascade where EGFR mutant is not known or later discovered to play a role. The methods are practiced in in vitro contexts or in in vivo contexts as a therapeutic approach towards the treatment or prevention of diseases characterized by, caused by or associated with activation of the EGFR mutant-dependent signal transduction cascade.

Janus Kinase 3 (JAK3)

Janus kinase 3 (JAK3) is a tyrosine kinase that belongs to the Janus family of kinases. Other members of the Janus family include JAK1, JAK2 and TYK2. They are cytosolic tyrosine kinases that are specifically associated with cytokine receptors. Since cytokine receptor proteins lack enzymatic activity, they are dependent upon JAKs to initiate signaling upon binding of their ligands (e.g. cytokines). The cytokine receptors can be divided into five major subgroups based on their different domains and activation motifs. JAK3 is required for signaling of the type I receptors that use the common gamma chain (γc).

In contrast to the relatively ubiquitous expression of JAK1, JAK2 and Tyk2, JAK3 is predominantly expressed in hematopoietic lineage such as NK cells, T cells and B cells and intestinal epithelial cells. JAK3 functions in signal transduction and interacts with members of the STAT (signal transduction and activators of transcription) family. JAK3 is involved in signal transduction by receptors that employ the common gamma chain (γc) of the type I cytokine receptor family (e.g. IL-2R, IL-4R, IL-7R, IL-9R, IL-15R, and IL-21R). Mutations of JAK3 result in severe combined immunodeficiency (SCID). Mice that do not express JAK3 have T-cells and B-cells that fail to respond to many cytokines.

Since JAK3 is required for immune cell development, targeting JAK3 could be a useful strategy to generate a novel class of immunosuppressant drugs. Moreover, unlike other JAKs, JAK3 is primarily expressed in hematopoietic cells, so a highly specific JAK3 inhibitor should have precise effects on immune cells and minimal pleiotropic defects. The selectivity of a JAK3 inhibitor would also have advantages over the current widely used immunosuppressant drugs, which have abundant targets and diverse side effects. A JAK3 inhibitor could be useful for treating autoimmune diseases, especially those in which a particular cytokine receptor has a direct role on disease pathogenesis. For example, signaling through the IL-15 receptor is known to be important in the development rheumatoid arthritis, and the receptors for IL-4 and IL-9 play roles in the development of allergic responses.

Extranodal, nasal-type natural killer (NK)/T-cell lymphoma (NKCL) is an aggressive malignancy with poor prognosis in which, usually, signal transducer and activator of transcription 3 (STAT3) is constitutively activated and oncogenic. It was demonstrated that STAT3 activation mostly results from constitutive Janus kinase 3 (JAK3) phosphorylation on tyrosine 980, as observed in three of the four tested NKCL cell lines and in 20 of the 23 NKCL tumor samples. In one of the cell lines and in 4 of 19 NKCL primary tumor samples, constitutive JAK3 activation was related to an acquired mutation (A573V or V722I) in the JAK3 pseudokinase domain. In addition, it was shown that constitutive activation of the JAK3/STAT3 pathway has a major role in NKCL cell growth and survival and in the invasive phenotype. Indeed, NKCL cell growth was slowed down in vitro by targeting JAK3 with chemical inhibitors or small-interfering RNAs. In a human NKCL xenograft mouse model, tumor growth was significantly delayed by the JAK3 inhibitor. Therefore, the constitutive activation of JAK3, which can result from JAK3-activating mutations, is a frequent feature of NKCL so that it could be therapeutic target.

The compounds described herein are inhibitors of JAK3 kinase activity and have therapeutic benefit in the treatment of disorders associated with inappropriate JAK3 activity, in particular in the treatment and prevention of disease states mediated by JAK3. Such disease states include rheumatoid arthritis, psoriasis and organ transplant rejection, lymphoma and some solid cancers.

Pharmaceutical Compositions, Formulation and Administration

For the therapeutic uses of compounds provided herein, including compounds of Formula (I), or pharmaceutically acceptable salts, solvates, N-oxides, prodrugs, or isomers thereof, such compounds are administered in therapeutically effective amounts either alone or as part of a pharmaceutical composition. Accordingly, provided herein are pharmaceutical compositions, which comprise at least one compound provided herein, including at least one compound of Formula (I), pharmaceutically acceptable salts and/or solvates thereof, and one or more pharmaceutically acceptable carriers, diluents, adjuvant or excipients. In addition, such compounds and compositions are administered singly or in combination with one or more additional therapeutic agents. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or optic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The therapeutically effective amount will vary depending on, among others, the disease indicated, the severity of the disease, the age and relative health of the subject, the potency of the compound administered, the mode of administration and the treatment desired. The required dosage will also vary depending on the mode of administration, the particular condition to be treated and the effect desired.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of the invention may be prepared from the corresponding base addition salt or acid addition salt form, respectively. For example a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug derivatives of the compounds of the invention may be prepared by methods known to those of ordinary skill in the art (e.g., for further details see Saulnier et al, Bioorg. Med. Chem. Letters, 1994, 4, 1985; the entire teachings of which are incorporated herein by reference).

Protected derivatives of the compounds of the invention may be prepared by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference. Compounds of the invention may be prepared as their individual stereoisomers by reaction of a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet and Samuel H. Wilen, "Enantiomers, Racemates and Resolutions," John Wiley And Sons, Inc., 1981, the entire teachings of which are incorporated herein by reference.

Suitable pharmaceutically acceptable carriers, diluents, adjuvants, or excipients for use in the pharmaceutical compositions of the invention include tablets (coated tablets) made of for example collidone or shellac, gum Arabic, talc, titanium dioxide or sugar, capsules (gelatin), solutions (aqueous or aqueous ethanolic solution), syrups containing the active substances, emulsions or inhalable powders (of various saccharides such as lactose or glucose, salts and mixture of these excipients with one another) and aerosols (propellant-containing or -free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

Compounds of Formula (I) can be made according to a variety of methods, some of which are known in the art. For example, the methods disclosed in PCT Publication WO2011/060295 (incorporated herein by reference) can be used, with suitable modifications, to prepare compounds according to the present invention. Exemplary methods for preparing the compounds of the invention are described herein, including in the Examples.

In certain embodiments, compounds of Formula (I) are made by: (a) optionally converting a compound of the invention into a pharmaceutically acceptable salt; (b) optionally converting a salt form of a compound of the invention to a non-salt form; (c) optionally converting an unoxidized form of a compound of the invention into a pharmaceutically acceptable N-oxide; (d) optionally resolving an individual isomer of a compound of the invention from a mixture of isomers; (e) optionally converting a non-derivatized compound of the invention into a pharmaceutically acceptable prodrug derivative; and (f) optionally converting a prodrug derivative of a compound of the invention to its non-derivatized form.

The teachings of all patents, published applications and references cited herein are incorporated by reference in their entirety.

EXAMPLES

The present invention is further exemplified by the following examples that illustrate the preparation of compounds of Formula (I) according to the invention. The examples are for illustrative purpose only and are not intended, nor should they be construed as limiting the invention in any manner. Those skilled in the art will appreciate that variations and modifications can be made without changing the scope of the invention.

Nuclear magnetic resonance (NMR) and mass spectrometry (MS) spectra obtained for compounds described in the examples below and those described herein were consistent with that of the compounds of formulae herein.

Liquid Chromatography-Mass Spectrometry (LC-MS) Method

1. Samples are run on Agilent Technologies 6120 MSD system with a Zorbax Eclipse XDB-C18 (3.5 μm) reverse phase column (4.6×50 mm) run at room temperature with flow rate of 1.5 mL/minute.

2. The mobile phase uses solvent A (water/0.1% formic acid) and solvent B (acetonitrile/0.1% formic acid): 95%/5% to 0%/100% (A/B) for 5 minute.

3. The mass spectra (m/z) were recorded using electrospray ionization (ESI).

4. Ionization data was rounded to the nearest integer.

Proton NMR Spectra

Unless otherwise indicated, all $^1$H NMR spectra are run on a Varian series Mercury 300 MHz or a Bruker 500 MHz. All observed protons are reported as parts-per-million (ppm) downfield from tetramethylsilane using conventional abbreviations for designation of major peaks: e.g., s (singlet), d (doublet), t (triplet), q (quartet), m (multiplet) and br (broad).

Intermediate 1: 1-(2-(2-Methoxy-5-nitrophenylamino)pyrimidin-4-yl)-3-methyl-1H-pyrazole-4-carbaldehyde

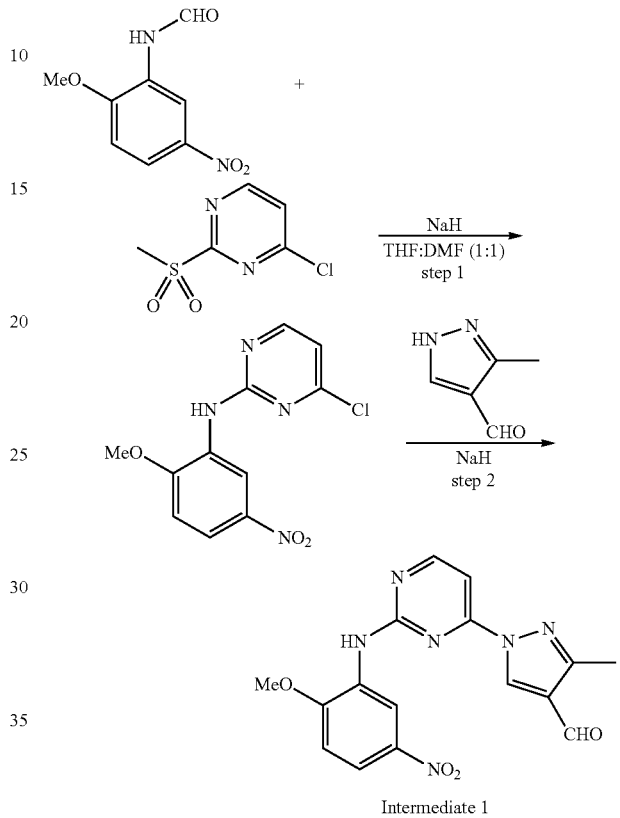

Step 1

To a solution of N-(2-methoxy-5-nitrophenyl)formamide (0.30 g, 1.53 mmol) in 4 mL of THF and DMF mixture (1:1) was added 122.4 mg of NaH (60%, 3.06 mmol) at 0° C. N-Formamide was prepared from 2-methoxy-5-nitroaniline with formic acid by the known procedure described in PCT Int, Appl. 2006102642. The resulting slurry was warmed to rt and stirred for 30 min and cooled again to 0° C. To the resulting mixture was added a solution of 4-chloro-2-(methylsulfonyl)pyrimidine (0.35 g, 1.84 mmol) in 2 mL of THF and DMF mixture (1:1). 2-(Methylsulfonyl)pyrimidine was synthesized using mCPBA or Oxone® respectively by known procedures described in PCT Int, Appl. 2007117465 and PCT Int, Appl. 2007023105. The mixture was stirred for 30 min at 0° C. Cold water and 3 mL of 1N aqueous NaOH was added to form solid. The mixture was stirred for 30 min at rt. The resulting solids were collected by filtration, rinsed with water and then vacuum dried to give 4-chloro-N-(2-methoxy-5-nitrophenyl)pyrimidin-2-amine as a yellow solid (0.40 g, 88%); MS (ESI) m/z 281 [M+H]$^+$.

Step 2

To a solution of 3-methyl-1H-pyrazole-4-carbaldehyde (59.0 mg, 0.53 mmol) in 2 mL of DMF was added 28.6 mg of NaH (60%, 0.72 mmol) at 0° C. The resulting slurry was stirred at rt for 30 min and then was cooled to 0° C. To the resulting mixture was added a solution of the above intermediate (0.10 g, 0.36 mmol) in DMF (1 mL). The mixture was heated at 60° C. for 30 min and was quenched with MeOH. Solvent was removed in vacuo. Cold water was added and solid precipitate was filtered to give the desired Intermediate 1 as a yellow solid (0.11 g, 87%); MS (ESI) m/z 355.2 [M+H]⁺.

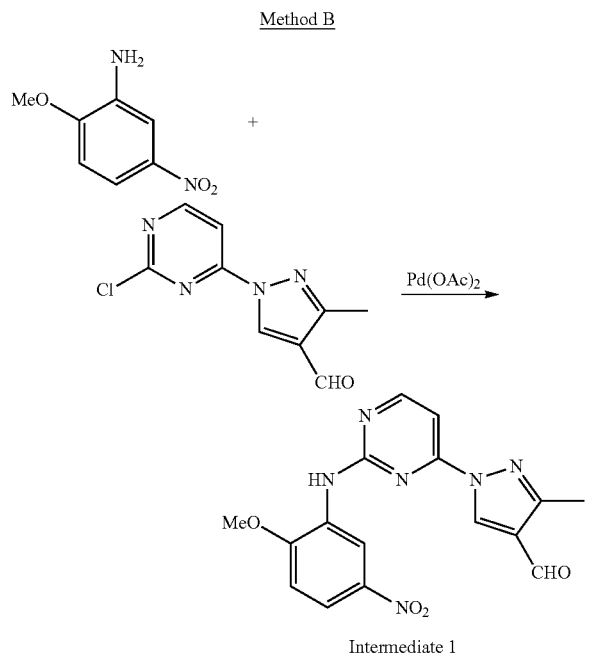

Method B

Intermediate 1

1-(2-Chloropyrimidin-4-yl)-3-methyl-1H-pyrazole-4-carbaldehyde (130 mg, 0.59 mmol) was added to a mixture of 2-methoxy-5-nitroaniline (88.6 mg, 0.53 mmol), Pd(OAc)₂ (6.5 mmol, 0.029 mmol), (±)-2,2'-bis(diphenylphosphino)-1,1'-binaphthalene (BINAP, 36.5 mg, 0.059 mmol), K₂CO₃ (161.8 mg, 1.17 mmol) in 10 mL of 1,4-dioxane (degassed for 20 min prior to use). 1-(2-Chloropyrimidin-4-yl)-3-methyl-1H-pyrazole-4-carbaldehyde was prepared by the known procedure as described in WO 2013/109882 A1. The resulting mixture was stirred at 100° C. for 5 h and then concentrated in vacuo. Cold water was added and the precipitated solid was collected by filtration, washed with DCM (5 mL) and dried to give the desired Intermediate 1 as a yellow solid (0.13 g, 65%); MS (ESI) m/z 355.4 [M+H]⁺.

Intermediate 2: 3-methyl-1-(2-(3-nitrophenylamino)pyrimidin-4-yl)-1H-pyrazole-4-carbaldehyde Using N-(3-nitrophenyl)formamide, Intermediate 2 was prepared as described in Method A; MS (ESI) m/z 325.2 [M+H]⁺.

Intermediate 3: 3-methyl-1-(2-(3-methyl-5-nitrophenylamino)pyrimidin-4-yl)-1H-pyrazole-4-carbaldehyde Using N-(3-methyl-5-nitrophenyl)formamide, Intermediate 3 was prepared as described in Method A; MS (ESI) m/z 339.1 [M+H]⁺.

Intermediate 4: 3-isopropyl-1-(2-(2-methoxy-4-morpholino-5-nitrophenylamino)-5-methylpyrimidin-4-yl)-1H-pyrazole-4-carbaldehyde Using N-(2-methoxy-4-morpholino-5-nitrophenyl)formamide and 3-isopropyl-1H-pyrazole-4-carbaldehyde, Intermediate 4 was prepared as described in Method A; MS (ESI) m/z 482. [M+H]⁺.

Intermediate 5: 1-(2-(2-methoxy-5-nitrophenylamino)-5-methylpyrimidin-4-yl)-3-methyl-1H-pyrazole-4-carbaldehyde Using 2-methoxy-5-nitroaniline and 1-(2-chloro-5-methylpyrimidin-4-yl)-3-methyl-1H-pyrazole-4-carbaldehyde, Intermediate 5 was prepared as described in Method B; MS (ESI) m/z 369.1 [M+H]⁺.

Intermediate 6: N-(2-methoxy-5-nitrophenyl)-4-(3-methyl-1H-pyrazol-1-yl)pyrimidin-2-amine Using 3-methyl-1H-pyrazole, Intermediate 6 was prepared as described in Method A; MS (ESI) m/z 327.1 [M+H]⁺.

Intermediate 7: 3-methyl-1-(5-methyl-2-(3-methyl-5-nitrophenylamino)pyrimidin-4-yl)-1H-pyrazole-4-carbaldehyde Using 3-methyl-5-nitroaniline and 1-(2-chloro-5-methylpyrimidin-4-yl)-3-methyl-1H-pyrazole-4-carbaldehyde, Intermediate 7 was prepared as described in Method B; MS (ESI) m/z 353.1 [M+H]⁺.

Intermediate 8: 1-(2-(2-methoxy-5-nitrophenylamino)-5-methylpyrimidin-4-yl)-1H-pyrazole-4-carbaldehyde Using 2-methoxy-5-nitroaniline and 1-(2-chloro-5-methylpyrimidin-4-yl)-1H-pyrazole-4-carbaldehyde, Intermediate 8 was prepared as described in Method B; MS (ESI) m/z 355.1 [M+H]⁺.

Intermediate 9: 1-(2-(4-fluoro-3-nitrophenylamino)pyrimidin-4-yl)-3-methyl-1H-pyrazole-4-carbaldehyde Using 4-fluoro-3-nitroaniline and 1-(2-chloropyrimidin-4-yl)-3-methyl-1H-pyrazole-4-carbaldehyde, Intermediate 9 was prepared as described in Method B; MS (ESI) m/z 343.1 [M+H]⁺.

Intermediate 10: 3-methyl-1-(2-(4-morpholino-3-nitrophenylamino)pyrimidin-4-yl)-1H-pyrazole-4-carbaldehyde To a solution of Intermediate 9 (200 mg, 0.59 mmol), DIPEA (0.20 mL, 1.17 mmol) in DMAA (10 mL) was added morpholine (0.076 mL, 0.88 mmol). The reaction mixture was heated to 80° C. for 2 h. Solvent was removed in vacuo and the mixture was extracted with DCM. The crude mixture was purified by column chromatography (0 to 5% MeOH in DCM) to give the desired intermediate as a red solid (220.2 mg, 92%); MS (ESI) m/z 410.2 [M+H]+.

Intermediate 11: 1-(2-(4-(4-acetylpiperazin-1-yl)-3-nitrophenylamino)pyrimidin-4-yl)-3-methyl-1H-pyrazole-4-carbaldehyde Using 1-(piperazin-1-yl)ethanone, Intermediate 11 was prepared as described in the preparation of Intermediate 10; MS (ESI) m/z 451.2 [M+H]+.

Intermediate 12: 1-(2-(4-fluoro-2-methoxy-5-nitrophenylamino)pyrimidin-4-yl)-3-methyl-1H-pyrazole-4-carbaldehyde Using 4-fluoro-2-methoxy-5-nitroaniline and 1-(2-chloropyrimidin-4-yl)-3-methyl-1H-pyrazole-4-carbaldehyde, Intermediate 12 was prepared as described in Method B; MS (ESI) m/z 373.1 [M+H]+.

Intermediate 13: 1-(2-(2-methoxy-4-morpholino-5-nitrophenylamino)pyrimidin-4-yl)-3-methyl-1H-pyrazole-4-carbaldehyde Using Intermediate 12, Intermediate 13 was prepared as described in the preparation of Intermediate 10; MS (ESI) m/z 440.2 [M+H]+.

Intermediate 14: 1-(2-(4-((2-(dimethylamino)ethyl)(methyl)amino)-2-methoxy-5-nitrophenylamino)pyrimidin-4-yl)-3-methyl-1H-pyrazole-4-carbaldehyde Using Intermediate 12, Intermediate 14 was prepared as described in the preparation of Intermediate 10; MS (ESI) m/z 455.2 [M+H]+.

Intermediate 15: 1-(2-(2-methoxy-4-(4-methylpiperazin-1-yl)-5-nitrophenylamino)pyrimidin-4-yl)-3-methyl-1H-pyrazole-4-carbaldehyde Using Intermediate 12, Intermediate 15 was prepared as described in the preparation of Intermediate 10; MS (ESI) m/z 453.2 [M+H]+.

Intermediate 16: 1-(2-(2-methoxy-5-nitro-4-(piperidin-1-yl)phenylamino)pyrimidin-4-yl)-3-methyl-1H-pyrazole-4-carbaldehyde Using Intermediate 12, Intermediate 16 was prepared as described in the preparation of Intermediate 10; MS (ESI) m/z 438.2 [M+H]+.

Intermediate 17: 1-(2-(4-fluoro-2-methoxy-5-nitrophenylamino)-5-methylpyrimidin-4-yl)-1H-pyrazole-4-carbaldehyde Using 4-fluoro-2-methoxy-5-nitroaniline and 1-(2-chloro-5-methylpyrimidin-4-yl)-1H-pyrazole-4-carbaldehyde, Intermediate 17 was prepared as described in Method B; MS (ESI) m/z 373.1 [M+H]+.

Intermediate 18: 1-(2-(2-methoxy-4-morpholino-5-nitrophenylamino)-5-methylpyrimidin-4-yl)-1H-pyrazole-4-carbaldehyde Using Intermediate 17, Intermediate 18 was prepared as described in the preparation of Intermediate 10; MS (ESI) m/z 440.2 [M+H]+.

Intermediate 19: 1-(2-(4-fluoro-2-methoxy-5-nitrophenylamino)-5-methylpyrimidin-4-yl)-3-methyl-1H-pyrazole-4-carbaldehyde Using 4-fluoro-2-methoxy-5-nitroaniline and 1-(2-chloro-5-methylpyrimidin-4-yl)-3-methyl-1H-pyrazole-4-carbaldehyde, Intermediate 19 was prepared as described in Method B; MS (ESI) m/z 387.1 [M+H]+.

Intermediate 20: 1-(2-(2-methoxy-4-morpholino-5-nitrophenylamino)-5-methylpyrimidin-4-yl)-3-methyl-1H-pyrazole-4-carbaldehyde Using Intermediate 19, Intermediate 20 was prepared as described in the preparation of Intermediate 10; MS (ESI) m/z 454.2 [M+H]+.

Intermediate 21: 1-(2-(2-methoxy-4-(4-methylpiperazin-1-yl)-5-nitrophenylamino)-5-methylpyrimidin-4-yl)-3-methyl-1H-pyrazole-4-carbaldehyde Using Intermediate 19, Intermediate 21 was prepared as described in the preparation of Intermediate 10; MS (ESI) m/z 467.2 [M+H]+.

Intermediate 22: 1-(2-(2-methoxy-5-nitro-4-(piperidin-1-yl)phenylamino)-5-methylpyrimidin-4-yl)-3-methyl-1H-pyrazole-4-carbaldehyde Using Intermediate 19, Intermediate 22 was prepared as described in the preparation of Intermediate 10; MS (ESI) m/z 452.2 [M+H]+.

Intermediate 23: 1-(2-(4-((2-(dimethylamino)ethyl)(methyl)amino)-2-methoxy-5-nitrophenylamino)-5-methylpyrimidin-4-yl)-3-methyl-1H-pyrazole-4-carbaldehyde Using Intermediate 19, Intermediate 23 was prepared as described in the preparation of Intermediate 10; MS (ESI) m/z 469.2 [M+H]+.

Intermediate 24: 1-(2-(2-methoxy-4-(4-methylpiperazin-1-yl)-5-nitrophenylamino)-5-methylpyrimidin-4-yl)-1H-pyrazole-4-carbaldehyde Using Intermediate 17, Intermediate 24 was prepared as described in the preparation of Intermediate 10; MS (ESI) m/z 453.2 [M+H]+.

Intermediate 25: 1-(2-(4-fluoro-2-methoxy-5-nitrophenylamino)pyrimidin-4-yl)-1H-pyrazole-4-carbaldehyde Using 4-fluoro-2-methoxy-5-nitroaniline and 1-(2-chloropyrimidin-4-yl)-1H-pyrazole-4-carbaldehyde, Intermediate 25 was prepared as described in Method B; MS (ESI) m/z 359.1 [M+H]+.

Intermediate 26: 1-(2-(2-methoxy-4-morpholino-5-nitrophenylamino)pyrimidin-4-yl)-1H-pyrazole-4-carbaldehyde Using Intermediate 25, Intermediate 26 was prepared as described in the preparation of Intermediate 10; MS (ESI) m/z 426.1 [M+H]+.

Intermediate 27: 1-(2-(4-(4-acetylpiperazin-1-yl)-2-methoxy-5-nitrophenylamino)-5-methylpyrimidin-4-yl)-1H-pyrazole-4-carbaldehyde Using Intermediate 17, Intermediate 27 was prepared as described in the preparation of Intermediate 10; MS (ESI) m/z 481.2 [M+H]$^+$.

Intermediate 28: 1-(2-(4-(dimethylamino)-2-methoxy-5-nitrophenylamino)pyrimidin-4-yl)-1H-pyrazole-4-carbaldehyde Using Intermediate 25, Intermediate 28 was prepared as described in the preparation of Intermediate 10; MS (ESI) m/z 384.1 [M+H]$^+$.

Intermediate 29: 1-(2-(2-methoxy-5-nitro-4-(1,4-oxazepan-4-yl)phenylamino)-5-methylpyrimidin-4-yl)-1H-pyrazole-4-carbaldehyde Using Intermediate 17, Intermediate 29 was prepared as described in the preparation of Intermediate 10; MS (ESI) m/z 454.2 [M+H]$^+$.

Intermediate 30: 1-(2-(2-methoxy-4-(4-methyl-1,4-diazepan-1-yl)-5-nitrophenylamino)-5-methylpyrimidin-4-yl)-1H-pyrazole-4-carbaldehyde Using Intermediate 17, Intermediate 30 was prepared as described in the preparation of Intermediate 10; MS (ESI) m/z 467.2 [M+H]$^+$.

Intermediate 31: 1-(2-(4-((2-(dimethylamino)ethyl)(methyl)amino)-2-methoxy-5-nitrophenylamino)-5-methylpyrimidin-4-yl)-1H-pyrazole-4-carbaldehyde Using Intermediate 17, Intermediate 31 was prepared as described in the preparation of Intermediate 10; MS (ESI) m/z 455.2 [M+H]$^+$.

Intermediate 32: 1-(2-(4-fluoro-2-methoxy-5-nitrophenylamino)-5-methylpyrimidin-4-yl)-4-methyl-1H-pyrrole-3-carbaldehyde Using 4-fluoro-2-methoxy-5-nitroaniline and 1-(2-chloro-5-methylpyrimidin-4-yl)-4-methyl-1H-pyrrole-3-carbaldehyde, Intermediate 32 was prepared as described in Method B; MS (ESI) m/z 386.1 [M+H]$^+$.

Intermediate 33: 1-(2-(2-methoxy-4-morpholino-5-nitrophenylamino)-5-methylpyrimidin-4-yl)-4-methyl-1H-pyrrole-3-carbaldehyde Using Intermediate 32, intermediate 33 was prepared as described in the preparation of Intermediate 10; MS (ESI) m/z 455.2 [M+H]$^+$.

Intermediate 34: 1-(5-chloro-2-(4-fluoro-2-methoxy-5-nitrophenylamino)pyrimidin-4-yl)-3-methyl-1H-pyrazole-4-carbaldehyde Using 4-fluoro-2-methoxy-5-nitroaniline and 1-(2,5-dichloropyrimidin-4-yl)-3-methyl-1H-pyrazole-4-carbaldehyde, Intermediate 34 was prepared as described in Method B; MS (ESI) m/z 407.1 [M+H]$^+$.

Intermediate 35: 1-(5-chloro-2-(2-methoxy-4-morpholino-5-nitrophenylamino)pyrimidin-4-yl)-3-methyl-1H-pyrazole-4-carbaldehyde Using Intermediate 34, Intermediate 35 was prepared as described in the preparation of Intermediate 10; MS (ESI) m/z 474.1 [M+H]$^+$.

Intermediate 36: 1-(2-(2-methoxy-5-nitro-4-(1H-pyrazol-1-yl)phenylamino)pyrimidin-4-yl)-3-methyl-1H-pyrazole-4-carbaldehyde

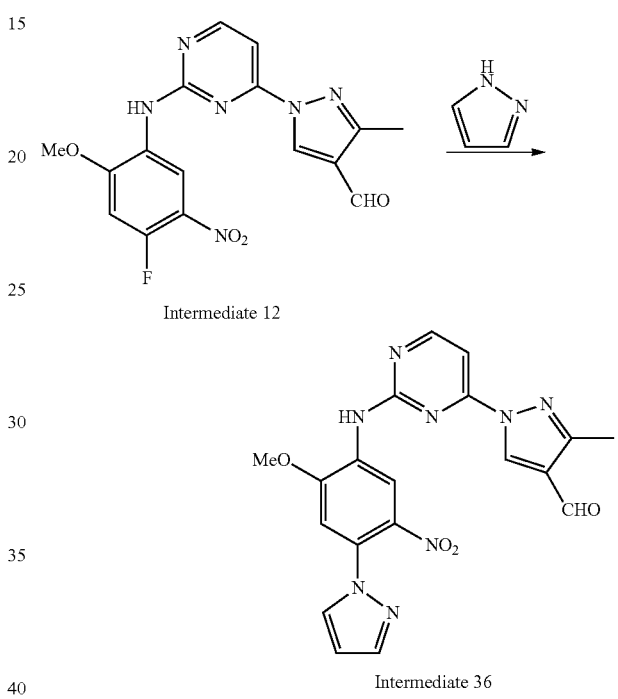

Intermediate 12

Intermediate 36

To a solution of Intermediate 12 (350 mg, 0.94 mmol), pyrazole (96.0 mg, 1.41 mmol) in DMAA (10 mL) was added cesium carbonate (612.5 mg, 1.88 mmol). The reaction mixture was heated at 80° C. for 16 h. Solvent was removed in vacuo and the mixture was extracted with DCM. The crude mixture was purified by column chromatography (0 to 5% MeOH in DCM) to give Intermediate 36 as a red solid (315.9 mg, 80%); MS (ESI) m/z 421.1 [M+H]$^+$.

Intermediate 37: 1-(5-chloro-2-(2-methoxy-4-(4-methylpiperazin-1-yl)-5-nitrophenylamino)pyrimidin-4-yl)-3-methyl-1H-pyrazole-4-carbaldehyde Using Intermediate 34, Intermediate 37 was prepared as described in the preparation of Intermediate 10; MS (ESI) m/z 487.2 [M+H]$^+$.

Intermediate 38: 3-cyclopropyl-1-(2-(4-fluoro-2-methoxy-5-nitrophenylamino)pyrimidin-4-yl)-1H-pyrazole-4-carbaldehyde Using 4-fluoro-2-methoxy-5-nitroaniline and 1-(2-chloropyrimidin-4-yl)-3-cyclopropyl-1H-pyrazole-4-carbaldehyde, Intermediate 38 was prepared as described in Method B; MS (ESI) m/z 399.1 [M+H]$^+$.

Intermediate 39: 3-cyclopropyl-1-(2-(2-methoxy-4-morpholino-5-nitrophenylamino)pyrimidin-4-yl)-1H-pyrazole-4-carbaldehyde Using Intermediate 38, Intermediate 39 was prepared as described in the preparation of Intermediate 10; MS (ESI) m/z 466.2 [M+H]+.

Intermediate 40: N-(3-(1-methyl-1H-pyrazol-4-yl)-5-nitrophenyl)formamide

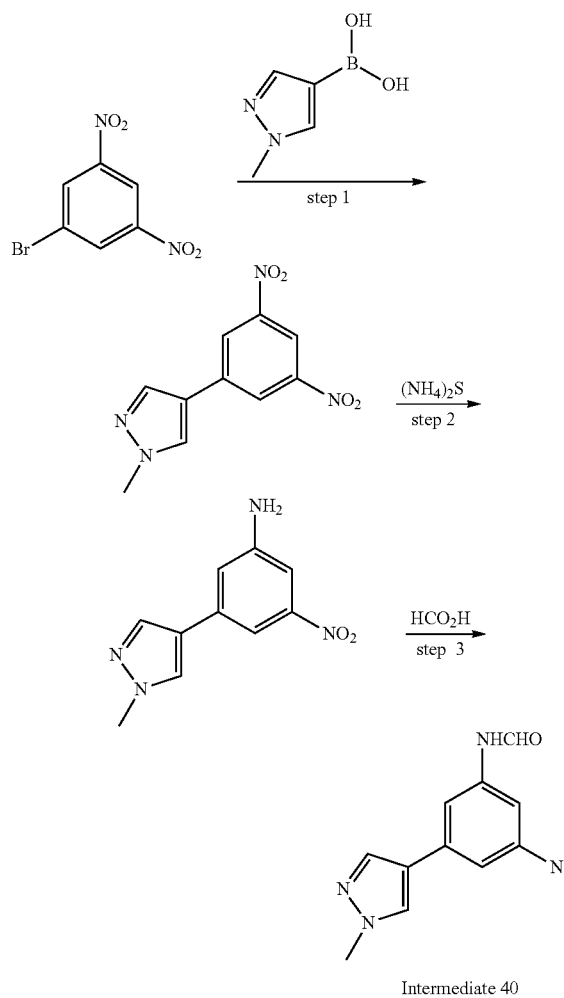

Intermediate 40

Step 1

To a solution of 5-bromo-1,3-dinitrobenzene (0.25 g, 1.01 mmol) in 10 mL dimethoxyethane was added 1-methyl-1H-pyrazole-4-boronic acid (0.14 g, 1.11 mmol), [1,1'-Bis(diphenylphosphino)ferrocene]dichloropalladium(II) (41 mg, 0.05 mmol) and 1M $Na_2CO_3$ (2.5 mL). The reaction mixture was heated at 80° C. for 16 h. The reaction mixture was, diluted with ethyl acetate, washed with sat. $NaHCO_3$ solution, brine, dried over $Na_2SO_4$, concentrated in vacuo and then purified by column chromatography (0-50% ethyl acetate in hexane) to give 0.16 g of the title compound as yellow solid; MS (ESI) m/z 249.1 [M+H]+.

Step 2

To a mixture of dinitro compound above (0.16 g, 0.65 mmol) in ethanol (3 mL) was added ammonium sulfide (0.5 mL). The reaction was heated at 90° C. for 2 h. Reaction mixture cooled to room temperature followed by addition of water. The precipitated solid was filtered, washed with ethanol and water, then dried to give 0.13 g of amino compound; MS (ESI) m/z 219.1 [M+H]+.

Step 3

To a solution of amino compound (60 mg, 0.27 mmoles) in acetonitrile (10 mL) was added formic acid (0.2 mL). The reaction mixture was heated at 80° C. overnight. Reaction mixture was concentrated in vacuo and residue was diluted with water. Precipitated solid (40 mg) was filtered and used directly for next step; MS (ESI) m/z 247.1 [M+H]+.

Intermediate 41: 3-methyl-1-(2-(3-(1-methyl-1H-pyrazol-4-yl)-5-nitrophenylamino)pyrimidin-4-yl)-1H-pyrazole-4-carbaldehyde Using Intermediate 40, Intermediate 41 was prepared as described in Method A; MS (ESI) m/z 405.1 [M+H]+.

Intermediate 42: N-(2-methoxy-4-(1-methyl-1H-pyrazol-4-yl)-5-nitrophenyl)formamide

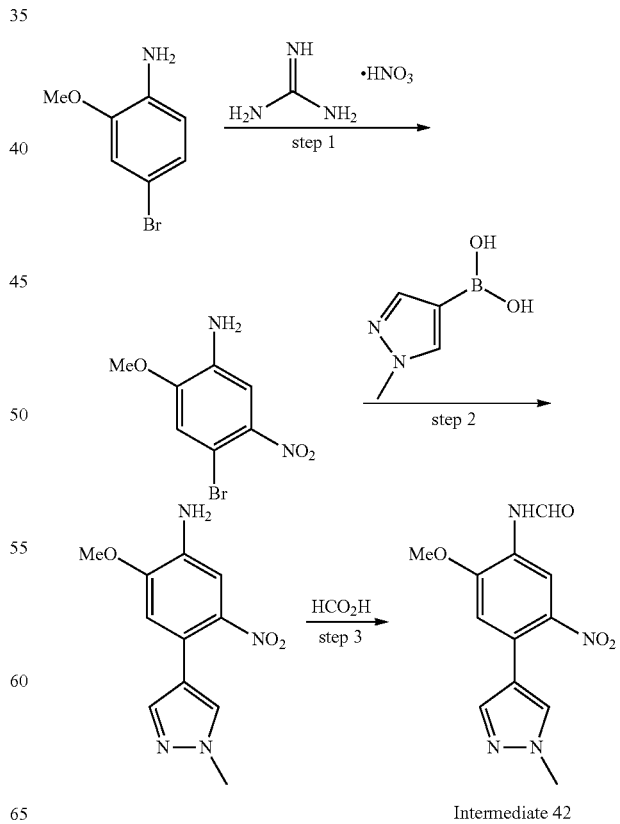

Intermediate 42

Step 1

Guanidine nitrate (1.22 g, 10.00 mmol) was added portionwise to a cooled mixture of 4-bromo-2-methoxyaniline (2.02 g, 10.00 mmol) in 85% sulfuric acid (15.68 mL, 250.00 mmol). The resulting blue mixture was stirred for 45 min at 0° C. and was slowly poured over a well-stirred mixture of 1N NaOH (40 mL) and ice (120 g). The aqueous layer was extracted with ethyl acetate and the organic layer was concentrated in vacuo. Purified by column chromatography (0-40% ethyl acetate in hexane) to give 1.20 g of 4-bromo-2-methoxy-5-nitrobenzenamine; MS (ESI) m/z 247.0 [M+H]$^+$.

Step 2

To a solution of 4-bromo-2-methoxy-5-nitroaniline (0.25 g, 1.01 mmol) in 10 mL of 1,4-dioxane was added 1-methyl-1H-pyrazole-4-boronic acid (0.14 g, 1.11 mmol), [1,1'-Bis(diphenylphosphino)ferrocene]dichloropalladium(II) (41 mg, 0.05 mmol) and 1M Na$_2$CO$_3$ (2.5 mL). The reaction mixture was heated at 80° C. for 16 h. The reaction mixture was diluted with ethyl acetate, washed with sat. NaHCO$_3$ solution, brine, dried over Na$_2$SO$_4$, concentrated in vacuo and then purified by column chromatography (0-50% ethyl acetate in hexane) to give the title compound; MS (ESI) m/z 259.1 [M+H]$^+$.

Step 3

To a solution of 4-pyrazoloamino compound (0.16 g, 0.65 mmol) in acetonitrile (16 mL) was added formic acid (0.7 mL). The reaction mixture was heated to 80° C. for 16 h. Reaction mixture was concentrated in vacuo and the resulting residue was diluted with water. Precipitated solid (0.14 g) was filtered and used directly for next step; MS (ESI) m/z 277.1 [M+H]$^+$.

Intermediate 43: 1-(2-(2-methoxy-4-(1-methyl-1H-pyrazol-4-yl)-5-nitrophenylamino)pyrimidin-4-yl)-3-methyl-1H-pyrazole-4-carbaldehyde Using Intermediate 42, Intermediate 43 was prepared as described in Method A; MS (ESI) m/z 435.2 [M+H]$^+$.

Intermediate 44: N-(2-methoxy-4-(1-methyl-1,2,3,6-tetrahydropyridin-4-yl)-5-nitrophenyl)formamide Using 1-(tert-butoxycarbonyl)-1,2,3,6-tetrahydropyridin-4-ylboronic acid, Intermediate 44 was prepared as described in the preparation of Intermediate 42; MS (ESI) m/z 292.1 [M+H]$^+$.

Intermediate 45: 1-(2-(2-methoxy-4-(1-methyl-1,2,3,6-tetrahydropyridin-4-yl)-5-nitrophenylamino)pyrimidin-4-yl)-3-methyl-1H-pyrazole-4-carbaldehyde Using Intermediate 44, Intermediate 45 was prepared as described in Method A; MS (ESI) m/z 450.2 [M+H]$^+$.

Intermediate 46: 2-methoxy-4-morpholino-5-nitroaniline

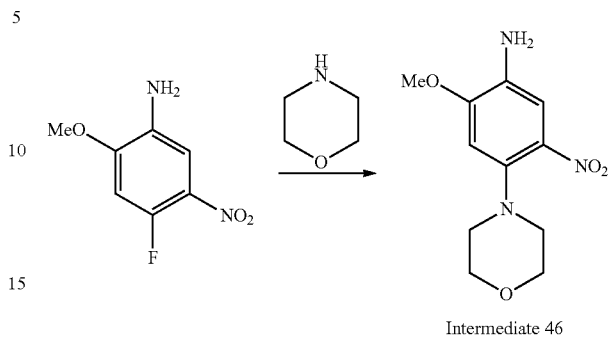

Intermediate 46

Using 4-fluoro-2-methoxy-5-nitroaniline, Intermediate 46 was prepared as described in the preparation of Intermediate 10; MS (ESI) m/z 254.1 [M+H]$^+$.

Intermediate 47: 1-(5-fluoro-2-(2-methoxy-4-morpholino-5-nitrophenylamino)pyrimidin-4-yl)-4-methyl-1H-pyrrole-3-carbaldehyde Using 1-(2-chloro-5-fluoropyrimidin-4-yl)-4-methyl-1H-pyrrole-3-carbaldehyde and Intermediate 46, Intermediate 47 was prepared as described in Method B; MS (ESI) m/z 457.2 [M+H]$^+$.

Intermediate 48: 1-(5-fluoro-2-(2-methoxy-4-morpholino-5-nitrophenylamino)pyrimidin-4-yl)-3-methyl-1H-pyrazole-4-carbaldehyde Using 1-(2-chloro-5-fluoropyrimidin-4-yl)-3-methyl-1H-pyrazole-4-carbaldehyde and Intermediate 46, Intermediate 48 was prepared as described in Method B; MS (ESI) m/z 458.2 [M+H]$^+$.

Intermediate 49: 1-(2-(4-fluoro-2-isopropoxy-5-nitrophenylamino)-5-methylpyrimidin-4-yl)-1H-pyrazole-4-carbaldehyde Using 4-fluoro-2-isopropoxy-5-nitroaniline and 1-(2-chloro-5-methylpyrimidin-4-yl)-1H-pyrazole-4-carbaldehyde, Intermediate 49 was prepared as described in Method B; MS (ESI) m/z 401.1 [M+H]$^+$.

Intermediate 50: 1-(2-(2-isopropoxy-4-morpholino-5-nitrophenylamino)-5-methylpyrimidin-4-yl)-1H-pyrazole-4-carbaldehyde Using Intermediate 49, Intermediate 50 was prepared as described in the preparation of Intermediate 10; MS (ESI) m/z 468.2 [M+H]$^+$.

Intermediate 51: 1-(2-(2-methoxy-4-(1-methyl-1,2,3,6-tetrahydropyridin-4-yl)-5-nitrophenylamino)-5-methylpyrimidin-4-yl)-1H-pyrazole-4-carbaldehyde Using Intermediate 44, Intermediate 51 was prepared as described in Method A; MS (ESI) m/z 450.2 [M+H]$^+$.

Intermediate 52:
5-methoxy-2-nitrobiphenyl-4-amine

Using benzene boronic acid and 4-bromo-2-methoxy-5-nitroaniline, Intermediate 52 was prepared as described in the preparation of Intermediate 42; MS (ESI) m/z 245.1 [M+H]$^+$.

Intermediate 53: 1-(2-(5-methoxy-2-nitrobiphenyl-4-ylamino)pyrimidin-4-yl)-3-methyl-1H-pyrazole-4-carbaldehyde Using Intermediate 52, Intermediate 53 was prepared as described in Method B; MS (ESI) m/z 431.1 [M+H]$^+$.

Intermediate 54: (1-(2-(2-methoxy-4-morpholino-5-nitrophenylamino)pyrimidin-4-yl)-3-methyl-1H-pyrazol-4-yl)methanol Using Intermediate 46 and (1-(2-(chloropyrimidin-4-yl)-3-methyl-1H-pyrazol-4-yl)methanol, Intermediate 54 was prepared as described in Method B; MS (ESI) m/z 442.2 [M+H]$^+$.

Intermediate 55: 3-tert-butyl-1-(2-(4-fluoro-2-methoxy-5-nitrophenylamino)-5-methylpyrimidin-4-yl)-1H-pyrazole-4-carbaldehyde Using 4-fluoro-2-methoxy-5-nitroaniline and 3-tert-butyl-1H-pyrazol-4-carbaldehyde, Intermediate 55 was prepared as described in Method B; MS (ESI) m/z 429.2 [M+H]$^+$.

Intermediate 56:
2',5-dimethoxy-2-nitrobiphenyl-4-amine

Using 2-methoxyphenylboronic acid and 4-bromo-2-methoxy-5-nitroaniline, Intermediate 56 was prepared as described in Intermediate 42; MS (ESI) m/z 275.1 [M+H]$^+$.

Intermediate 57: 1-(2-(2',5-dimethoxy-2-nitrobiphenyl-4-ylamino)pyrimidin-4-yl)-3-methyl-1H-pyrazole-4-carbaldehyde Using Intermediate 56, Intermediate 57 was prepared as described in Method B; MS (ESI) m/z 461.2 [M+H]$^+$.

Intermediate 58: 4-(4,4-difluoropiperidin-1-yl)-2-methoxy-5-nitroaniline

Using 4-fluoro-2-methoxy-5-nitroaniline and 4,4-difluoropiperidine, Intermediate 58 was prepared as described in the preparation of Intermediate 10; MS (ESI) m/z 288.1 [M+H]$^+$.

Intermediate 59: 1-(2-(4-(4,4-difluoropiperidin-1-yl)-2-methoxy-5-nitrophenylamino)pyrimidin-4-yl)-3-methyl-1H-pyrazole-4-carbaldehyde Using Intermediate 58, Intermediate 59 was prepared as described in Method B; MS (ESI) m/z 474.2 [M+H]$^+$.

Intermediate 60: 1-(2-(4-fluoro-2-methoxy-5-nitrophenylamino)pyrimidin-4-yl)-3,5-dimethyl-1H-pyrazole-4-carbaldehyde Using 4-fluoro-2-methoxy-5-nitroaniline and 1-(2-chloropyrimidin-4-yl)-3,5-dimethyl-1H-pyrazole-4-carbaldehyde, Intermediate 60 was prepared as described in Method B; MS (ESI) m/z 387.1 [M+H]$^+$.

Intermediate 61: 1-(2-(2-methoxy-4-morpholino-5-nitrophenylamino)pyrimidin-4-yl)-3,5-dimethyl-1H-pyrazole-4-carbaldehyde Using Intermediate 60, Intermediate 61 was prepared as described in the preparation of Intermediate 10; MS (ESI) m/z 454.2 [M+H]$^+$.

Intermediate 62: 1-(2-(4-(dimethylamino)-2-methoxy-5-nitrophenylamino)pyrimidin-4-yl)-3-methyl-1H-pyrazole-4-carbaldehyde Using Intermediate 12, Intermediate 62 was prepared as described in the preparation of Intermediate 10; MS (ESI) m/z 398.2 [M+H]$^+$.

Intermediate 63: 1-(2-(4-fluoro-2-methoxy-5-nitrophenylamino)pyrimidin-4-yl)-3-phenyl-1H-pyrazole-4-carbaldehyde Using 4-fluoro-2-methoxy-5-nitroaniline and 1-(2-chloropyrimidin-4-yl)-3-phenyl-1H-pyrazole-4-carbaldehyde, Intermediate 63 was prepared as described in Method B; MS (ESI) m/z 435.1 [M+H]$^+$.

Intermediate 64: 1-(2-(2-methoxy-4-morpholino-5-nitrophenylamino)pyrimidin-4-yl)-3-phenyl-1H-pyrazole-4-carbaldehyde Using Intermediate 63, Intermediate 64 was prepared as described in the preparation of Intermediate 10; MS (ESI) m/z 502.2 [M+H]$^+$.

Intermediate 65: 1-(5-chloro-2-(4-fluoro-2-methoxy-5-nitrophenylamino)pyrimidin-4-yl)-1H-pyrazole-4-carbaldehyde Using 4-fluoro-2-methoxy-5-nitroaniline and 1-(2,5-dichloropyrimidin-4-yl)-1H-pyrazole-4-carbaldehyde, Intermediate 65 was prepared as described in Method B; MS (ESI) m/z 393.0 [M+H]$^+$.

Intermediate 66: 1-(5-chloro-2-(2-methoxy-4-morpholino-5-nitrophenylamino)pyrimidin-4-yl)-1H-pyrazole-4-carbaldehyde Using Intermediate 65, Intermediate 66 was prepared as described in the preparation of Intermediate 10; MS (ESI) m/z 460.1 [M+H]$^+$.

Intermediate 67: 1 (2 (4 (4 (2 fluoroethyl)piperazin-1-yl)-2-methoxy-5-nitrophenylamino)pyrimidin-4-yl)-3-methyl-1H-pyrazole-4-carbaldehyde Using Intermediate 12 and 1-(2-fluoroethyl)piperazine hydrochloride, Intermediate 67 was prepared as described in the preparation of Intermediate 10; MS (ESI) m/z 485.2 [M+H]$^+$.

Intermediate 68: 1-(2-(4-fluoro-2-methoxy-5-nitrophenylamino)pyrimidin-4-yl)-3-p-tolyl-1H-pyrazole-4-carbaldehyde Using 4-fluoro-2-methoxy-5-nitroaniline and 1-(2-chloropyrimidin-4-yl)-3-p-tolyl-1H-pyrazole-4-carbaldehyde, Intermediate 68 was prepared as described in Method B; MS (ESI) m/z 449.1 [M+H]$^+$.

Intermediate 69: 1-(2-(2-methoxy-4-morpholino-5-nitrophenylamino)pyrimidin-4-yl)-3-p-tolyl-1H-pyrazole-4-carbaldehyde Using Intermediate 68, Intermediate 69 was prepared as described in the preparation of Intermediate 10; MS (ESI) m/z 516.2 [M+H]$^+$.

Intermediate 70: 1-(2-(4-fluoro-2-methoxy-5-nitrophenylamino)pyrimidin-4-yl)-3-(4-fluorophenyl)-1H-pyrazole-4-carbaldehyde Using 4-fluoro-2-methoxy-5-nitroaniline and 1-(2-chloropyrimidin-4-yl)-3-(4-fluorophenyl)-1H-pyrazole-4-carbaldehyde, Intermediate 70 was prepared as described in Method B; MS (ESI) m/z 453.1 [M+H]$^+$.

Intermediate 71: 3-(4-fluorophenyl)-1-(2-(2-methoxy-4-morpholino-5-nitrophenylamino)pyrimidin-4-yl)-1H-pyrazole-4-carbaldehyde Using Intermediate 70, Intermediate 71 was prepared as described in the preparation of Intermediate 10; MS (ESI) m/z 520.2 [M+H]$^+$.

Intermediate 72: 3-tert-butyl-1-(2-(2-methoxy-4-morpholino-5-nitrophenylamino)-5-methylpyrimidin-4-yl)-1H-pyrazole-4-carbaldehyde Using Intermediate 55, Intermediate 72 was prepared as described in the preparation of Intermediate 10; MS (ESI) m/z 496.2 [M+H]$^+$.

Intermediate 73: 1-(2-(4-(dimethylamino)-2-methoxy-5-nitrophenylamino)pyrimidin-4-yl)-3-phenyl-1H-pyrazole-4-carbaldehyde Using Intermediate 63, Intermediate 73 was prepared as described in the preparation of Intermediate 10; MS (ESI) m/z 460.2 [M+H]$^+$.

Intermediate 74: 1-(2-(4-(azetidin-1-yl)-2-methoxy-5-nitrophenylamino)pyrimidin-4-yl)-3-phenyl-1H-pyrazole-4-carbaldehyde Using Intermediate 63, Intermediate 74 was prepared as described in the preparation of Intermediate 10; MS (ESI) m/z 472.2 [M+H]$^+$.

Intermediate 75: 2-chloro-4-(3-phenyl-1H-pyrazol-1-yl)pyrimidine

Using 2,4-dichloropyrimidine and 4 3-phenyl-1H-pyrazole, Intermediate 75 was prepared as described in WO 2013/109882; MS (ESI) m/z 257.1 [M+H]$^+$.

Intermediate 76: 2-methoxy-4-(4-methylpiperazin-1-yl)-5-nitroaniline

Using 4-fluoro-2-methoxy-5-nitroaniline, Intermediate 76 was prepared as described in the preparation of Intermediate 10; MS (ESI) m/z 267.1 [M+H]$^+$.

Intermediate 77: N-(2-methoxy-4-(4-methylpiperazin-1-yl)-5-nitrophenyl)-4-(3-phenyl-1H-pyrazol-1-yl)pyrimidin-2-amine Using Intermediate 75 and Intermediate 76, the Intermediate 77 was prepared as described in Method B; MS (ESI) m/z 487.2 [M+H]$^+$.

Intermediate 78: 3-tert-butyl-1-(2-(4-fluoro-2-methoxy-5-nitrophenylamino)pyrimidin-4-yl)-1H-pyrazole-4-carbaldehyde Using 4-fluoro-2-methoxy-5-nitroaniline and 3-tert-butyl-1H-pyrazol-4-carbaldehyde, Intermediate 78 was prepared as described in Method B; MS (ESI) m/z 415.2 [M+H]$^+$.

Intermediate 79: 3-tert-butyl-1-(2-(2-methoxy-4-morpholino-5-nitrophenylamino)pyrimidin-4-yl)-1H-pyrazole-4-carbaldehyde Using Intermediate 78, Intermediate 79 was prepared as described in the preparation of Intermediate 10; MS (ESI) m/z 482.2 [M+H]$^+$.

Intermediate 80: 1-(2-(2-methoxy-4-morpholino-5-nitrophenylamino)pyrimidin-4-yl)-3-(thiophen-2-yl)-1H-pyrazole-4-carbaldehyde Using N-(2-methoxy-4-morpholino-5-nitrophenyl)formamide and 3-(thiophen-2-yl)-1H-pyrazole-4-carbaldehyde, Intermediate 80 was prepared as described in Method A; MS (ESI) m/z 508.1 [M+H]$^+$.

Intermediate 81: 3-(2,5-dimethylphenyl)-1-(2-(4-fluoro-2-methoxy-5-nitrophenylamino)pyrimidin-4-yl)-1H-pyrazole-4-carbaldehyde Using 4-fluoro-2-methoxy-5-nitroaniline and 1-(2-chloropyrimidin-4-yl)-3-(2,5-dimethylphenyl)-1H-pyrazole-4-carbaldehyde, Intermediate 81 was prepared as described in Method B; MS (ESI) m/z 447.2 [M+H]$^+$.

Intermediate 82: 3-(2,5-dimethylphenyl)-1-(2-(2-methoxy-4-morpholino-5-nitrophenylamino)pyrimidin-4-yl)-1H-pyrazole-4-carbaldehyde Using Intermediate 81, Intermediate 82 was prepared as described in the preparation of Intermediate 10; MS (ESI) m/z 530.2 [M+H]$^+$.

Intermediate 83: (1-(2-(2-methoxy-4-morpholino-5-nitrophenylamino)pyrimidin-4-yl)-3-phenyl-1H-pyrazol-4-yl)methanol To a solution of Intermediate 64 (0.2 g, 0.40 mmol) in THF (5 mL) was added 4.0 mL of DIBAL (1M solution in toluene) at 0° C. The reaction mixture was heated at 50° C. for 16 h. Ice water was added into the reaction. Solvent was removed in vacuo and the resulting mixture was extracted with DCM, dried over NaSO$_4$. The desired intermediate was purified by column chromatography (0-20% MeOH in DCM) to give 0.16 g as a yellow solid; MS (ESI) m/z 474.2 [M+H]$^+$.

Intermediate 84: 3-isopropyl-1-(2-(2-methoxy-4-morpholino-5-nitrophenylamino)pyrimidin-4-yl)-1H-pyrazole-4-carbaldehyde Using N-(2-methoxy-4-morpholino-5-nitrophenyl)formamide and 3-isopropyl-1H-pyrazole-4-carbaldehyde, Intermediate 84 was prepared as described in Method A; MS (ESI) m/z 468.2 [M+H]$^+$.

Intermediate 85: 1-(2-(2-methoxy-4-((2-methoxyethyl)(methyl)amino)-5-nitrophenylamino)pyrimidin-4-yl)-3-phenyl-1H-pyrazole-4-carbaldehyde Using Intermediate 63, the Intermediate 85 was prepared as described in the preparation of Intermediate 10; MS (ESI) m/z 504.2 [M+H]$^+$.

Intermediate 86: 1-(2-(2-methoxy-4-(methyl(oxetan-3-yl)amino)-5-nitrophenylamino)pyrimidin-4-yl)-3-phenyl-1H-pyrazole-4-carbaldehyde Using Intermediate 63, Intermediate 86 was prepared as described in the preparation of Intermediate 10; MS (ESI) m/z 502.2 [M+H]$^+$.

Intermediate 87: 1-(2-(2-methoxy-5-nitro-4-(pyrrolidin-1-yl)phenylamino)pyrimidin-4-yl)-3-phenyl-1H-pyrazole-4-carbaldehyde Using Intermediate 63, Intermediate 87 was prepared as described in the preparation of Intermediate 10; MS (ESI) m/z 486.2 [M+H]$^+$.

Intermediate 88: 3-tert-butyl-1-(2-(2-methoxy-4-((2-methoxyethyl)(methyl)amino)-5-nitrophenylamino)pyrimidin-4-yl)-1H-pyrazole-4-carbaldehyde Using Intermediate 78, Intermediate 88 was prepared as described in the preparation of Intermediate 10; MS (ESI) m/z 484.2 [M+H]$^+$.

Intermediate 89: 3-tert-butyl-1-(2-(2-methoxy-4-(methyl(oxetan-3-yl)amino)-5-nitrophenylamino)pyrimidin-4-yl)-1H-pyrazole-4-carbaldehyde Using Intermediate 78, Intermediate 89 was prepared as described in the preparation of Intermediate 10; MS (ESI) m/z 482.2 [M+H]$^+$.

Intermediate 90: 3-tert-butyl-1-(2-(2-methoxy-5-nitro-4-(pyrrolidin-1-yl)phenylamino)pyrimidin-4-yl)-1H-pyrazole-4-carbaldehyde Using Intermediate 78, Intermediate 90 was prepared as described in the preparation of Intermediate 10; MS (ESI) m/z 466.2 [M+H]$^+$.

Intermediate 91: 3-cyclopropyl-1-(2-(2-methoxy-4-((2-methoxyethyl)(methyl)amino)-5-nitrophenylamino)pyrimidin-4-yl)-1H-pyrazole-4-carbaldehyde Using Intermediate 38, Intermediate 91 was prepared as described in the preparation of Intermediate 10; MS (ESI) m/z 468.2 [M+H]$^+$.

Intermediate 92: 3-cyclopropyl-1-(2-(2-methoxy-4-(methyl(oxetan-3-yl)amino)-5-nitrophenylamino)pyrimidin-4-yl)-1H-pyrazole-4-carbaldehyde Using Intermediate 38, Intermediate 92 was prepared as described in the preparation of Intermediate 10; MS (ESI) m/z 466.2 [M+H]$^+$.

Intermediate 93: 3-cyclopropyl-1-(2-(2-methoxy-5-nitro-4-(pyrrolidin-1-yl)phenylamino)pyrimidin-4-yl)-1H-pyrazole-4-carbaldehyde Using Intermediate 38, Intermediate 93 was prepared as described in the preparation of Intermediate 10; MS (ESI) m/z 450.2 [M+H]$^+$.

Intermediate 94: 3-isopropyl-1-(2-(2-methoxy-4-((2-methoxyethyl)(methyl)amino)-5-nitrophenylamino)pyrimidin-4-yl)-1H-pyrazole-4-carbaldehyde Using N-(2-methoxy-4-((2-methoxyethyl)(methyl)amino)-5-nitrophenyl)formamide and 3-isopropyl-1H-pyrazole-4-carbaldehyde, Intermediate 94 was prepared as described in Method A; MS (ESI) m/z 470.2 [M+H]$^+$.

Intermediate 95: 3-isopropyl-1-(2-(2-methoxy-4-(methyl(oxetan-3-yl)amino)-5-nitrophenylamino)pyrimidin-4-yl)-1H-pyrazole-4-carbaldehyde Using N-(2-methoxy-4-(methyl(oxetan-3-yl)amino)-5-nitrophenyl)formamide and 3-isopropyl-1H-pyrazole-4-carbaldehyde, Intermediate 95 was prepared as described in Method A; MS (ESI) m/z 468.2 [M+H]$^+$.

Intermediate 96: 3-isopropyl-1-(2-(2-methoxy-5-nitro-4-(pyrrolidin-1-yl)phenylamino)pyrimidin-4-yl)-1H-pyrazole-4-carbaldehyde Using N-(2-methoxy-5-nitro-4-(pyrrolidin-1-yl)phenyl)formamide and 3-isopropyl-1H-pyrazole-4-carbaldehyde, Intermediate 96 was prepared as described in Method A; MS (ESI) m/z 452.2 [M+H]$^+$.

Intermediate 97: 1-(2-(4-fluoro-2-methoxy-5-nitrophenylamino)-5-methylpyrimidin-4-yl)-3-phenyl-1H-pyrazole-4-carbaldehyde Using 4-fluoro-2-methoxy-5-nitroaniline and 1-(2-chloro-5-methylpyrimidin-4-yl)-3-phenyl-1H-pyrazole-4-carbaldehyde, Intermediate 97 was prepared as described in Method B; MS (ESI) m/z 449.1 [M+H]$^+$.

Intermediate 98: 1-(2-(2-methoxy-4-morpholino-5-nitrophenylamino)-5-methylpyrimidin-4-yl)-3-phenyl-1H-pyrazole-4-carbaldehyde Using Intermediate 97, Intermediate 98 was prepared as described in the preparation of Intermediate 10; MS (ESI) m/z 516.2 [M+H]$^+$.

Intermediate 99: 3-cyclopropyl-1-(2-(4-fluoro-2-methoxy-5-nitrophenylamino)-5-methylpyrimidin-4-yl)-1H-pyrazole-4-carbaldehyde Using 4-fluoro-2-methoxy-5-nitroaniline and 1-(2-chloro-5-methylpyrimidin-4-yl)-3-cyclopropyl-1H-pyrazole-4-carbaldehyde, Intermediate 99 was prepared as described in Method B; MS (ESI) m/z 413.1 [M+H]⁺.

Intermediate 100: 3-cyclopropyl-1-(2-(2-methoxy-4-morpholino-5-nitrophenylamino)-5-methylpyrimidin-4-yl)-1H-pyrazole-4-carbaldehyde Using Intermediate 99, Intermediate 100 was prepared as described in the preparation of Intermediate 10; MS (ESI) m/z 480.2 [M+H]⁺.

Intermediate 101: 3-tert-butyl-1-(2-(4-(ethyl(2-methoxyethyl)amino)-2-methoxy-5-nitrophenylamino)pyrimidin-4-yl)-1H-pyrazole-4-carbaldehyde Using Intermediate 78, Intermediate 101 was prepared as described in the preparation of Intermediate 10; MS (ESI) m/z 498.2 [M+H]⁺.

Intermediate 102: 3-(furan-3-yl)-1-(2-(2-methoxy-4-morpholino-5-nitrophenylamino)pyrimidin-4-yl)-1H-pyrazole-4-carbaldehyde Using N-(2-methoxy-4-morpholino-5-nitrophenyl)formamide and 3-(furan-3-yl)-1H-pyrazole-4-carbaldehyde, Intermediate 102 was prepared as described in Method A; MS (ESI) m/z 492.2 [M+H]⁺.

Intermediate 103: 1-(2-((2-methoxy-4-morpholino-5-nitrophenyl)amino)pyrimidin-4-yl)-3-(pyridine-3-yl)-1H-pyrazole-4-carbaldehyde Using N-(2-methoxy-4-morpholino-5-nitrophenyl)formamide and 4-(pyridin-3-yl)-1H-pyrazole-3-carbaldehyde, Intermediate 103 was prepared as described in Method A; MS (ESI) m/z 503.2 [M+H]⁺.

Intermediate 104: 1-(2-(4-(4-acetylpiperazin-1-yl)-2-methoxy-5-nitrophenylamino)pyrimidin-4-yl)-3-cyclopropyl-1H-pyrazole-4-carbaldehyde Using Intermediate 38, Intermediate 104 was prepared as described in the preparation of Intermediate 10; MS (ESI) m/z 507.2 [M+H]⁺.

Intermediate 105: 1-(5-fluoro-2-(2-methoxy-4-morpholino-5-nitrophenylamino)pyrimidin-4-yl)-4-(furan-3-yl)-1H-pyrrole-3-carbaldehyde Using N-(2-methoxy-4-morpholino-5-nitrophenyl)formamide and 4-(furan-3-yl)-1H-pyrrole-3-carbaldehyde, Intermediate 105 was prepared as described in Method A; MS (ESI) m/z 509.2 [M+H]⁺.

Intermediate 106: 3-cyclopropyl-1-(2-(2-methoxy-4-(methyl(oxetan-3-yl)amino)-5-nitrophenylamino)-5-methylpyrimidin-4-yl)-1H-pyrazole-4-carbaldehyde Using Intermediate 99, Intermediate 106 was prepared as described in the preparation of Intermediate 10; MS (ESI) m/z 480.2 [M+H]⁺.

Intermediate 107: 1-(2-(4-(4-acetylpiperazin-1-yl)-2-methoxy-5-nitrophenylamino)pyrimidin-4-yl)-3-phenyl-1H-pyrazole-4-carbaldehyde Using Intermediate 63, Intermediate 107 was prepared as described in the preparation of Intermediate 10; MS (ESI) m/z 543.2 [M+H]⁺.

Intermediate 108: 1-(2-(2-methoxy-4-morpholino-5-nitrophenylamino)pyrimidin-4-yl)-3-(pyridin-4-yl)-1H-pyrazole-4-carbaldehyde Using N-(2-methoxy-4-morpholino-5-nitrophenyl)formamide and 3-(pyridin-4-yl)-1H-pyrazole-4-carbaldehyde, Intermediate 108 was prepared as described in Method A; MS (ESI) m/z 503.2 [M+H]⁺.

Intermediate 109: 1-(2-(4-(azetidin-1-yl)-2-methoxy-5-nitrophenylamino)pyrimidin-4-yl)-3-cyclopropyl-1H-pyrazole-4-carbaldehyde Using Intermediate 38, Intermediate 109 was prepared as described in the preparation of Intermediate 10; MS (ESI) m/z 436.2 [M+H]⁺.

Intermediate 110: 1-(2-(4-(azetidin-1-yl)-2-methoxy-5-nitrophenylamino)-5-fluoropyrimidin-4-yl)-4-methyl-1H-pyrrole-3-carbaldehyde Using 1-(2-chloro-5-fluoropyrimidin-4-yl)-4-methyl-1H-pyrrole-3-carbaldehyde and 4-(azetidin-1-yl)-2-methoxy-5-nitrobenzenamine, Intermediate 110 was prepared as described in Method B; MS (ESI) m/z 427.2 [M+H]⁺.

Intermediate 111: 1-(2-(4-(dimethylamino)-2-methoxy-5-nitrophenylamino)-5-fluoropyrimidin-4-yl)-4-methyl-1H-pyrrole-3-carbaldehyde Using 1-(2-chloro-5-fluoropyrimidin-4-yl)-4-methyl-1H-pyrrole-3-carbaldehyde and 5-methoxy-$N^1$,$N^1$-dimethyl-2-nitrobenzene-1,4-diamine, Intermediate 111 was prepared as described in Method B; MS (ESI) m/z 415.2 [M+H]⁺.

Intermediate 112: 1-(5-fluoro-2-(4-fluoro-2-methoxy-5-nitrophenylamino)pyrimidin-4-yl)-4-(trifluoromethyl)-1H-pyrrole-3-carbaldehyde Using 1-(2-chloro-5-fluoropyrimidin-4-yl)-4-(trifluoromethyl)-1H-pyrrole-3-carbaldehyde and 4-fluoro-2-methoxy-5-nitroaniline, Intermediate 112 was prepared as described in Method B; MS (ESI) m/z 444.1 [M+H]⁺.

Intermediate 113: 1-(2-(4-((2-(dimethylamino)ethyl)(methyl)amino)-2-methoxy-5-nitrophenylamino)-5-fluoropyrimidin-4-yl)-4-(trifluoromethyl)-1H-pyrrole-3-carbaldehyde Using Intermediate 112, Intermediate 113 was prepared as described in the preparation of Intermediate 10; MS (ESI) m/z 523.2 [M+H]⁺.

Example 1

Compound 1: N-(3-(4-(4-(azetidin-1-ylmethyl)-3-methyl-1H-pyrazol-1-yl)pyrimidin-2-ylamino)-4-methoxyphenyl)acrylamide

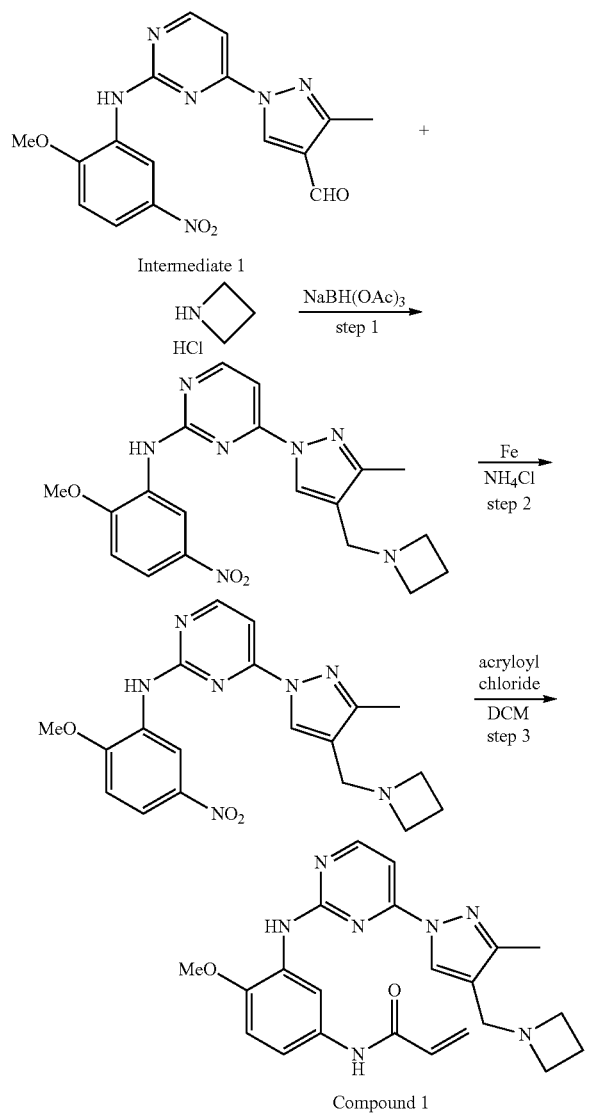

Compound 1

Step 1

To a solution of Intermediate 1 (35.0 mg, 0.10 mmol), diisopropylethylamine (DIPEA, 50 uL, 0.30 mmol) in dimethylacetamide (DMAA, 2 mL) was added 18.5 mg of azetidine hydrochloride (0.20 mmol) at rt. After being stirred for 20 min, 62.8 mg of sodium triacetoxyborohydride (NaBH(OAc)$_3$, 0.30 mmol) was added into the mixture and the resulting mixture was stirred at rt for 16 h. Solvent was evaporated in vacuo and the mixture was purified by column chromatography (0 to 10% MeOH in DCM) to give 4-(4-(azetidin-1-ylmethyl)-3-methyl-1H-pyrazol-1-yl)-N-(2-methoxy-5-nitrophenyl)pyrimidin-2-amine as a red solid (32.0 mg, 82%); MS (ESI) m/z 396.2 [M+H]$^+$.

Step 2

To a solution of the nitro compound above (56.0 mg, 0.14 mmol) in 3 mL mixture of ethanol and water (5:1) were added 78.2 mg of iron (1.42 mmol) and ammonium chloride (38.0 mg, 0.71 mmol). The mixture was heated to 80° C. for 2 h. 2M solution of ammonia in MeOH (2 mL) was added and the resulting mixture was filtered through Celite. The filtrate was concentrated. The resulting residue was extracted with DCM, washed with sat.NaHCO$_3$ solution, brine, dried over anhydrous Na$_2$SO$_4$. The crude oil was purified by column chromatography (0 to 20% MeOH in DCM with 0.1% NH$_3$) to give N-(4-(4-(azetidin-1-ylmethyl)-3-methyl-1H-pyrazol-1-yl)pyrimidin-2-yl)-6-methoxybenzene-1,3-diamine as an off-white solid (38.0 mg, 69%); MS (ESI) m/z 366.2 [M+H]$^+$.

Step 3

To a solution of above aniline (36.0 mg, 0.10 mmol) and DIPEA (18.8 uL, 0.11 mmol) in DCM (2 mL) was added a solution of acryloyl chloride (8.01 uL, 0.10 mmol) in DCM (0.2 mL) at −20° C. The mixture was stirred for 1 h and quenched by addition of sat NaHCO$_3$ solution. The mixture was extracted with DCM and dried over anhydrous Na$_2$SO$_4$. The crude mixture was purified by column chromatography (0 to 10% MeOH in DCM with 0.1% NH$_3$) to give the title compound as an off-white solid. (26.9 mg, 65%); MS (ESI) m/z 420.2 [M+H]$^+$.

Example 2

Compound 2: N-(3-(4-(4-((3-hydroxyazetidin-1-yl)methyl)-3-methyl-1H-pyrazol-1-yl)pyrimidin-2-ylamino)-4-methoxyphenyl)acrylamide Using Intermediate 1 and azetidin-3-ol hydrochloride, the title compound was prepared as described in Example 1; MS (ESI) m/z 436.2 [M+H]$^+$.

Example 3

Compound 3: N-(3-(4-(4-(azetidin-1-ylmethyl)-3-methyl-1H-pyrazol-1-yl)pyrimidin-2-ylamino)phenyl)acrylamide Using Intermediate 2 and azetidine hydrochloride, the title compound was prepared as described in Example 1; MS (ESI) m/z 390.2 [M+H]$^+$.

Example 4

Compound 4: N-(3-(4-(4-((3-hydroxyazetidin-1-yl)methyl)-3-methyl-1H-pyrazol-1-yl)pyrimidin-2-ylamino)phenyl)acrylamide Using Intermediate 2 and azetidin-3-ol hydrochloride, the title compound was prepared as described in Example 1; MS (ESI) m/z 406.2 [M+H]$^+$.

Example 5

Compound 5: N-(3-(4-(4-((3-hydroxyazetidin-1-yl)methyl)-3-methyl-1H-pyrazol-1-yl)pyrimidin-2-ylamino)-5-methylphenyl)acrylamide Using Intermediate 3 and azetidin-3-ol hydrochloride, the title compound was prepared as described in Example 1; MS (ESI) m/z 420.2 [M+H]$^+$.

Example 6

Compound 6: N-(5-(4-(4-((dimethylamino)methyl)-3-(4-fluorophenyl)-1H-pyrazol-1-yl)pyrimidin-2-ylamino)-4-methoxy-2-morpholinophenyl)acrylamide Using Intermediate 71 and dimethylamine, the title compound was prepared as described in Example 1; MS (ESI) m/z 573.3 [M+H]$^+$.

Example 7

Compound 7: N-(5-(4-(3-tert-butyl-4-((dimethylamino)methyl)-1H-pyrazol-1-yl)-5-methylpyrimidin-2-ylamino)-4-methoxy-2-morpholinophenyl)acrylamide Using Intermediate 72 and dimethylamine, the title compound was prepared as described in Example 1; MS (ESI) m/z 549.3 [M+H]$^+$.

Example 8

Compound 8: N-(3-(4-(4-((3-hydroxyazetidin-1-yl)methyl)-3-methyl-1H-pyrazol-1-yl)-5-methylpyrimidin-2-ylamino)-4-methoxyphenyl)acrylamide Using Intermediate 5 and azetidin-3-ol hydrochloride, the title compound was prepared as described in Example 1; MS (ESI) m/z 450.2 [M+H]$^+$.

Example 9

Compound 9: N-(4-methoxy-3-(4-(3-methyl-1H-pyrazol-1-yl)pyrimidin-2-ylamino)phenyl)acrylamide Using Intermediate 6, the title compound was prepared as described in Example 1; MS (ESI) m/z 351.2 [M+H]$^+$.

Example 10

Compound 10: N-(3-(4-(4-((3-hydroxyazetidin-1-yl)methyl)-3-methyl-1H-pyrazol-1-yl)-5-methylpyrimidin-2-ylamino)-5-methylphenyl)acrylamide Using Intermediate 7 and azetidin-3-ol hydrochloride, the title compound was prepared as described in Example 1; MS (ESI) m/z 434.2 [M+H]$^+$.

Example 11

Compound 11: N-(3-(4-(4-((3-hydroxyazetidin-1-yl)methyl)-1H-pyrazol-1-yl)-5-methylpyrimidin-2-ylamino)-4-methoxyphenyl)acrylamide Using Intermediate 8 and azetidin-3-ol hydrochloride, the title compound was prepared as described in Example 1; MS (ESI) m/z 436.2 [M+H]$^+$.

Example 12

Compound 12: N-(5-(4-(4-(azetidin-1-ylmethyl)-3-methyl-1H-pyrazol-1-yl)pyrimidin-2-ylamino)-2-morpholinophenyl)acrylamide Using Intermediate 10 and azetidine hydrochloride, the title compound was prepared as described in Example 1; MS (ESI) m/z 475.3 [M+H]$^+$.

Example 13

Compound 13: N-(2-(4-acetylpiperazin-1-yl)-5-(4-(4-(azetidin-1-ylmethyl)-3-methyl-1H-pyrazol-1-yl)pyrimidin-2-ylamino)phenyl)acrylamide Using Intermediate 11 and azetidine hydrochloride, the title compound was prepared as described in Example 1; MS (ESI) m/z 516.3 [M+H]$^+$.

Example 14

Compound 14: N-(5-(4-(4-(azetidin-1-ylmethyl)-3-methyl-1H-pyrazol-1-yl)pyrimidin-2-ylamino)-4-methoxy-2-morpholinophenyl)acrylamide Using Intermediate 13 and azetidine hydrochloride, the title compound was prepared as described in Example 1; MS (ESI) m/z 505.3 [M+H]$^+$.

Example 15

Compound 15: N-(5-(4-(4-((3-hydroxyazetidin-1-yl)methyl)-3-methyl-1H-pyrazol-1-yl)pyrimidin-2-ylamino)-4-methoxy-2-morpholinophenyl)acrylamide Using Intermediate 13 and azetidin-3-ol hydrochloride, the title compound was prepared as described in Example 1; MS (ESI) m/z 521.3 [M+H]$^+$.

Example 16

Compound 16: N-(5-(4-(4-(azetidin-1-ylmethyl)-3-methyl-1H-pyrazol-1-yl)pyrimidin-2-ylamino)-2-((2-(dimethylamino)ethyl)(methyl)amino)-4-methoxyphenyl)acrylamide Using Intermediate 14 and azetidine hydrochloride, the title compound was prepared as described in Example 1; MS (ESI) m/z 520.3 [M+H]$^+$.

Example 17

Compound 17: N-(5-(4-(4-(azetidin-1-ylmethyl)-3-methyl-1H-pyrazol-1-yl)pyrimidin-2-ylamino)-4-methoxy-2-(4-methylpiperazin-1-yl)phenyl)acrylamide Using Intermediate 15 and azetidine hydrochloride, the title compound was prepared as described in Example 1; MS (ESI) m/z 518.3 [M+H]$^+$.

Example 18

Compound 18: N-(5-(4-(4-(azetidin-1-ylmethyl)-3-methyl-1H-pyrazol-1-yl)pyrimidin-2-ylamino)-4-methoxy-2-(piperidin-1-yl)phenyl)acrylamide Using Intermediate 16 and azetidine hydrochloride, the title compound was prepared as described in Example 1; MS (ESI) m/z 503.3 [M+H]$^+$.

Example 19

Compound 19: N-(5-(4-(4-((3-hydroxyazetidin-1-yl)methyl)-1H-pyrazol-1-yl)-5-methylpyrimidin-2-ylamino)-4-methoxy-2-morpholinophenyl)acrylamide Using Intermediate 18 and azetidin-3-ol hydrochloride, the title compound was prepared as described in Example 1; MS (ESI) m/z 521.3 [M+H]$^+$.

Example 20

Compound 20: N-(5-(4-(4-(((3R,4S)-3,4-dihydroxypyrrolidin-1-yl)methyl)-1H-pyrazol-1-yl)-5-methylpyrimidin-2-ylamino)-4-methoxy-2-morpholinophenyl)acrylamide Using Intermediate 18 and (3R,4S)-pyrrolidine-3,4-diol hydrochloride, the title compound was prepared as described in Example 1; MS (ESI) m/z 551.3 [M+H]$^+$.

Example 21

Compound 21: N-(5-(4-(4-(((3S,4R)-3-hydroxy-4-methoxypyrrolidin-1-yl)methyl)-1H-pyrazol-1-yl)-5-methylpyrimidin-2-ylamino)-4-methoxy-2-morpholinophenyl)acrylamide Using Intermediate 18 and (3S,4R)-4-methoxypyrrolidin-3-ol hydrochloride, the title compound was prepared as described in Example 1; MS (ESI) m/z 565.3 [M+H]$^+$.

Example 22

Compound 22: N-(5-(4-(4-((dimethylamino)methyl)-1H-pyrazol-1-yl)-5-methylpyrimidin-2-ylamino)-4-methoxy-2-morpholinophenyl)acrylamide Using Intermediate 18 and dimethylamine, the title compound was prepared as described in Example 1; MS (ESI) m/z 493.3 [M+H]$^+$.

Example 23

Compound 23: N-(4-methoxy-5-(5-methyl-4-(4-((methyl(1-methylazetidin-3-yl)amino)methyl)-1H-pyrazol-1-yl)pyrimidin-2-ylamino)-2-morpholinophenyl)acrylamide Using Intermediate 18 and N,1-dimethylazetidin-3-amine hydrochloride, the title compound was prepared as described in Example 1; MS (ESI) m/z 548.3 [M+H]$^+$.

Example 24

Compound 24: N-(5-(4-(4-((3-hydroxyazetidin-1-yl)methyl)-3-methyl-1H-pyrazol-1-yl)-5-methylpyrimidin-2-ylamino)-4-methoxy-2-morpholinophenyl)acrylamide Using Intermediate 20 and azetidin-3-ol hydrochloride, the title compound was prepared as described in Example 1; MS (ESI) m/z 535.3 [M+H]$^+$.

Example 25

Compound 25: N-(5-(4-(4-(((3R,4S)-3,4-dihydroxypyrrolidin-1-yl)methyl)-3-methyl-1H-pyrazol-1-yl)-5-methylpyrimidin-2-ylamino)-4-methoxy-2-morpholinophenyl)acrylamide Using Intermediate 20 and (3R,4S)-pyrrolidine-3,4-diol hydrochloride, the title compound was prepared as described in Example 1; MS (ESI) m/z 565.3 [M+H]$^+$.

Example 26

Compound 26: N-(5-(4-(4-(((3S,4R)-3-hydroxy-4-methoxypyrrolidin-1-yl)methyl)-3-methyl-1H-pyrazol-1-yl)-5-methylpyrimidin-2-ylamino)-4-methoxy-2-morpholinophenyl)acrylamide Using Intermediate 20 and (3S,4R)-4-methoxypyrrolidin-3-ol hydrochloride, the title compound was prepared as described in Example 1; MS (ESI) m/z 579.3 [M+H]$^+$.

Example 27

Compound 27: (R)—N-(5-(4-(4-((3-hydroxypyrrolidin-1-yl)methyl)-3-methyl-1H-pyrazol-1-yl)-5-methylpyrimidin-2-ylamino)-4-methoxy-2-morpholinophenyl)acrylamide Using Intermediate 20 and (R)-pyrrolidin-3-ol hydrochloride, the title compound was prepared as described in Example 1; MS (ESI) m/z 549.3 [M+H]$^+$.

Example 28

Compound 28: (S)—N-(5-(4-(4-((3-hydroxypyrrolidin-1-yl)methyl)-3-methyl-1H-pyrazol-1-yl)-5-methylpyrimidin-2-ylamino)-4-methoxy-2-morpholinophenyl)acrylamide Using Intermediate 20 and (S)-pyrrolidin-3-ol hydrochloride, the title compound was prepared as described in Example 1; MS (ESI) m/z 549.3 [M+H]$^+$.

Example 29

Compound 29: N-(5-(4-(4-((3-hydroxyazetidin-1-yl)methyl)-3-methyl-1H-pyrazol-1-yl)-5-methylpyrimidin-2-ylamino)-4-methoxy-2-(4-methylpiperazin-1-yl)phenyl)acrylamide Using Intermediate 21 and azetidin-3-ol hydrochloride, the title compound was prepared as described in Example 1; MS (ESI) m/z 548.3 [M+H]$^+$.

Example 30

Compound 30: N-(5-(4-(4-((3-hydroxyazetidin-1-yl)methyl)-3-methyl-1H-pyrazol-1-yl)-5-methylpyrimidin-2-ylamino)-4-methoxy-2-(piperidin-1-yl)phenyl)acrylamide Using Intermediate 22 and azetidin-3-ol hydrochloride, the title compound was prepared as described in Example 1; MS (ESI) m/z 533.3 [M+H]$^+$.

Example 31

Compound 31: N-(2-((2-(dimethylamino)ethyl)(methyl)amino)-5-(4-(4-((3-hydroxyazetidin-1-yl)methyl)-3-methyl-1H-pyrazol-1-yl)-5-methylpyrimidin-2-ylamino)-4-methoxyphenyl)acrylamide Using Intermediate 23 and azetidin-3-ol hydrochloride, the title compound was prepared as described in Example 1; MS (ESI) m/z 550.3 [M+H]$^+$.

Example 32

Compound 32: N-(5-(4-(4-(azetidin-1-ylmethyl)-1H-pyrazol-1-yl)-5-methylpyrimidin-2-ylamino)-4-methoxy-2-morpholinophenyl)acrylamide Using Intermediate 18 and azetidine hydrochloride, the title compound was prepared as described in Example 1; MS (ESI) m/z 505.3 [M+H]$^+$.

Example 33

Compound 33: N-(4-methoxy-5-(5-methyl-4-(4-(morpholinomethyl)-1H-pyrazol-1-yl)pyrimidin-2-ylamino)-2-(4-methylpiperazin-1-yl)phenyl)acrylamide Using Intermediate 24 and morpholine, the title compound was prepared as described in Example 1; MS (ESI) m/z 548.3 [M+H]$^+$.

Example 34

Compound 34: N-(5-(4-(4-(azetidin-1-ylmethyl)-1H-pyrazol-1-yl)pyrimidin-2-ylamino)-4-methoxy-2-morpholinophenyl)acrylamide Using Intermediate 26 and azetidine hydrochloride, the title compound was prepared as described in Example 1; MS (ESI) m/z 491.2 [M+H]$^+$.

Example 35

Compound 35: (S)—N-(5-(4-(4-((3-(dimethylamino)pyrrolidin-1-yl)methyl)-1H-pyrazol-1-yl)pyrimidin-2-ylamino)-4-methoxy-2-morpholinophenyl)acrylamide Using Intermediate 26 and (S)—N,N-dimethylpyrrolidin-3-amine, the title compound was prepared as described in Example 1; MS (ESI) m/z 548.3 [M+H]$^+$.

Example 36

Compound 36: N-(5-(4-(4-(azetidin-1-ylmethyl)-1H-pyrazol-1-yl)-5-methylpyrimidin-2-ylamino)-4-methoxy-2-(4-methylpiperazin-1-yl)phenyl)acrylamide Using Intermediate 24 and azetidine hydrochloride, the title compound was prepared as described in Example 1; MS (ESI) m/z 518.3 [M+H]$^+$.

Example 37

Compound 37: N-(2-(4-acetylpiperazin-1-yl)-5-(4-(4-(azetidin-1-ylmethyl)-1H-pyrazol-1-yl)-5-methylpyrimidin-2-ylamino)-4-methoxyphenyl)acrylamide Using Intermediate 27 and azetidine hydrochloride, the title compound was prepared as described in Example 1; MS (ESI) m/z 546.3 [M+H]$^+$.

Example 38

Compound 38: N-(5-(4-(4-(azetidin-1-ylmethyl)-1H-pyrazol-1-yl)pyrimidin-2-ylamino)-2-(dimethylamino)-4-methoxyphenyl)acrylamide Using Intermediate 28 and azetidine hydrochloride, the title compound was prepared as described in Example 1; MS (ESI) m/z 449.2 [M+H]$^+$.

Example 39

Compound 39: (R)—N-(5-(4-(4-((3-(dimethylamino)pyrrolidin-1-yl)methyl)-1H-pyrazol-1-yl)pyrimidin-2-ylamino)-4-methoxy-2-morpholinophenyl)acrylamide Using Intermediate 26 and (R)—N,N-dimethylpyrrolidin-3-amine, the title compound was prepared as described in Example 1; MS (ESI) m/z 548.3 [M+H]$^+$.

Example 40

Compound 40: N-(5-(4-(4-(azetidin-1-ylmethyl)-1H-pyrazol-1-yl)-5-methylpyrimidin-2-ylamino)-4-methoxy-2-(1,4-oxazepan-4-yl)phenyl)acrylamide Using Intermediate 29 and azetidine hydrochloride, the title compound was prepared as described in Example 1; MS (ESI) m/z 519.3 [M+H]$^+$.

Example 41

Compound 41: N-(5-(4-(4-(azetidin-1-ylmethyl)-1H-pyrazol-1-yl)-5-methylpyrimidin-2-ylamino)-4-methoxy-2-(4-methyl-1,4-diazepan-1-yl)phenyl)acrylamide Using Intermediate 30 and azetidine hydrochloride, the title compound was prepared as described in Example 1; MS (ESI) m/z 532.3 [M+H]$^+$.

Example 42

Compound 42: N-(5-(4-(4-(azetidin-1-ylmethyl)-1H-pyrazol-1-yl)-5-methylpyrimidin-2-ylamino)-2-((2-(dimethylamino)ethyl)(methyl)amino)-4-methoxyphenyl)acrylamide Using Intermediate 31 and azetidine hydrochloride, the title compound was prepared as described in Example 1; MS (ESI) m/z 520.3 [M+H]$^+$.

Example 43

Compound 43: N-(2-((2-(dimethylamino)ethyl)(methyl)amino)-5-(4-(4-(((3S,4R)-3-hydroxy-4-methoxypyrrolidin-1-yl)methyl)-1H-pyrazol-1-yl)-5-methylpyrimidin-2-ylamino)-4-methoxyphenyl)acrylamide Using Intermediate 31 and (3S,4R)-4-methoxypyrrolidin-3-ol hydrochloride, the title compound was prepared as described in Example 1; MS (ESI) m/z 580.3 [M+H]$^+$.

Example 44

Compound 44: N-(4-methoxy-5-(4-(4-((3-methoxyazetidin-1-yl)methyl)-3-methyl-1H-pyrazol-1-yl)pyrimidin-2-ylamino)-2-morpholinophenyl)acrylamide Using Intermediate 13 and 3-methoxyazetidine hydrochloride, the title compound was prepared as described in Example 1; MS (ESI) m/z 535.3 [M+H]$^+$.

Example 45

Compound 45: N-(5-(4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide Using Intermediate 13 and (3S,4R)-4-methoxypyrrolidin-3-ol hydrochloride, the title compound was prepared as described in Example 1; MS (ESI) m/z 565.3 [M+H]$^+$.

Example 46

Compound 46: N-(5-(4-(4-((dimethylamino)methyl)-3-methyl-1H-pyrazol-1-yl)pyrimidin-2-ylamino)-4-methoxy-2-morpholinophenyl)acrylamide Using Intermediate 13 and dimethylamine, the title compound was prepared as described in Example 1; MS (ESI) m/z 493.3 [M+H]$^+$.

$^1$H NMR: δ (DMSO-d$_6$), 2.13 ppm (6H, s), 2.26 ppm (3H, s), 2.83~2.86 ppm (4H, t), 3.80~3.81 ppm (4H, t), 3.90 ppm (3H, s), 5.80 ppm (1H, d), 6.34~6.39 ppm (1H, d), 6.67~6.76 ppm (1H, q), 6.94 (1H, s), 7.17 ppm (1H, d), 8.09 ppm (1H, s), 8.45 ppm (1H, d), 8.91 ppm (1H, s), 9.01 ppm (1H, s), 9.12 ppm (1H, s).

Example 47

Compound 47: N-(5-(4-(4-((dimethylamino)methyl)-3-methyl-1H-pyrazol-1-yl)pyrimidin-2-ylamino)-4-methoxy-2-(4-methylpiperazin-1-yl)phenyl)acrylamide Using Intermediate 15 and dimethylamine, the title compound was prepared as described in Example 1; MS (ESI) m/z 506.3 [M+H]$^+$.

Example 48

Compound 48: N-(5-(4-(3-((3-hydroxyazetidin-1-yl)methyl)-4-methyl-1H-pyrrol-1-yl)-5-methylpyrimidin-2-ylamino)-4-methoxy-2-morpholinophenyl)acrylamide Using Intermediate 33 and azetidin-3-ol hydrochloride, the title compound was prepared as described in Example 1; MS (ESI) m/z 534.3 [M+H]$^+$.

Example 49

Compound 49: N-(5-(5-chloro-4-(4-((3-hydroxyazetidin-1-yl)methyl)-3-methyl-1H-pyrazol-1-yl)pyrimidin-2-ylamino)-4-methoxy-2-morpholinophenyl)acrylamide Using Intermediate 35 and azetidin-3-ol hydrochloride, the title compound was prepared as described in Example 1; MS (ESI) m/z 555.2 [M+H]$^+$.

Example 50

Compound 50: N-(5-(4-(4-(azetidin-1-ylmethyl)-3-methyl-1H-pyrazol-1-yl)-5-chloropyrimidin-2-ylamino)-4-methoxy-2-morpholinophenyl)acrylamide Using Intermediate 35 and azetidine hydrochloride, the title compound was prepared as described in Example 1; MS (ESI) m/z 539.2 [M+H]$^+$.

Example 51

Compound 51: N-(5-(5-chloro-4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide Using Intermediate 35 and (3S,4R)-4-methoxypyrrolidin-3-ol hydrochloride, the title compound was prepared as described in Example 1; MS (ESI) m/z 599.2 [M+H]$^+$.

Example 52

Compound 52: N-(5-(5-chloro-4-(4-((dimethylamino)methyl)-3-methyl-1H-pyrazol-1-yl)pyrimidin-2-ylamino)-4-methoxy-2-morpholinophenyl)acrylamide Using Intermediate 35 and dimethylamine, the title compound was prepared as described in Example 1; MS (ESI) m/z 527.2 [M+H]$^+$.

Example 53

Compound 53: N-(5-(4-(4-(azetidin-1-ylmethyl)-3-methyl-1H-pyrazol-1-yl)pyrimidin-2-ylamino)-4-methoxy-2-(1H-pyrazol-1-yl)phenyl)acrylamide Using Intermediate 36 and azetidine hydrochloride, the title compound was prepared as described in Example 1; MS (ESI) m/z 539.2 [M+H]+.

Example 54

Compound 54: N-(5-(5-chloro-4-(4-(((3R,4S)-3,4-dihydroxypyrrolidin-1-yl)methyl)-3-methyl-1H-pyrazol-1-yl)pyrimidin-2-ylamino)-4-methoxy-2-(4-methylpiperazin-1-yl)phenyl)acrylamide Using Intermediate 37 and (3R,4S)-pyrrolidine-3,4-diol hydrochloride, the title compound was prepared as described in Example 1; MS (ESI) m/z 598.3 [M+H]+.

Example 55

Compound 55: N-(5-(4-(4-(azetidin-1-ylmethyl)-3-cyclopropyl-1H-pyrazol-1-yl)pyrimidin-2-ylamino)-4-methoxy-2-morpholinophenyl)acrylamide Using Intermediate 39 and azetidine hydrochloride, the title compound was prepared as described in Example 1; MS (ESI) m/z 531.3 [M+H]+.
$^1$H NMR: δ (DMSO-$d_6$), 0.90~0.95 ppm (4H, m), 1.92~2.03 ppm (3H, m), 2.84~2.85 ppm (4H, m), 3.14 ppm (4H, t), 3.53 ppm (2H, s), 3.80~3.82 ppm (4H, m), 3.89 ppm (3H, s), 5.82 ppm (1H, d), 6.39~6.44 (1H, d), 6.69~6.78 ppm (1H, q), 6.93 ppm (1H, s), 7.09 ppm (1H, d), 8.09 ppm (1H, s), 8.43 ppm (1H, d), 8.85 ppm (1H, s), 8.98 ppm (1H, s), 9.14 ppm (1H, s).

Example 56

Compound 56: N-(5-(4-(3-cyclopropyl-4-(((3S,4R)-3-hydroxy-4-methoxypyrrolidin-1-yl)methyl)-1H-pyrazol-1-yl)pyrimidin-2-ylamino)-4-methoxy-2-morpholinophenyl)acrylamide Using Intermediate 39 and (3S,4R)-4-methoxypyrrolidin-3-ol hydrochloride, the title compound was prepared as described in Example 1; MS (ESI) m/z 591.3 [M+H]+.

Example 57

Compound 57: N-(3-(4-(4-((3-hydroxyazetidin-1-yl)methyl)-3-methyl-1H-pyrazol-1-yl)pyrimidin-2-ylamino)-5-(1-methyl-1H-pyrazol-4-yl)phenyl)acrylamide Using Intermediate 41 and azetidin-3-ol hydrochloride, the title compound was prepared as described in Example 1; MS (ESI) m/z 486.2 [M+H]+.

Example 58

Compound 58: N-(5-(4-(4-((3-hydroxyazetidin-1-yl)methyl)-3-methyl-1H-pyrazol-1-yl)pyrimidin-2-ylamino)-4-methoxy-2-(1-methyl-1H-pyrazol-4-yl)phenyl)acrylamide Using Intermediate 43 and azetidin-3-ol hydrochloride, the title compound was prepared as described in Example 1; MS (ESI) m/z 516.2 [M+H]+.

Example 59

Compound 59: N-(5-(4-(4-(azetidin-1-ylmethyl)-3-methyl-1H-pyrazol-1-yl)pyrimidin-2-ylamino)-4-methoxy-2-(1-methyl-1,2,3,6-tetrahydropyridin-4-yl)phenyl)acrylamide Using Intermediate 45 and azetidine hydrochloride, the title compound was prepared as described in Example 1; MS (ESI) m/z 515.3 [M+H]+.

Example 60

Compound 60: N-(5-(4-(3-(azetidin-1-ylmethyl)-4-methyl-1H-pyrrol-1-yl)-5-fluoropyrimidin-2-ylamino)-4-methoxy-2-morpholinophenyl)acrylamide Using Intermediate 47 and azetidine hydrochloride, the title compound was prepared as described in Example 1; MS (ESI) m/z 522.3 [M+H]+.

Example 61

Compound 61: N-(5-(5-fluoro-4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide Using Intermediate 48 and (3S,4R)-4-methoxypyrrolidin-3-ol hydrochloride, the title compound was prepared as described in Example 1; MS (ESI) m/z 583.3 [M+H]+.

Example 62

Compound 62: N-(5-(4-(4-(azetidin-1-ylmethyl)-3-methyl-1H-pyrazol-1-yl)-5-fluoropyrimidin-2-ylamino)-4-methoxy-2-morpholinophenyl)acrylamide Using Intermediate 48 and azetidine hydrochloride, the title compound was prepared as described in Example 1; MS (ESI) m/z 523.3 [M+H]+.

Example 63

Compound 63: N-(5-(4-(4-(azetidin-1-ylmethyl)-1H-pyrazol-1-yl)-5-methylpyrimidin-2-ylamino)-4-isopropoxy-2-morpholinophenyl)acrylamide Using Intermediate 50 and azetidine hydrochloride, the title compound was prepared as described in Example 1; MS (ESI) m/z 533.3 [M+H]+.

Example 64

Compound 64: N-(5-(4-(4-(azetidin-1-ylmethyl)-1H-pyrazol-1-yl)-5-methylpyrimidin-2-ylamino)-4-methoxy-2-(1-methyl-1,2,3,6-tetrahydropyridin-4-yl)phenyl)acrylamide Using Intermediate 51 and azetidine hydrochloride, the title compound was prepared as described in Example 1; MS (ESI) m/z 515.3 [M+H]$^+$.

Example 65

Compound 65: N-(4-(4-(4-(azetidin-1-ylmethyl)-3-methyl-1H-pyrazol-1-yl)pyrimidin-2-ylamino)-5-methoxybiphenyl-2-yl)acrylamide Using Intermediate 53 and azetidine hydrochloride, the title compound was prepared as described in Example 1; MS (ESI) m/z 496.2 [M+H]$^+$.

Example 66

Compound 66: N-(5-(4-(4-(hydroxymethyl)-3-methyl-1H-pyrazol-1-yl)pyrimidin-2-ylamino)-4-methoxy-2-morpholinophenyl)acrylamide Using Intermediate 54, the title compound was prepared as described in Example 1; MS (ESI) m/z 466.2 [M+H]$^+$.

Example 67

Compound 67: N-(5-(4-(4-(azetidin-1-ylmethyl)-3-tert-butyl-1H-pyrazol-1-yl)-5-methylpyrimidin-2-ylamino)-4-methoxy-2-morpholinophenyl)acrylamide Using Intermediate 72 and azetidine hydrochloride, the title compound was prepared as described in Example 1; MS (ESI) m/z 561.3 [M+H]$^+$.

Example 68

Compound 68: N-(4-(4-(4-(azetidin-1-ylmethyl)-3-methyl-1H-pyrazol-1-yl)pyrimidin-2-ylamino)-2',5-dimethoxybiphenyl-2-yl)acrylamide Using Intermediate 57 and azetidine hydrochloride, the title compound was prepared as described in Example 1; MS (ESI) m/z 526.3 [M+H]$^+$.

Example 69

Compound 69: N-(5-(4-(4-(azetidin-1-ylmethyl)-3-methyl-1H-pyrazol-1-yl)pyrimidin-2-ylamino)-2-(4,4-difluoropiperidin-1-yl)-4-methoxyphenyl)acrylamide Using Intermediate 59 and azetidine hydrochloride, the title compound was prepared as described in Example 1; MS (ESI) m/z 539.3 [M+H]$^+$.

Example 70

Compound 70: N-(5-(4-(4-(azetidin-1-ylmethyl)-3,5-dimethyl-1H-pyrazol-1-yl)pyrimidin-2-ylamino)-4-methoxy-2-morpholinophenyl)acrylamide Using Intermediate 61 and azetidine hydrochloride, the title compound was prepared as described in Example 1; MS (ESI) m/z 519.3 [M+H]$^+$.

Example 71

Compound 71: N-(2-(dimethylamino)-5-(4-(4-((dimethylamino)methyl)-3-methyl-1H-pyrazol-1-yl)pyrimidin-2-ylamino)-4-methoxyphenyl)acrylamide Using Intermediate 62 and dimethylamine, the title compound was prepared as described in Example 1; MS (ESI) m/z 451.3 [M+H]$^+$.

Example 72

Compound 72: N-(5-(4-(4-((3-fluoroazetidin-1-yl)methyl)-3-methyl-1H-pyrazol-1-yl)pyrimidin-2-ylamino)-4-methoxy-2-morpholinophenyl)acrylamide Using Intermediate 13 and 3-fluoroazetidine hydrochloride, the title compound was prepared as described in Example 1; MS (ESI) m/z 523.3 [M+H]$^+$.

Example 73

Compound 73: N-(5-(4-(4-((dimethylamino)methyl)-3-phenyl-1H-pyrazol-1-yl)pyrimidin-2-ylamino)-4-methoxy-2-morpholinophenyl)acrylamide Using Intermediate 64 and dimethylamine, the title compound was prepared as described in Example 1; MS (ESI) m/z 555.3 [M+H]$^+$. $^1$H-NMR: δ (DMSO-d6), 2.21 ppm (6H, s), 2.85~2.86 ppm (4H, t), 3.46 ppm (2H, s), 3.81~3.83 ppm (4H, t), 3.91 ppm (3H, s), 5.82~6.43 ppm (2H, dd), 6.72~6.76 ppm (1H, dd), 6.96 ppm (1H, s), 7.34~7.35 (1H, d), 7.41~7.43 ppm (1H, t), 7.47~7.50 ppm (2H, t), 8.04~8.05 ppm (2H, d), 8.18 ppm (1H, s), 8.53~8.54 ppm (1H, d), 9.07 ppm (1H, s), 9.15 ppm (2H, s).

Example 74

Compound 74: N-(5-(4-(3-cyclopropyl-4-((dimethylamino)methyl)-1H-pyrazol-1-yl)pyrimidin-2-ylamino)-4-methoxy-2-morpholinophenyl)acrylamide Using Intermediate 39 and dimethylamine, the title compound was prepared as described in Example 1; MS (ESI) m/z 519.3 [M+H]$^+$. $^1$H NMR (500 MHz, DMSO-d$_6$) δ ppm 0.92-0.95 (m, 4H), 2.00-2.06 (m, 1H), 2.19 (br s, 4H), 3.18 (br s, 4H), 3.44 (s, 2H), 3.82 (d, J=4.5 Hz, 4H), 3.91 (s, 3H), 5.80 (dd, J=1.5 Hz, 10 Hz, 1H), 6.37 (dd, J=2.0 Hz, 17 Hz, 1H), 6.45-6.68 (m, 1H), 6.96 (s, 1H), 7.13 (d, J=5.0 Hz, 1H), 8.00 (s, 1H), 8.44 (d, J=5.0 Hz, 1H), 8.86 (s, 1H), 9.05 (br d, J=7.0 Hz, 1H).

Example 75

Compound 75: N-(5-(4-(4-((dimethylamino)methyl)-3-methyl-1H-pyrazol-1-yl)-5-methylpyrimidin-2-ylamino)-4-methoxy-2-morpholinophenyl)acrylamide Using Intermediate 20 and dimethylamine, the title compound was prepared as described in Example 1; MS (ESI) m/z 507.3 [M+H]$^+$.
$^1$H NMR: δ (DMSO-d$_6$), 2.12 ppm (6H, s), 2.26 ppm (3H, s), 2.82~2.84 ppm (4H, t), 3.79~3.81 ppm (4H, t), 3.90 ppm (3H, s), 5.79 ppm (1H, d), 6.31~6.36 ppm (1H, d), 6.66~6.75 ppm (1H, q), 6.93 (1H, s), 7.96 ppm (1H, d), 8.37 ppm (1H, s), 8.83 ppm (1H, d), 8.89 ppm (1H, s), 9.11 ppm (1H, s).

Example 76

Compound 76: N-(5-(4-(4-(azetidin-1-ylmethyl)-3-methyl-1H-pyrazol-1-yl)-5-methylpyrimidin-2-ylamino)-4-methoxy-2-morpholinophenyl)acrylamide Using Intermediate 20 and azetidine hydrochloride, the title compound was prepared as described in Example 1; MS (ESI) m/z 519.3 [M+H]$^+$.

Example 77

Compound 77: N-(5-(5-chloro-4-(4-((dimethylamino)methyl)-1H-pyrazol-1-yl)pyrimidin-2-ylamino)-4-methoxy-2-morpholinophenyl)acrylamide Using Intermediate 66 and dimethylamine, the title compound was prepared as described in Example 1; MS (ESI) m/z 513.2 [M+H]$^+$.

Example 78

Compound 78: N-(5-(4-(4-(azetidin-1-ylmethyl)-3-phenyl-1H-pyrazol-1-yl)pyrimidin-2-ylamino)-4-methoxy-2-morpholinophenyl)acrylamide Using Intermediate 64 and azetidine hydrochloride, the title compound was prepared as described in Example 1; MS (ESI) m/z 567.3 [M+H]$^+$. $^1$H NMR (500 MHz, DMSO-d6) δ 2.01-1.96 (m, 2H), 2.89-2.87 (m, 4H), 3.18 (s, 2H), 3.21-3.18 (m, 4H), 3.85-3.83 (m, 4H), 3.93 (s, 3H), 5.85 (d, J=10 Hz, 1H), 6.46 (d, J=17 Hz, 1H), 6.73 (dd, J=17.0, 10.0 Hz, 1H), 6.99 (s, 1H), 7.35 (d, J=5.5 Hz, 1H), 7.45-7.42 (m, 1H), 7.51 (t, J=8.0 Hz, 2H), 8.01 (d, J=8.5 Hz, 2H), 8.12 (s, 1H), 8.53 (d, J=5.0 Hz, 1H), 9.07 (s, 1H), 9.08 (b rs, 1H).

Example 79

Compound 79: N-(5-(4-(4-((dimethylamino)methyl)-3-methyl-1H-pyrazol-1-yl)pyrimidin-2-ylamino)-2-(4-(2-fluoroethyl)piperazin-1-yl)-4-methoxyphenyl)acrylamide Using Intermediate 67 and dimethylamine, the title compound was prepared as described in Example 1; MS (ESI) m/z 538.3 [M+H]$^+$.

Example 80

Compound 80: N-(5-(4-(4-((dimethylamino)methyl)-3-p-tolyl-1H-pyrazol-1-yl)pyrimidin-2-ylamino)-4-methoxy-2-morpholinophenyl)acrylamide Using Intermediate 69 and dimethylamine, the title compound was prepared as described in Example 1; MS (ESI) m/z 569.3 [M+H]$^+$.

Example 81

Compound 81: N-(5-(4-(4-(azetidin-1-ylmethyl)-3-(4-fluorophenyl)-1H-pyrazol-1-yl)pyrimidin-2-ylamino)-4-methoxy-2-morpholinophenyl)acrylamide Using Intermediate 71 and azetidine hydrochloride, the title compound was prepared as described in Example 1; MS (ESI) m/z 585.3 [M+H]$^+$.

Example 82

Compound 82: N-(5-(4-(4-(azetidin-1-ylmethyl)-3-p-tolyl-1H-pyrazol-1-yl)pyrimidin-2-ylamino)-4-methoxy-2-morpholinophenyl)acrylamide Using Intermediate 69 and azetidine hydrochloride, the title compound was prepared as described in Example 1; MS (ESI) m/z 581.3 [M+H]$^+$.
$^1$H NMR: δ (DMSO-d$_6$), 1.08~1.23 ppm (4H, m), 1.96 ppm (2H, t), 2.37 ppm (4H, s), 2.85~2.86 ppm (5H, m), 3.18 ppm (4H, t), 3.57 ppm (3H, s), 3.81~3.83 ppm (5H, m), 3.91 ppm (3H, s), 5.86 ppm (1H, d), 6.45~6.50 ppm (1H, d), 6.72~6.81 ppm (1H, q), 6.96 (1H, s), 7.28~7.32 ppm (3H, m), 7.90 ppm (2H, d), 8.19 ppm (1H, s), 8.52 ppm (1H, d), 9.07 ppm (2H, d), 9.17 ppm (1H, s).

Example 83

Compound 83: N-(2-(dimethylamino)-5-(4-(4-((dimethylamino)methyl)-3-phenyl-1H-pyrazol-1-yl)pyrimidin-2-ylamino)-4-methoxyphenyl)acrylamide Using Intermediate 73 and dimethylamine, the title compound was prepared as described in Example 1; MS (ESI) m/z 513.3 [M+H]$^+$.
$^1$H NMR: δ (DMSO-d$_6$), 2.21 ppm (6H, s), 2.66 ppm (6H, s), 3.46 ppm (2H, s), 3.91 ppm (3H, s), 5.77~5.81 ppm (1H, dd), 6.37~6.43 ppm (1H, d), 6.75~6.84 ppm (1H, q), 6.91 (1H, s), 7.33 ppm (1H, d), 7.40~7.51 ppm (3H, m), 8.04 ppm (2H, d), 8.16 ppm (1H, s), 8.52 ppm (1H, d), 8.98 ppm (1H, br), 9.11 ppm (1H, s), 9.28 ppm (1H, s).

Example 84

Compound 84: N-(2-(azetidin-1-yl)-5-(4-(4-((dimethylamino)methyl)-3-phenyl-1H-pyrazol-1-yl)pyrimidin-2-ylamino)-4-methoxyphenyl)acrylamide Using Intermediate 74 and dimethylamine, the title compound was prepared as described in Example 1; MS (ESI) m/z 525.3 [M+H]$^+$.

Example 85

Compound 85: N-(4-methoxy-2-(4-methylpiperazin-1-yl)-5-(4-(3-phenyl-1H-pyrazol-1-yl)pyrimidin-2-ylamino)phenyl)acrylamide Using Intermediate 77, the title compound was prepared as described in Example 1; MS (ESI) m/z 511.3 [M+H]$^+$.

Example 86

Compound 86: N-(5-(4-(3-tert-butyl-4-((dimethylamino)methyl)-1H-pyrazol-1-yl)pyrimidin-2-ylamino)-4-methoxy-2-morpholinophenyl)acrylamide Using Intermediate 79 and dimethylamine, the title compound was prepared as described in Example 1; MS (ESI) m/z 535.3 [M+H]$^+$.

$^1$H NMR: δ (DMSO-d$_6$), 1.39 ppm (9H, s), 2.15 ppm (6H, s), 2.83~2.85 ppm (4H, t), 3.40 ppm (2H, s), 3.81 ppm (4H, t), 3.90 ppm (3H, s), 5.86 ppm (1H, d), 6.35~6.41 ppm (1H, d), 6.68~6.77 ppm (1H, q), 6.94 ppm (1H, s), 7.18 ppm (1H, d), 8.09 ppm (1H, s), 8.46 ppm (1H, d), 8.88 ppm (1H, s), 9.01 ppm (1H, s), 9.12 ppm (1H, s).

Example 87

Compound 87: N-(2-(azetidin-1-yl)-5-(4-(4-(azetidin-1-ylmethyl)-3-phenyl-1H-pyrazol-1-yl)pyrimidin-2-ylamino)-4-methoxyphenyl)acrylamide Using Intermediate 74 and azetidine hydrochloride, the title compound was prepared as described in Example 1; MS (ESI) m/z 537.3 [M+H]$^+$.

$^1$H NMR: δ (DMSO-d$_6$), 1.05~1.30 ppm (4H, m), 1.97 ppm (2H, t), 2.20~2.27 ppm (3H, m), 3.15 ppm (4H, t), 3.57 ppm (2H, s), 3.83~3.86 ppm (10H, m), 5.77 ppm (1H, d), 6.24 ppm (1H, s), 6.33~6.38 ppm (1H, d), 6.51~6.60 ppm (1H, q), 7.22 ppm (1H, d), 7.42~7.52 ppm (3H, m), 7.93~8.00 ppm (3H, m), 8.18 ppm (1H, s), 8.46 ppm (1H, d), 8.73 ppm (1H, s), 9.32 ppm (1H, s).

Example 88

Compound 88: N-(5-(4-(4-((dimethylamino)methyl)-3-(thiophen-2-yl)-1H-pyrazol-1-yl)pyrimidin-2-ylamino)-4-methoxy-2-morpholinophenyl)acrylamide Using Intermediate 80 and dimethylamine, the title compound was prepared as described in Example 1; MS (ESI) m/z 561.2 [M+H]$^+$.

$^1$H NMR: δ (DMSO-d$_6$), 2.22 ppm (6H, s), 2.84 ppm (4H, t), 3.51 ppm (2H, s), 3.81 ppm (4H, t), 3.91 ppm (3H, s), 5.82~5.86 ppm (1H, dd), 6.39~6.45 ppm (1H, d), 6.70~6.79 ppm (1H, q), 6.96 ppm (1H, s), 7.19 ppm (1H, t), 7.27 ppm (1H, d), 7.62 ppm (1H, d), 7.78 ppm (1H, d), 8.18 ppm (1H, s), 8.53 ppm (1H, d), 9.06 ppm (1H, s), 9.15 ppm (2H, s).

Example 89

Compound 89: N-(5-(4-(4-((dimethylamino)methyl)-3-(2,5-dimethylphenyl)-1H-pyrazol-1-yl)pyrimidin-2-ylamino)-4-methoxy-2-morpholinophenyl)acrylamide Using Intermediate 82 and dimethylamine, the title compound was prepared as described in Example 1; MS (ESI) m/z 583.3 [M+H]$^+$.

Example 90

Compound 90: N-(4-methoxy-2-morpholino-5-(4-(3-phenyl-4-(pyrrolidin-1-ylmethyl)-1H-pyrazol-1-yl)pyrimidin-2-ylamino)phenyl)acrylamide Using Intermediate 64 and pyrrolidine, the title compound was prepared as described in Example 1; MS (ESI) m/z 581.3 [M+H]$^+$.

$^1$H NMR: δ (DMSO-d$_6$), 1.65~1.75 ppm (4H, m), 2.85 ppm (4H, s), 3.66 ppm (2H, s), 3.81 ppm (4H, t), 3.91 ppm (3H, s), 5.79~5.83 ppm (1H, d), 6.35~6.40 ppm (1H, d), 6.69~6.78 ppm (1H, q), 6.96 ppm (1H, s), 7.34 ppm (1H, d), 7.42~7.52 ppm (3H, m), 8.04 ppm (2H, d), 8.19 ppm (1H, s), 8.53 ppm (1H, d), 9.04 ppm (1H, s), 9.12 ppm (2H, d).

Example 91

Compound 91: N-(5-(4-(4-(hydroxymethyl)-3-phenyl-1H-pyrazol-1-yl)pyrimidin-2-ylamino)-4-methoxy-2-morpholinophenyl)acrylamide Using Intermediate 83, the title compound was prepared as described in Example 1; MS (ESI) m/z 528.2 [M+H]$^+$.

Example 92

Compound 92: N-(5-(4-(4-((ethyl(methyl)amino)methyl)-3-phenyl-1H-pyrazol-1-yl)pyrimidin-2-ylamino)-4-methoxy-2-morpholinophenyl)acrylamide Using Intermediate 64 and N-ethylmethylamine, the title compound was prepared as described in Example 1; MS (ESI) m/z 569.3 [M+H]$^+$.

$^1$H NMR: δ (DMSO-d$_6$), 1.04 ppm (3H, t), 2.17 ppm (6H, s), 2.84~2.86 ppm (4H, t), 3.53 ppm (2H, s), 3.81~3.82 ppm (4H, t), 3.91 ppm (3H, s), 5.81 ppm (1H, d), 6.36~6.42 ppm (1H, d), 6.69~6.78 ppm (1H, q), 6.96 ppm (1H, s), 7.34 ppm (1H, d), 7.36~7.51 ppm (3H, m), 8.07 ppm (2H, d), 8.19 ppm (1H, s), 8.54 ppm (1H, d), 9.06 ppm (1H, s), 9.14 ppm (2H, d).

Example 93

Compound 93: N-(5-(4-(4-((dimethylamino)methyl)-3-isopropyl-1H-pyrazol-1-yl)pyrimidin-2-ylamino)-4-methoxy-2-morpholinophenyl)acrylamide Using Intermediate 84 and dimethylamine, the title compound was prepared as described in Example 1; MS (ESI) m/z 521.3 [M+H]$^+$.

Example 94

Compound 94: N-(5-(4-(4-((dimethylamino)methyl)-3-phenyl-1H-pyrazol-1-yl)pyrimidin-2-ylamino)-4-methoxy-2-(2-methoxyethyl)(methyl)amino)phenyl)acrylamide Using Intermediate 85 and dimethylamine, the title compound was prepared as described in Example 1; MS (ESI) m/z 557.3 $[M+H]^+$.

Example 95

Compound 95: N-(5-(4-(4-(azetidin-1-ylmethyl)-3-phenyl-1H-pyrazol-1-yl)pyrimidin-2-ylamino)-4-methoxy-2-((2-methoxyethyl)(methyl)amino)phenyl)acrylamide Using Intermediate 85 and azetidine hydrochloride, the title compound was prepared as described in Example 1; MS (ESI) m/z 569.3 $[M+H]^+$.

Example 96

Compound 96: N-(5-(4-(4-((dimethylamino)methyl)-3-phenyl-1H-pyrazol-1-yl)pyrimidin-2-ylamino)-4-methoxy-2-(methyl(oxetan-3-yl)amino)phenyl)acrylamide Using Intermediate 86 and dimethylamine, the title compound was prepared as described in Example 1; MS (ESI) m/z 555.3 $[M+H]^+$.

$^1$H NMR: δ (DMSO-$d_6$), 2.22 ppm (6H, s), 3.47 ppm (2H, s), 3.87 ppm (3H, s), 4.42~4.49 ppm (3H, m), 4.61~4.65 ppm (2H, t), 5.83 ppm (1H, d), 6.40~6.46 ppm (1H, dd), 6.73 ppm (1H, s), 6.78~6.87 ppm (1H, q), 7.35 ppm (1H, d), 7.40~7.52 ppm (3H, m), 8.05 ppm (2H, d), 8.18 ppm (1H, s), 8.54 ppm (1H, d), 9.12 ppm (2H, d), 9.30 ppm (1H, s).

Example 97

Compound 97: N-(5-(4-(4-(azetidin-1-ylmethyl)-3-phenyl-1H-pyrazol-1-yl)pyrimidin-2-ylamino)-4-methoxy-2-(methyl(oxetan-3-yl)amino)phenyl)acrylamide Using Intermediate 86 and azetidine hydrochloride, the title compound was prepared as described in Example 1; MS (ESI) m/z 567.3 $[M+H]^+$.

Example 98

Compound 98: N-(5-(4-(4-((dimethylamino)methyl)-3-phenyl-1H-pyrazol-1-yl)pyrimidin-2-ylamino)-4-methoxy-2-(pyrrolidin-1-yl)phenyl)acrylamide Using Intermediate 87 and dimethylamine, the title compound was prepared as described in Example 1; MS (ESI) m/z 539.3 $[M+H]^+$.

Example 99

Compound 99: N-(5-(4-(4-(azetidin-1-ylmethyl)-3-phenyl-1H-pyrazol-1-yl)pyrimidin-2-ylamino)-4-methoxy-2-(pyrrolidin-1-yl)phenyl)acrylamide Using Intermediate 87 and azetidine hydrochloride, the title compound was prepared as described in Example 1; MS (ESI) m/z 551.3 $[M+H]^+$.

Example 100

Compound 100: N-(5-(4-(3-tert-butyl-4-((dimethylamino)methyl)-1H-pyrazol-1-yl)pyrimidin-2-ylamino)-4-methoxy-2-((2-methoxyethyl)(methyl)amino)phenyl)acrylamide Using Intermediate 88 and dimethylamine, the title compound was prepared as described in Example 1; MS (ESI) m/z 537.3 $[M+H]^+$.

Example 101

Compound 101: N-(5-(4-(4-(azetidin-1-ylmethyl)-3-tert-butyl-1H-pyrazol-1-yl)pyrimidin-2-ylamino)-4-methoxy-2-((2-methoxyethyl)(methyl)amino)phenyl)acrylamide Using Intermediate 88 and azetidine hydrochloride, the title compound was prepared as described in Example 1; MS (ESI) m/z 549.3 $[M+H]^+$.

Example 102

Compound 102: N-(5-(4-(3-tert-butyl-4-((dimethylamino)methyl)-1H-pyrazol-1-yl)pyrimidin-2-ylamino)-4-methoxy-2-(methyl(oxetan-3-yl)amino)phenyl)acrylamide Using Intermediate 89 and dimethylamine, the title compound was prepared as described in Example 1; MS (ESI) m/z 535.3 $[M+H]^+$.

Example 103

Compound 103: N-(5-(4-(4-(azetidin-1-ylmethyl)-3-tert-butyl-1H-pyrazol-1-yl)pyrimidin-2-ylamino)-4-methoxy-2-(methyl(oxetan-3-yl)amino)phenyl)acrylamide Using Intermediate 89 and azetidine hydrochloride, the title compound was prepared as described in Example 1; MS (ESI) m/z 547.3 $[M+H]^+$.

Example 104

Compound 104: N-(5-(4-(3-tert-butyl-4-((dimethylamino)methyl)-1H-pyrazol-1-yl)pyrimidin-2-ylamino)-4-methoxy-2-(pyrrolidin-1-yl)phenyl)acrylamide Using Intermediate 90 and dimethylamine, the title compound was prepared as described in Example 1; MS (ESI) m/z 519.3 $[M+H]^+$.

Example 105

Compound 105: N-(5-(4-(4-(azetidin-1-ylmethyl)-3-tert-butyl-1H-pyrazol-1-yl)pyrimidin-2-ylamino)-4-methoxy-2-(pyrrolidin-1-yl)phenyl)acrylamide Using Intermediate 90 and azetidine hydrochloride, the title compound was prepared as described in Example 1; MS (ESI) m/z 531.3 $[M+H]^+$.

Example 106

Compound 106: N-(5-(4-(3-cyclopropyl-4-((dimethylamino)methyl)-1H-pyrazol-1-yl)pyrimidin-2-ylamino)-4-methoxy-2-((2-methoxyethyl)(methyl)amino)phenyl)acrylamide Using Intermediate 91 and dimethylamine, the title compound was prepared as described in Example 1; MS (ESI) m/z 521.3 $[M+H]^+$.

Example 107

Compound 107: N-(5-(4-(4-(azetidin-1-ylmethyl)-3-cyclopropyl-1H-pyrazol-1-yl)pyrimidin-2-ylamino)-4-methoxy-2-((2-methoxyethyl)(methyl)amino)phenyl)acrylamide Using Intermediate 91 and azetidine hydrochloride, the title compound was prepared as described in Example 1; MS (ESI) m/z 533.3 $[M+H]^+$.

Example 108

Compound 108: N-(5-(4-(3-cyclopropyl-4-((dimethylamino)methyl)-1H-pyrazol-1-yl)pyrimidin-2-ylamino)-4-methoxy-2-(methyl(oxetan-3-yl)amino)phenyl)acrylamide Using Intermediate 92 and dimethylamine, the title compound was prepared as described in Example 1; MS (ESI) m/z 519.3 $[M+H]^+$.

Example 109

Compound 109: N-(5-(4-(4-(azetidin-1-ylmethyl)-3-cyclopropyl-1H-pyrazol-1-yl)pyrimidin-2-ylamino)-4-methoxy-2-(methyl(oxetan-3-yl)amino)phenyl)acrylamide Using Intermediate 92 and azetidine hydrochloride, the title compound was prepared as described in Example 1; MS (ESI) m/z 531.3 $[M+H]^+$.

Example 110

Compound 110: N-(5-(4-(3-cyclopropyl-4-((dimethylamino)methyl)-1H-pyrazol-1-yl)pyrimidin-2-ylamino)-4-methoxy-2-(pyrrolidin-1-yl)phenyl)acrylamide Using Intermediate 93 and dimethylamine, the title compound was prepared as described in Example 1; MS (ESI) m/z 503.3 $[M+H]^+$.

Example 111

Compound 111: N-(5-(4-(4-(azetidin-1-ylmethyl)-3-cyclopropyl-1H-pyrazol-1-yl)pyrimidin-2-ylamino)-4-methoxy-2-(pyrrolidin-1-yl)phenyl)acrylamide Using Intermediate 93 and azetidine hydrochloride, the title compound was prepared as described in Example 1; MS (ESI) m/z 515.3 $[M+H]^+$.

Example 112

Compound 112: N-(5-(4-(4-((dimethylamino)methyl)-3-isopropyl-1H-pyrazol-1-yl)pyrimidin-2-ylamino)-4-methoxy-2-((2-methoxyethyl)(methyl)amino)phenyl)acrylamide Using Intermediate 94 and dimethylamine, the title compound was prepared as described in Example 1; MS (ESI) m/z 523.3 $[M+H]^+$.

Example 113

Compound 113: N-(5-(4-(4-(azetidin-1-ylmethyl)-3-isopropyl-1H-pyrazol-1-yl)pyrimidin-2-ylamino)-4-methoxy-2-((2-methoxyethyl)(methyl)amino)phenyl)acrylamide Using Intermediate 94 and azetidine hydrochloride, the title compound was prepared as described in Example 1; MS (ESI) m/z 535.3 $[M+H]^+$.

Example 114

Compound 114: N-(5-(4-(4-((dimethylamino)methyl)-3-isopropyl-1H-pyrazol-1-yl)pyrimidin-2-ylamino)-4-methoxy-2-(methyl(oxetan-3-yl)amino)phenyl)acrylamide Using Intermediate 95 and dimethylamine, the title compound was prepared as described in Example 1; MS (ESI) m/z 521.3 $[M+H]^+$.

Example 115

Compound 115: N-(5-(4-(4-(azetidin-1-ylmethyl)-3-isopropyl-1H-pyrazol-1-yl)pyrimidin-2-ylamino)-4-methoxy-2-(methyl)oxetan-3-yl)amino)phenyl)acrylamide Using Intermediate 95 and azetidine hydrochloride, the title compound was prepared as described in Example 1; MS (ESI) m/z 533.3 $[M+H]^+$.

Example 116

Compound 116: N-(5-(4-(4-((dimethylamino)methyl)-3-isopropyl-1H-pyrazol-1-yl)pyrimidin-2-ylamino)-4-methoxy-2-(pyrrolidin-1-yl)phenyl)acrylamide Using Intermediate 96 and dimethylamine, the title compound was prepared as described in Example 1; MS (ESI) m/z 505.3 $[M+H]^+$.

Example 117

Compound 117: N-(5-(4-(4-(azetidin-1-ylmethyl)-3-isopropyl-1H-pyrazol-1-yl)pyrimidin-2-ylamino)-4-methoxy-2-(pyrrolidin-1-yl)phenyl)acrylamide Using Intermediate 96 and azetidine hydrochloride, the title compound was prepared as described in Example 1; MS (ESI) m/z 517.3 [M+H]$^+$.

Example 118

Compound 118: N-(5-(4-(4-(azetidin-1-ylmethyl)-3-(thiophen-2-yl)-1H-pyrazol-1-yl)pyrimidin-2-ylamino)-4-methoxy-2-morpholinophenyl)acrylamide Using Intermediate 80 and azetidine hydrochloride, the title compound was prepared as described in Example 1; MS (ESI) m/z 573.2 [M+H]$^+$.

Example 119

Compound 119: N-(5-(4-(4-(azetidin-1-ylmethyl)-3-isopropyl-1H-pyrazol-1-yl)pyrimidin-2-ylamino)-4-methoxy-2-morpholinophenyl)acrylamide Using Intermediate 84 and azetidine hydrochloride, the title compound was prepared as described in Example 1; MS (ESI) m/z 533.3 [M+H]$^+$.

Example 120

Compound 120: N-(5-(4-(4-((dimethylamino)methyl)-3-phenyl-1H-pyrazol-1-yl)-5-methylpyrimidin-2-ylamino)-4-methoxy-2-morpholinophenyl)acrylamide Using Intermediate 98 and dimethylamine, the title compound was prepared as described in Example 1; MS (ESI) m/z 569.3 [M+H]$^+$.

Example 121

Compound 121: N-(5-(4-(4-(azetidin-1-ylmethyl)-3-phenyl-1H-pyrazol-1-yl)-5-methylpyrimidin-2-ylamino)-4-methoxy-2-morpholinophenyl)acrylamide Using Intermediate 98 and azetidine hydrochloride, the title compound was prepared as described in Example 1; MS (ESI) m/z 581.3 [M+H]$^+$.

Example 122

Compound 122: N-(5-(4-(3-cyclopropyl-4-((dimethylamino)methyl)-1H-pyrazol-1-yl)-5-methylpyrimidin-2-ylamino)-4-methoxy-2-morpholinophenyl)acrylamide Using Intermediate 100 and dimethylamine, the title compound was prepared as described in Example 1; MS (ESI) m/z 533.3 [M+H]$^+$. $^1$H NMR (500 MHz, DMSO-d$_6$) δ ppm 0.89-0.96 (m, 4H), 2.05-2.09 (m, 1H), 2.30 (br s, 4H), 2.46 (s, 3H), 2.85-2.87 (m, 4H), 3.18 (br s, 4H), 3.82 (t, J=4.5 Hz, 4H), 3.90 (s, 3H), 5.79 (dd, J=1.5, 10.0 Hz, 1H), 6.33 (dd, J=1.5, 17 Hz, 1H), 6.64-6.69 (m, 1H), 6.95 (s, 1H), 7.88 (s, 1H), 8.35 (s, 1H), 8.85 (s, 1H), 8.90 (s, 1H), 9.03 (s, 1H).

Example 123

Compound 123: N-(5-(4-(4-(azetidin-1-ylmethyl)-3-cyclopropyl-1H-pyrazol-1-yl)-5-methylpyrimidin-2-ylamino)-4-methoxy-2-morpholinophenyl)acrylamide Using Intermediate 100 and azetidine hydrochloride, the title compound was prepared as described in Example 1; MS (ESI) m/z 545.3 [M+H]$^+$.

Example 124

Compound 124: N-(5-(4-(4-((dimethylamino)methyl)-3-isopropyl-1H-pyrazol-1-yl)-5-methylpyrimidin-2-ylamino)-4-methoxy-2-morpholinophenyl)acrylamide Using Intermediate 4 and dimethylamine, the title compound was prepared as described in Example 1; MS (ESI) m/z 535.3 [M+H]$^+$.

Example 125

Compound 125: N-(5-(4-(4-(azetidin-1-ylmethyl)-3-isopropyl-1H-pyrazol-1-yl)-5-methylpyrimidin-2-ylamino)-4-methoxy-2-morpholinophenyl)acrylamide Using Intermediate 4 and azetidine hydrochloride, the title compound was prepared as described in Example 1; MS (ESI) m/z 547.3 [M+H]$^+$.

Example 126

Compound 126: N-(5-(4-(3-tert-butyl-4-((dimethylamino)methyl)-1H-pyrazol-1-yl)pyrimidin-2-ylamino)-2-(ethyl(2-methoxyethyl)amino)-4-methoxyphenyl)acrylamide Using Intermediate 101 and dimethylamine hydrochloride, the title compound was prepared as described in Example 1; MS (ESI) m/z 551.3 [M+H]$^+$.

Example 127

Compound 127: N-(5-(4-(4-((dimethylamino)methyl)-3-(furan-3-yl)-1H-pyrazol-1-yl)pyrimidin-2-ylamino)-4-methoxy-2-morpholinophenyl)acrylamide Using Intermediate 102 and dimethylamine hydrochloride, the title compound was prepared as described in Example 1; MS (ESI) m/z 545.3 [M+H]$^+$.

Example 128

Compound 128: N-(5-(4-(4-((dimethylamino)methyl)-3-(pyridin-3-yl)-1H-pyrazol-1-yl)pyrimidin-2-ylamino)-4-methoxy-2-morpholinophenyl)acrylamide Using Intermediate 103 and dimethylamine hydrochloride, the title compound was prepared as described in Example 1; MS (ESI) m/z 556.3 [M+H]$^+$.

Example 129

Compound 129: N-(2-(4-acetylpiperazin-1-yl)-5-(4-(3-cyclopropyl-4-((dimethylamino)methyl)-1H-pyrazol-1-yl)pyrimidin-2-ylamino)-4-methoxyphenyl) acrylamide Using Intermediate 104 and dimethylamine hydrochloride, the title compound was prepared as described in Example 1; MS (ESI) m/z 560.3 [M+H]$^+$.

Example 130

Compound 130: N-(5-(4-(3-(azetidin-1-ylmethyl)-4-(furan-3-yl)-1H-pyrrol-1-yl)-5-fluoropyrimidin-2-ylamino)-4-methoxy-2-morpholinophenyl)acrylamide Using Intermediate 105 and azetidine hydrochloride, the title compound was prepared as described in Example 1; MS (ESI) m/z 574.3 [M+H]$^+$.

Example 131

Compound 131: N-(5-(4-(3-((dimethylamino)methyl)-4-(furan-3-yl)-1H-pyrrol-1-yl)-5-fluoropyrimidin-2-ylamino)-4-methoxy-2-morpholinophenyl) acrylamide Using Intermediate 105 and dimethylamine hydrochloride, the title compound was prepared as described in Example 1; MS (ESI) m/z 562.3 [M+H]$^+$.

Example 132

Compound 132: N-(5-(4-(3-cyclopropyl-4-((dimethylamino)methyl)-1H-pyrazol-1-yl)-5-methylpyrimidin-2-ylamino)-4-methoxy-2-(methyl(oxetan-3-yl)amino)phenyl)acrylamide Using Intermediate 106 and dimethylamine hydrochloride, the title compound was prepared as described in Example 1; MS (ESI) m/z 533.3 [M+H]$^+$.
$^1$H NMR: δ (DMSO-d$_6$), 0.88~0.93 ppm (5H, m), 2.05~2.06 ppm (2H, m), 2.15 ppm (6H, s), 2.44 ppm (6H, s), 3.43 ppm (2H, s), 3.84 ppm (3H, t), 4.37~4.46 ppm (3H, m), 4.59~4.63 ppm (2H, m), 5.80 ppm (1H, d), 6.33~6.39 ppm (1H, dd), 6.68 ppm (1H, s), 6.69~6.83 ppm (1H, q), 7.94 ppm (1H, s), 8.34 ppm (1H, s), 8.79 ppm (1H, s), 8.94 ppm (1H, s), 9.25 ppm (1H, s).

Example 134

Compound 134: N-(2-(4-acetylpiperazin-1-yl)-5-(4-(4-(azetidin-1-ylmethyl)-3-phenyl-1H-pyrazol-1-yl)pyrimidin-2-ylamino)-4-methoxyphenyl)acrylamide Using Intermediate 107 and azetidine hydrochloride, the title compound was prepared as described in Example 1; MS (ESI) m/z 608.3 [M+H]$^+$.

Example 135

Compound 135: N-(2-(4-acetylpiperazin-1-yl)-5-(4-(4-((dimethylamino)methyl)-3-phenyl-1H-pyrazol-1-yl)pyrimidin-2-ylamino)-4-methoxyphenyl)acrylamide Using Intermediate 107 and dimethylamine hydrochloride, the title compound was prepared as described in Example 1; MS (ESI) m/z 596.3 [M+H]$^+$.
$^1$H NMR: δ (DMSO-d$_6$), 2.06 ppm (3H, s), 2.22 ppm (6H, s), 2.81~2.85 ppm (5H, m), 3.47 ppm (2H, s), 3.67 ppm (4H, t), 3.90 ppm (3H, s), 5.82~5.85 ppm (1H, dd), 6.40~6.45 ppm (1H, d), 6.72~6.84 ppm (1H, q), 6.97 (1H, s), 7.35 ppm (1H, d), 7.42~7.52 ppm (4H, m), 8.05 ppm (1H, d), 8.18 ppm (1H, s), 8.54 ppm (1H, d), 9.13~9.18 ppm (3H, m).

Example 136

Compound 136: N-(5-(4-(4-((dimethylamino)methyl)-3-(pyridin-4-yl)-1H-pyrazol-1-yl)pyrimidin-2-ylamino)-4-methoxy-2-morpholinophenyl)acrylamide Using Intermediate 108 and dimethylamine hydrochloride, the title compound was prepared as described in Example 1; MS (ESI) m/z 556.3 [M+H]$^+$.

Example 137

Compound 137: N-(2-(4-acetylpiperazin-1-yl)-5-(4-(3-cyclopropyl-4-((ethyl(methyl)amino)methyl)-1H-pyrazol-1-yl)pyrimidin-2-ylamino)-4-methoxyphenyl)acrylamide Using Intermediate 104 and N-methylethanamine, the title compound was prepared as described in Example 1; MS (ESI) m/z 574.3 [M+H]$^+$.
$^1$H NMR: δ (DMSO-d$_6$), 0.91~0.95 ppm (5H, m), 1.04 ppm (3H, t), 2.05 ppm (6H, s), 2.17 ppm (3H, s), 2.80~2.84 ppm (5H, m), 3.55~3.57 ppm (2H, m), 3.66 ppm (4H, t), 3.88 ppm (3H, s), 5.80 ppm (1H, d), 6.33~6.39 ppm (1H, dd), 6.69~6.78 ppm (1H, q), 6.94 (1H, s), 7.11 ppm (1H, d), 8.09 ppm (1H, s), 8.44 ppm (1H, d), 8.91 ppm (1H, s), 9.05 ppm (1H, s), 9.14 ppm (1H, s).

Example 138

Compound 138: N-(2-(4-acetylpiperazin-1-yl)-5-(4-(4-(azetidin-1-ylmethyl)-3-cyclopropyl-1H-pyrazol-1-yl)pyrimidin-2-ylamino)-4-methoxyphenyl)acrylamide Using Intermediate 106 and azetidine hydrochloride, the title compound was prepared as described in Example 1; MS (ESI) m/z 572.3 [M+H]$^+$.
$^1$H NMR: δ (DMSO-d$_6$), 0.81~0.95 ppm (5H, m), 1.93 ppm (3H, t), 2.06 ppm (3H, s), 2.80~2.84 ppm (5H, m), 3.11 ppm (4H, t), 3.51 ppm (3H, s), 3.61~3.72 ppm (6H, m), 3.82~3.92 ppm (5H, m), 5.84 ppm (1H, d), 6.41~6.46 ppm (1H, d), 6.72~6.81 ppm (1H, q), 6.94 (1H, s), 7.10 ppm (1H, d), 8.09 ppm (1H, s), 8.43 ppm (1H, d), 8.86 ppm (1H, s), 9.05 ppm (1H, s), 9.16 ppm (1H, s).

Example 139

Compound 139: N-(2-(azetidin-1-yl)-5-(4-(4-(azetidin-1-ylmethyl)-3-cyclopropyl-1H-pyrazol-1-yl)pyrimidin-2-ylamino)-4-methoxyphenyl)acrylamide Using Intermediate 109 and azetidine hydrochloride, the title compound was prepared as described in Example 1; MS (ESI) m/z 501.3 [M+H]$^+$.
$^1$H NMR: δ (DMSO-d$_6$), 0.88~0.93 ppm (5H, m), 1.92~1.99 ppm (3H, m), 2.21 ppm (3H, t), 3.11 ppm (4H, t), 3.48 ppm (2H, s), 3.80~3.88 ppm (9H, m), 5.73 ppm (1H, d), 6.22 ppm (1H, s), 6.29~6.34 ppm (1H, d), 6.49~6.52 ppm (1H, q), 6.99 (1H, d), 7.90 ppm (1H, s), 8.06 ppm (1H, s), 8.36 ppm (1H, d), 8.48 ppm (1H, s), 9.29 ppm (1H, s).

Example 140

Compound 140: N-(5-(4-(3-cyclopropyl-4-((ethyl(methyl)amino)methyl)-1H-pyrazol-1-yl)pyrimidin-2-ylamino)-4-methoxy-2-morpholinophenyl)acrylamide Using Intermediate 39 and N-ethylmethylamine, the title compound was prepared as described in Example 1; MS (ESI) m/z 533.3 [M+H]$^+$.

$^1$H NMR: δ (DMSO-d$_6$), 0.91~0.94 ppm (4H, m), 1.03 ppm (3H, t), 2.07~2.14 ppm (4H, m), 2.83~2.85 ppm (4H, t), 3.50 ppm (2H, s), 3.79~3.81 ppm (4H, t), 3.89 ppm (3H, s), 5.76~5.82 ppm (1H, dd), 6.32~6.38 ppm (1H, dd), 6.67~6.76 ppm (1H, q), 6.93 (1H, s), 7.11 ppm (1H, d), 8.08 ppm (1H, s), 8.43 ppm (1H, d), 8.88 ppm (1H, s), 8.99 ppm (1H, s), 9.12 ppm (1H, s).

Example 141

Compound 141: N-(2-(azetidin-1-yl)-5-(4-(3-(azetidin-1-ylmethyl)-4-methyl-1H-pyrrol-1-yl)-5-fluoropyrimidin-2-ylamino)-4-methoxyphenyl)acrylamide Using Intermediate 110 and azetidine hydrochloride, the title compound was prepared as described in Example 1; MS (ESI) m/z 492.2 [M+H]$^+$.

Example 142

Compound 142: N-(5-(4-(3-(azetidin-1-ylmethyl)-4-methyl-1H-pyrrol-1-yl)-5-fluoropyrimidin-2-ylamino)-2-(dimethylamino)-4-methoxyphenyl)acrylamide Using Intermediate 111 and azetidine hydrochloride, the title compound was prepared as described in Example 1; MS (ESI) m/z 480.4 [M+H]$^+$.

Example 143

Compound 143: N-(2-(dimethylamino)-5-(4-(3-((dimethylamino)methyl)-4-methyl-1H-pyrrol-1-yl)-5-fluoropyrimidin-2-ylamino)-4-methoxyphenyl)acrylamide Using Intermediate 111 and dimethylamine hydrochloride, the title compound was prepared as described in Example 1; MS (ESI) m/z 468.2 [M+H]$^+$.

Example 144

Compound 144: N-(2-((2-(dimethylamino)ethyl)(methyl)amino)-5-(4-(3-((dimethylamino)methyl)-4-(trifluoromethyl)-1H-pyrrol-1-yl)-5-fluoropyrimidin-2-ylamino)-4-methoxyphenyl)acrylamide Using Intermediate 113 and dimethylamine hydrochloride, the title compound was prepared as described in Example 1; MS (ESI) m/z 578.3 [M+H]$^+$.

Example 145

Compound 145: N-(5-(4-(4-((ethyl(methyl)amino)methyl)-3-methyl-1H-pyrazol-1-yl)pyrimidin-2-ylamino)-4-methoxy-2-morpholinophenyl)acrylamide Using Intermediate 13 and N-ethylmethylamine, the title compound was prepared as described in Example 1; MS (ESI) m/z 507.4 [M+H]$^+$.

Comparative Example 1

Compound 146: 4-(3-((dimethylamino)methyl)-4-methyl-1H-pyrrol-1-yl)-N-(3,5-dimethylphenyl)pyrimidin-2-amine Compound 146 was prepared as described in U.S. Pat. No. 8,626,132 B2; MS (ESI) m/z 356.4 [M+H]$^+$.

Comparative Example 2

Compound 147: 1-((1-(2-(3,5-dimethylphenylamino)pyrimidin-4-yl)-3-methyl-1H-pyrazol-4-yl)methyl)azetidin-3-ol Compound 147 was prepared as described in U.S. Pat. No. 8,626,132 B2; MS (ESI) m/z 365.3 [M+H]$^+$.

Comparative Example 3

Compound 148: (R)-1-((1-(2-(3,5-dimethyl-4-(2-(pyrrolidin-1-yl)ethoxy)phenylamino)pyrimidin-4-yl)-3-methyl-1H-pyrazol-4-yl)methyl)pyrrolidin-3-ol Compound 148 was prepared as described in U.S. Pat. No. 8,626,132 B2; MS (ESI) m/z 492.5 [M+H]$^+$.

Comparative Example 4

Compound 149: 1-((1-(2-(4-(2-hydroxyethoxy)-3,5-dimethylphenylamino)pyrimidin-4-yl)-3-methyl-1H-pyrazol-4-yl)methyl)azetidin-3-ol Compound 149 was prepared as described in U.S. Pat. No. 8,626,132 B2; MS (ESI) m/z 425.4 [M+H]$^+$.

Comparative Example 5

Compound 150: 1-((4-methyl-1-(2-(2-methylbiphenyl-4-ylamino)pyrimidin-4-yl)-1H-pyrrol-3-yl)methyl)azetidin-3-ol Compound 150 was prepared as described in U.S. Pat. No. 8,626,132 B2; MS (ESI) m/z 426.3 [M+H]$^+$.

Comparative Example 6

Compound 151: 1-((3-cyclopropyl-1-(2-(4-(2-hydroxyethoxy)-3,5-dimethylphenylamino)pyrimidin-4-yl)-1H-pyrazol-4-yl)methyl)azetidin-3-ol Compound 151 was prepared as described in U.S. Pat. No. 8,626,132 B2; MS (ESI) m/z 451.5 [M+H]$^+$.

Comparative Example 7

Compound 152: 4-(4-((dimethylamino)methyl)-3-phenyl-1H-pyrazol-1-yl)-N-(2-methoxy-4-morpholino-5-nitrophenyl)pyrimidin-2-amine Using Intermediate 64, compound 152 was prepared as described in the preparation of example 1; MS (ESI) m/z 531.2 [M+H]$^+$.

Comparative Example 8

Compound 153: N1-(4-(4-((dimethylamino)methyl)-3-phenyl-1H-pyrazol-1-yl)pyrimidin-2-yl)-6-methoxy-4-morpholinobenzene-1,3-diamine Using compound 152, compound 153 was prepared as described in the preparation of example 1; MS (ESI) m/z 501.4 [M+H]$^+$.

Comparative Example 9

Compound 154: N-(5-(4-(4-((dimethylamino)methyl)-3-phenyl-1H-pyrazol-1-yl)pyrimidin-2-ylamino)-4-methoxy-2-morpholinophenyl)but-3-enamide Using compound 153, compound 154 was prepared as described in the preparation of example 1; MS (ESI) m/z 569.3 [M+H]$^+$.

Comparative Example 10

Compound 155: (E)-N-(5-(4-(4-((dimethylamino)methyl)-3-phenyl-1H-pyrazol-1-yl)pyrimidin-2-ylamino)-4-methoxy-2-morpholinophenyl)pent-2-enamide Using compound 153, compound 155 was prepared as described in the preparation of example 1; MS (ESI) m/z 583.3 [M+H]$^+$.

Comparative Example 11

Compound 156: (Z)—N-(5-(4-(4-((dimethylamino)methyl)-3-phenyl-1H-pyrazol-1-yl)pyrimidin-2-ylamino)-4-methoxy-2-morpholinophenyl)hex-3-enamide Using compound 153, compound 157 was prepared as described in the preparation of example 1; MS (ESI) m/z 597.3 [M+H]$^+$.

Comparative Example 12

Compound 157: N-(5-(4-(4-((dimethylamino)methyl)-3-phenyl-1H-pyrazol-1-yl)pyrimidin-2-ylamino)-4-methoxy-2-morpholinophenyl)propionamide Using compound 153, compound 157 was prepared as described in the preparation of example 1; MS (ESI) m/z 557.7 [M+H]$^+$.

Comparative Example 13

Compound 158: N-(5-(4-(4-(azetidin-1-ylmethyl)-3-phenyl-1H-pyrazol-1-yl)pyrimidin-2-ylamino)-4-methoxy-2-morpholinophenyl)propionamide Using compound 153, compound 158 was prepared as described in the preparation of example 1; MS (ESI) m/z 569.7 [M+H]$^+$.

Comparative Example 14

Compound 159: N-(5-(4-(4-(azetidin-1-ylmethyl)-3-phenyl-1H-pyrazol-1-yl)pyrimidin-2-ylamino)-4-methoxy-2-morpholinophenyl)-2-fluoroacrylamide Using compound 153, compound 159 was prepared as described in the preparation of example 1; MS (ESI) m/z 585.6 [M+H]$^+$.

BIOLOGICAL ASSAYS

1. Kinase Inhibition Assays

Compounds of the present invention were assayed to measure their capacity to inhibit a kinase panel which includes SYK, KDR, JAK3, and EGFR mutants.

Method: Inhibition of Enzymatic Activity of SYK, KDR, JAK3, and EGFR Mutant Kinase Compounds of the invention were initially diluted to 10 mM in 100% DMSO for storage and made into kinase buffer solution to create a compound concentration ranging from 1 uM and 10 uM. Serial dilutions of compounds of the invention were dispensed into the 96-well plate (Greiner Biosciences™) at 6 μL each. The first generation reversible inhibitor Erlotinb and the irreversible inhibitor Afatinib were used as reference compound. Purified human, full-length SYK, KDR, and truncated human JAK3, EGFR mutants such as del E746-A750, L858R, L858R/T790M and del E746-A750/T790M (Carna Biosciences™), were diluted in kinase buffer and added to the compound solutions and pre-incubated for 30 minutes (EGFR mutants for 2 hours) at room temperature. Next, ATP (Teknova™) of approximate ATP concentration (1 mM for EGFR mutants) and substrate solution (Ulight™-TK peptide for SYK, Ulight™-Jak1 for KDR and JAK3, and Ulight™-PolyGT for EGFR mutants (PerkinElmer™)) was added (12 μL each) to the wells containing the compound solution and enzyme and incubated for 1 hour. Following the incubation, the stop solution made with EDTA, water, and Lance detection buffer (PerkinElmer™) was added (12 μL each) to the reaction mixture to stop the phosphorylation. Following the addition of the stop solution and 5 minutes of shaking, the detection solution containing the Europium-labeled antibody, water, and Lance detection buffer was added (12 μL each) to the reaction mixture and incubated again for 50 minutes. Substrate phosphorylation was a function of the 665 nm emission measured following the addition of the detection solution and 50 minutes of incubation.

The potency of compound was assigned as <20 nM in $IC_{50}$, 21 to 200 nM in $IC_{50}$, 201 to 1000 nM in $IC_{50}$ and >1000 nM in $IC_{50}$. The $IC_{50}$ value was determined by GraphPad Prism 5.

Result

Compounds of Formula (I) exhibited useful pharmacological properties. As used herein, the half maximal inhibitory concentration (IC$_{50}$) indicates 50% inhibition on the given kinase activity (e.g., 0% inhibition in control treated with no inhibitor) by the compounds of Formula (I). Compounds of Formula (I) exhibited various levels of inhibition of the given protein kinase on the panel. Certain compounds exhibited a potent inhibition of all test EGFR mutants and good selectivity over other kinases, KDR and SYK as shown in Tables 1 to 5.

For example, Compound 73 of Formula (I), namely, N-(5-(4-(4-((dimethylamino)methyl)-3-phenyl-1H-pyrazol-1-yl)pyrimidin-2-ylamino)-4-methoxy-2-morpholinophenyl)acrylamide, was shown to potently inhibit the kinase activity of JAK3 and all four EGFR mutants at the 1 mM ATP concentration (<20 nM in IC$_{50}$) but to poorly inhibit that of SYK and KDR at approximate ATP Km concentration (see Tables 1 to 5).

Reference compound Erlotinib shows moderate inhibition against EGFR Del E746-A750 mutant and EGFR L858R mutant (20-200 nM in IC$_{50}$) but no or little inhibition against other EGFR mutants, SYK, KDR and JAK3 (>1000 nM in IC$_{50}$). The irreversible inhibitors Afatinib displayed potent inhibition against all EGFR mutants and JAK3 (<20 nM in IC$_{50}$) but no or little inhibition against SYK and KDR (>1000 nM in IC$_{50}$). Therefore, some compounds of Formula (I) displayed strong potency and kinase selectivity similar to the compound 73 and those are equally similar to the irreversible inhibitor Afatinib in terms of potency against all test EGFR mutants. However, unlike Afatinib inhibiting both EGFR mutants and wildtype, some of Formula (I) including compound 73 shows no or little inhibition against EGFR wildtype (see Table 1, Table 2 and FIG. 1), suggesting that they are selective to EGFR wildtype. In addition, potent and selective inhibition (<20 nM) of JAK3 by some of compounds of Formula (I) indicate that they could be therapeutically valuable to treat JAK3 mediated diseases such as rheumatoid arthritis, immune diseases, leukemia, lymphoma and metastatic cancer.

TABLE 1

The kinase potency EGFR mutant(T790M) by the representative compounds of Formula (I).
Biochemical potency: <20 nM, 20-200 nM, 201-1000 nM and >1000 nM

| Compound No | EGFR mutant T790M |
| --- | --- |
| Afatinib | <20 |
| Erlotinib | 20-200 |
| 6 | 20-200 |
| 7 | <20 |
| 9 | 20-200 |
| 11 | <20 |
| 14 | <20 |
| 15 | <20 |
| 16 | 20-200 |
| 17 | <20 |
| 18 | <20 |
| 19 | <20 |
| 20 | <20 |
| 21 | <20 |
| 22 | <20 |
| 23 | 201-1000 |
| 24 | <20 |
| 25 | <20 |
| 26 | <20 |
| 27 | <20 |
| 28 | <20 |
| 29 | <20 |
| 30 | <20 |
| 31 | <20 |

TABLE 1-continued

The kinase potency EGFR mutant(T790M) by the representative compounds of Formula (I).
Biochemical potency: <20 nM, 20-200 nM, 201-1000 nM and >1000 nM

| Compound No | EGFR mutant T790M |
| --- | --- |
| 32 | <20 |
| 33 | <20 |
| 34 | <20 |
| 36 | <20 |
| 37 | <20 |
| 38 | <20 |
| 40 | <20 |
| 41 | <20 |
| 42 | <20 |
| 43 | <20 |
| 44 | 201-1000 |
| 45 | 20-200 |
| 46 | <20 |
| 47 | <20 |
| 48 | <20 |
| 49 | <20 |
| 50 | <20 |
| 51 | <20 |
| 52 | <20 |
| 53 | 20-200 |
| 54 | <20 |
| 55 | <20 |
| 56 | <20 |
| 58 | 20-200 |
| 59 | <20 |
| 60 | 20-200 |
| 61 | <20 |
| 62 | <20 |
| 63 | 20-200 |
| 64 | <20 |
| 65 | 201-1000 |
| 66 | 20-200 |
| 67 | 20-200 |
| 71 | <20 |
| 72 | 20-200 |
| 73 | <20 |
| 74 | <20 |
| 75 | <20 |
| 76 | <20 |
| 77 | <20 |
| 78 | <20 |
| 79 | <20 |
| 80 | <20 |
| 81 | 201-1000 |
| 83 | <20 |
| 84 | <20 |
| 85 | <20 |
| 86 | 20-200 |
| 87 | <20 |
| 88 | <20 |
| 89 | 20-200 |
| 91 | 201-1000 |
| 92 | <20 |
| 93 | <20 |
| 94 | <20 |
| 95 | <20 |
| 96 | 20-200 |
| 97 | 20-200 |
| 98 | 20-200 |
| 99 | 20-200 |
| 100 | 20-200 |
| 101 | <20 |
| 102 | <20 |
| 103 | <20 |
| 104 | <20 |
| 105 | 20-200 |
| 106 | <20 |
| 107 | <20 |
| 108 | <20 |
| 109 | <20 |
| 111 | 20-200 |
| 112 | <20 |

TABLE 1-continued

The kinase potency EGFR mutant(T790M) by the representative compounds of Formula (I).
Biochemical potency: <20 nM, 20-200 nM, 201-1000 nM and >1000 nM

| Compound No | EGFR mutant T790M |
|---|---|
| 113 | <20 |
| 114 | <20 |
| 115 | <20 |
| 116 | <20 |
| 117 | <20 |
| 118 | <20 |
| 119 | <20 |
| 120 | <20 |
| 121 | <20 |
| 122 | <20 |
| 123 | <20 |
| 124 | <20 |
| 125 | <20 |
| 126 | 20-200 |
| 127 | <20 |
| 128 | <20 |
| 129 | <20 |
| 130 | <20 |
| 131 | <20 |
| 132 | <20 |
| 134 | <20 |
| 135 | <20 |
| 136 | <20 |
| 137 | <20 |
| 138 | <20 |
| 139 | <20 |
| 140 | <20 |
| 141 | <20 |
| 143 | <20 |
| 144 | <20 |
| 145 | 20-200 |
| 146 | >1000 |
| 147 | >1000 |
| 148 | >1000 |
| 149 | >1000 |
| 150 | >1000 |
| 151 | >1000 |
| 152 | >1000 |
| 153 | >1000 |
| 157 | >1000 |
| 158 | >1000 |
| 159 | >1000 |

TABLE 2

The kinase potency EGFR mutants by the representative compounds of Formula (I).
Biochemical potency: <20 nM, 20-200 nM, 201-1000 nM and >1000 nM

| Compound No | Del19 (E746-A750) | L858R | L858R/T790M | Del19/T790M |
|---|---|---|---|---|
| Afatinib | <20 | <20 | <20 | <20 |
| Erlotinib | 20-200 | 20-200 | >1000 | >1000 |
| 6 | 20-200 | 20-200 | <20 | <20 |
| 7 | <20 | <20 | <20 | <20 |
| 14 | <20 | <20 | <20 | <20 |
| 15 | <20 | <20 | <20 | <20 |
| 17 | <20 | <20 | <20 | <20 |
| 19 | <20 | <20 | <20 | <20 |
| 21 | <20 | 20-200 | <20 | <20 |
| 22 | <20 | 20-200 | <20 | <20 |
| 23 | 201-1000 | | 201-1000 | 201-1000 |
| 25 | <20 | <20 | <20 | <20 |
| 26 | <20 | <20 | <20 | <20 |
| 28 | <20 | <20 | <20 | <20 |
| 29 | <20 | <20 | <20 | <20 |
| 30 | <20 | <20 | <20 | <20 |
| 31 | <20 | <20 | <20 | <20 |
| 32 | <20 | <20 | <20 | <20 |
| 33 | 20-200 | 20-200 | 20-200 | <20 |
| 34 | <20 | 20-200 | <20 | <20 |
| 35 | 201-1000 | 201-1000 | 201-1000 | 20-200 |
| 36 | <20 | <20 | <20 | <20 |
| 37 | <20 | <20 | <20 | <20 |
| 38 | <20 | <20 | <20 | 20-200 |
| 39 | 201-1000 | 201-1000 | 201-1000 | 20-200 |
| 40 | <20 | 20-200 | <20 | <20 |
| 41 | <20 | <20 | <20 | <20 |
| 42 | <20 | 20-200 | <20 | <20 |
| 43 | <20 | <20 | <20 | <20 |
| 44 | 20-200 | 20-200 | 20-200 | 20-200 |
| 45 | <20 | 20-200 | <20 | <20 |
| 46 | <20 | <20 | <20 | <20 |
| 47 | <20 | <20 | <20 | <20 |
| 48 | <20 | 20-200 | <20 | <20 |
| 49 | <20 | <20 | <20 | <20 |
| 50 | <20 | 20-200 | <20 | <20 |
| 51 | 20-200 | 20-200 | <20 | <20 |
| 52 | <20 | <20 | <20 | <20 |
| 53 | | 20-200 | 20-200 | |
| 54 | <20 | 20-200 | <20 | <20 |
| 55 | <20 | <20 | <20 | <20 |
| 56 | <20 | <20 | <20 | <20 |
| 59 | <20 | <20 | <20 | <20 |
| 60 | <20 | 20-200 | <20 | <20 |
| 61 | 20-200 | 20-200 | 20-200 | |
| 62 | <20 | <20 | <20 | <20 |
| 63 | 20-200 | 201-1000 | 20-200 | |
| 64 | <20 | 20-200 | <20 | <20 |
| 65 | <20 | 20-200 | <20 | <20 |
| 66 | <20 | 20-200 | <20 | |
| 67 | <20 | <20 | <20 | <20 |
| 68 | 20-200 | 201-1000 | 20-200 | 20-200 |
| 69 | <20 | 20-200 | 20-200 | <20 |
| 70 | 20-200 | 20-200 | 20-200 | 20-200 |
| 71 | <20 | <20 | <20 | <20 |
| 73 | <20 | <20 | <20 | <20 |
| 74 | <20 | <20 | <20 | <20 |
| 75 | <20 | <20 | <20 | <20 |
| 76 | <20 | <20 | <20 | <20 |
| 77 | <20 | <20 | <20 | <20 |
| 78 | <20 | <20 | <20 | <20 |
| 79 | <20 | <20 | <20 | <20 |
| 80 | <20 | <20 | <20 | <20 |
| 81 | 20-200 | 20-200 | 20-200 | 20-200 |
| 82 | <20 | 20-200 | <20 | <20 |
| 83 | <20 | <20 | <20 | <20 |
| 84 | <20 | <20 | <20 | <20 |
| 85 | <20 | 20-200 | 20-200 | |
| 86 | <20 | <20 | <20 | <20 |
| 87 | <20 | <20 | <20 | <20 |
| 88 | <20 | <20 | <20 | <20 |
| 89 | 20-200 | 20-200 | <20 | <20 |
| 90 | <20 | 20-200 | <20 | <20 |
| 91 | <20 | 20-200 | 20-200 | |
| 92 | <20 | <20 | <20 | <20 |
| 93 | <20 | <20 | <20 | <20 |
| 94 | <20 | <20 | <20 | <20 |
| 95 | <20 | <20 | <20 | <20 |
| 96 | <20 | <20 | <20 | <20 |
| 97 | 20-200 | <20 | <20 | <20 |
| 98 | <20 | 20-200 | 20-200 | |
| 99 | <20 | 20-200 | 20-200 | |
| 100 | <20 | <20 | <20 | <20 |
| 101 | <20 | <20 | <20 | |
| 102 | <20 | <20 | <20 | |
| 103 | <20 | <20 | <20 | |

TABLE 2-continued

The kinase potency EGFR mutants by the representative compounds of Formula (I).
Biochemical potency: <20 nM, 20-200 nM, 201-1000 nM and >1000 nM

| Compound No | Del19 (E746-A750) | L858R | L858R/T790M | Del19/T790M |
|---|---|---|---|---|
| 106 | <20 | <20 | <20 | <20 |
| 107 | <20 | <20 | <20 | <20 |
| 108 | <20 | <20 | <20 | <20 |
| 109 | <20 | <20 | <20 | <20 |
| 112 | <20 | <20 | <20 | <20 |
| 113 | <20 | <20 | <20 | <20 |
| 114 | <20 | <20 | <20 | <20 |
| 115 | <20 | <20 | <20 | <20 |
| 118 | <20 | <20 | <20 | <20 |
| 119 | <20 | <20 | <20 | <20 |
| 120 | <20 | <20 | <20 | <20 |
| 121 | <20 | <20 | <20 | <20 |
| 122 | <20 | <20 | <20 | <20 |
| 123 | <20 | <20 | <20 | <20 |
| 124 | <20 | <20 | <20 | <20 |
| 125 | <20 | <20 | <20 | <20 |
| 126 | <20 | <20 | <20 | <20 |
| 127 | <20 | <20 | <20 | <20 |
| 128 | <20 | <20 | <20 | <20 |
| 129 | <20 | <20 | <20 | <20 |
| 130 | <20 | <20 | <20 | <20 |
| 131 | <20 | <20 | <20 | <20 |
| 132 | <20 | <20 | <20 | <20 |
| 134 | <20 | <20 | <20 | <20 |
| 135 | <20 | <20 | <20 | <20 |
| 136 | <20 | <20 | <20 | <20 |
| 137 | <20 | <20 | <20 | <20 |
| 138 | <20 | <20 | <20 | <20 |
| 139 | <20 | <20 | <20 | <20 |
| 140 | <20 | <20 | <20 | <20 |
| 141 | <20 | <20 | <20 | <20 |
| 142 | <20 | <20 | <20 | <20 |
| 145 | <20 | <20 | <20 | <20 |
| 146 | >1000 | >1000 | 201-1000 | 201-1000 |
| 147 | >1000 | >1000 | 201-1000 | >1000 |
| 148 | >1000 | >1000 | 201-1000 | 201-1000 |
| 149 | >1000 | >1000 | 201-1000 | >1000 |
| 150 | >1000 | >1000 | 201-1000 | >1000 |
| 151 | >1000 | 20-200 | 20-200 | 201-1000 |
| 152 | >1000 | >1000 | >1000 | >1000 |
| 153 | >1000 | >1000 | >1000 | >1000 |
| 156 | >1000 | >1000 | 201-1000 | 20-200 |
| 157 | >1000 | >1000 | >1000 | >1000 |
| 158 | >1000 | >1000 | >1000 | >1000 |
| 159 | >1000 | >1000 | 20-200 | 20-200 |

TABLE 3

The kinase potency of JAK3 by the representative compounds of Formula (I).
Biochemical potency: <20 nM, 20-200 nM, 201-1000 nM and >1000 nM

| Compound No | JAK3 |
|---|---|
| Afatinib | >1000 |
| Erlotinib | 201-1000 |
| 14 | <20 |
| 17 | <20 |
| 19 | <20 |
| 25 | <20 |
| 26 | <20 |
| 29 | <20 |
| 32 | <20 |
| 34 | 20-200 |
| 36 | <20 |
| 40 | <20 |
| 42 | <20 |
| 46 | <20 |
| 47 | <20 |
| 48 | <20 |
| 49 | <20 |
| 50 | <20 |
| 54 | <20 |
| 55 | <20 |
| 62 | <20 |
| 65 | 20-200 |
| 71 | <20 |
| 73 | <20 |
| 74 | <20 |
| 75 | <20 |
| 76 | <20 |
| 78 | 20-200 |
| 79 | <20 |
| 122 | <20 |
| 123 | <20 |
| 124 | <20 |

TABLE 4

The kinase potency of SYK by the representative compounds of Formula (I).
Biochemical potency: <20 nM, 20-200 nM, 201-1000 nM and >1000 nM

| Compound No | Syk |
|---|---|
| Afatinib | >1000 |
| Erlotinib | >1000 |
| 6 | >1000 |
| 7 | >1000 |
| 9 | >1000 |
| 11 | 20-200 |
| 14 | 201-1000 |
| 15 | 201-1000 |
| 16 | >1000 |
| 17 | 201-1000 |
| 18 | >1000 |
| 19 | 20-200 |
| 20 | 201-1000 |
| 21 | 201-1000 |
| 22 | 20-200 |
| 23 | >1000 |
| 24 | 201-1000 |
| 25 | 201-1000 |
| 26 | 201-1000 |
| 27 | >1000 |
| 28 | 201-1000 |
| 29 | 20-200 |
| 30 | 20-200 |
| 31 | 20-200 |
| 32 | 201-1000 |
| 33 | >1000 |
| 34 | 201-1000 |
| 35 | >1000 |
| 36 | >1000 |
| 37 | 201-1000 |
| 38 | >1000 |
| 39 | >1000 |
| 40 | >1000 |
| 41 | 201-1000 |
| 42 | >1000 |
| 43 | >1000 |
| 44 | >1000 |
| 45 | >1000 |
| 46 | 201-1000 |
| 47 | 201-1000 |
| 48 | 201-1000 |
| 49 | 201-1000 |
| 50 | >1000 |
| 51 | >1000 |

TABLE 4-continued

The kinase potency of SYK by the
representative compounds of Formula (I).
Biochemical potency: <20 nM, 20-200 nM, 201-1000 nM and >1000 nM

| Compound No | Syk |
| --- | --- |
| 52 | 201-1000 |
| 53 | >1000 |
| 54 | >1000 |
| 55 | >1000 |
| 56 | >1000 |
| 58 | 201-1000 |
| 59 | >1000 |
| 60 | >1000 |
| 61 | >1000 |
| 62 | >1000 |
| 63 | >1000 |
| 64 | >1000 |
| 65 | >1000 |
| 66 | >1000 |
| 67 | >1000 |
| 68 | >1000 |
| 69 | >1000 |
| 71 | 201-1000 |
| 73 | 201-1000 |
| 74 | 20-200 |
| 75 | 20-200 |
| 76 | 201-1000 |
| 77 | 201-1000 |
| 78 | >1000 |
| 79 | 201-1000 |
| 80 | >1000 |
| 81 | >1000 |
| 82 | >1000 |
| 83 | >1000 |
| 84 | >1000 |
| 86 | >1000 |
| 87 | >1000 |
| 88 | 201-1000 |
| 90 | >1000 |
| 92 | >1000 |
| 93 | >1000 |
| 94 | >1000 |
| 95 | >1000 |
| 96 | >1000 |
| 97 | >1000 |
| 100 | >1000 |
| 101 | >1000 |
| 102 | >1000 |
| 104 | >1000 |
| 105 | >1000 |
| 106 | 20-200 |
| 107 | 20-200 |
| 108 | 20-200 |
| 109 | >1000 |
| 111 | >1000 |
| 114 | 201-1000 |
| 115 | >1000 |
| 116 | >1000 |
| 117 | >1000 |
| 118 | 20-200 |
| 119 | 201-1000 |
| 120 | 20-200 |
| 122 | 20-200 |
| 123 | 201-1000 |
| 124 | 20-200 |
| 127 | 201-1000 |
| 129 | 201-1000 |
| 130 | 201-1000 |
| 131 | 201-1000 |
| 134 | 201-1000 |
| 135 | >1000 |
| 138 | >1000 |
| 139 | >1000 |
| 140 | >1000 |
| 141 | 201-1000 |
| 142 | 201-1000 |
| 143 | 201-1000 |
| 146 | 20-200 |
| 147 | 20-200 |
| 148 | 201-1000 |
| 149 | >1000 |
| 150 | >1000 |
| 151 | 201-1000 |
| 152 | >1000 |
| 153 | >1000 |
| 156 | >1000 |
| 157 | >1000 |
| 158 | >1000 |
| 159 | >1000 |

TABLE 5

The kinase potency of KDR by the
representative compounds of Formula (I).
Biochemical potency: <20 nM, 20-200 nM, 201-1000 nM and >1000 nM

| Compound No | KDR |
| --- | --- |
| Afatinib | >1000 |
| Erlotinib | 201-1000 |
| 14 | >1000 |
| 17 | 201-1000 |
| 19 | 201-1000 |
| 25 | >1000 |
| 26 | >1000 |
| 29 | >1000 |
| 32 | >1000 |
| 34 | >1000 |
| 36 | >1000 |
| 40 | >1000 |
| 42 | >1000 |
| 46 | >1000 |
| 47 | >1000 |
| 48 | >1000 |
| 49 | >1000 |
| 50 | >1000 |
| 54 | >1000 |
| 55 | >1000 |
| 62 | >1000 |
| 65 | >1000 |
| 71 | >1000 |
| 73 | >1000 |
| 74 | >1000 |
| 75 | >1000 |
| 76 | >1000 |
| 78 | >1000 |
| 79 | >1000 |
| 82 | >1000 |
| 122 | >1000 |
| 123 | >1000 |
| 124 | >1000 |

2. Cell Viability Assay

Compounds of the invention are tested for their effects on NSCLC cell lines to illustrate efficacy of the invention at the cellular level. Mis-regulation and, in particular, over-activation of EGFR mutants have been implicated in increased proliferation of NSCLC lines. Among those cell lines, the cell viability of NSCLC PC9 depends on activation of EGFR del E746-A750 mutant as that of H1975 cell does on activation of EGFR L858R/T790M mutant. And cell viability of H2073 depends on EGFR wildtype.

Therefore, the viability of PC9 by compound of Formula (I) represents cellular potency of test compound against EGFR del E746-A750 mutant and that of H1975 does that against EGFR L858R/T790M mutant. And that of H2073 represents EGFR wildtype potency in NSCLC line.

Method

Compounds of the invention and references were tested against H2073, PC9 and H1975 obtained from the American Type Culture Collection (ATCC, Manassas, Va.). This cell line was maintained with an Roswell Park Memorial Institute (RPMI) medium (GIBCO™) containing 10% fetal bovine serum (FBS; GIBCO™) and 0.05 mM 2-mercaptoethanol. The cells were seeded at $3\times10^3$ cells/100 μL/well into 96 well culture plate, and serially diluted compound was then added. The first generation reversible inhibitor Erlotinb and the irreversible inhibitor Afatinib were used for reference inhibitor. After 72-hour incubation period at 37° C., the cells were subjected to an ATPLite (Promega) assay to determine the cytotoxic effects of compound.

The potency of compound was assigned as <20 nM in $IC_{50}$, 21 to 200 nM in $IC_{50}$, 201 to 1000 nM in $IC_{50}$ and >1000 nM in $IC_{50}$. The $IC_{50}$ value was determined by GraphPad Prism 5.

Result

As used herein, the half maximal inhibitory concentration ($IC_{50}$) indicates 50% inhibition on the given cell's viability by the compounds of Formula (I).

Table 6 shows cellular viability of mutant EGFR expressing cells as compared to wildtype EGFR expressing cell and provides the selectivity ratio of wildtype EGFR expressing cell to mutant expressing cell for each test compound. Compounds of Formula (I) exhibited an potent inhibition range (<20 nM in $IC_{50}$) in PC9 cell and furthermore in H1975 cell where Erlotinib did not show any potent inhibition. For example, Compound 73 of Formula (I), namely, N-(5-(4-(4-((dimethylamino)methyl)-3-phenyl-1H-pyrazol-1-yl)pyrimidin-2-ylamino)-4-methoxy-2-morpholinophenyl)acrylamide, showed potent inhibition in both PC9 and H1975 cell but not in H2073, whereas Afatinib showed potent inhibition in H2073, PC9 and H1975. Unlike Afatinib, some of this invention showed great EGFR wildtype selectivity in cellular level (for example, compound 73 with >200 fold selective in cellular potency shown in Table 6).

TABLE 6

The anti-proliferation activity against H2073, PC9 and H1975 by the selected compounds of Formula (I).
Cellular potency: <20 nM, 20-200 nM, 201-1000 nM and >1000 nM
Fold comparison (selectivity): <20 fold, 20-100 fold, 101-200 fold and >200 fold

| Compound No | EGFR wildtype H2073 (nM) | EGFR Mutants PC9 (nM) | EGFR Mutants H1975 (nM) | Selectivity over wildtype Wildtype vs mutant H2073/PC9 (fold) | Selectivity over wildtype Wildtype vs mutant H2073/H1975 (fold) |
|---|---|---|---|---|---|
| Afatinib | 20-200 | <20 | 20-200 | <20 | <20 |
| Erlotinib | >1000 | 20-200 | >1000 | 20-100 | <20 |
| 14 | >1000 | <20 | 20-200 | >200 | 20-100 |
| 19 | >1000 | <20 | 20-200 | 100-200 | 20-100 |
| 25 | >1000 | <20 | <20 | >200 | 101-200 |
| 26 | >1000 | 20-200 | 20-200 | 20-100 | 101-200 |
| 29 | >1000 | 20-200 | 20-200 | <20 | <20 |
| 32 | >1000 | 201-1000 | 20-200 | 20-100 | 20-100 |
| 36 | >1000 | 20-200 | 20-200 | 20-100 | 20-100 |
| 42 | >1000 | 201-1000 | 20-200 | 20-100 | >200 |

TABLE 6-continued

The anti-proliferation activity against H2073, PC9 and H1975 by the selected compounds of Formula (I).
Cellular potency: <20 nM, 20-200 nM, 201-1000 nM and >1000 nM
Fold comparison (selectivity): <20 fold, 20-100 fold, 101-200 fold and >200 fold

| Compound No | EGFR wildtype H2073 (nM) | EGFR Mutants PC9 (nM) | EGFR Mutants H1975 (nM) | Selectivity over wildtype Wildtype vs mutant H2073/PC9 (fold) | Selectivity over wildtype Wildtype vs mutant H2073/H1975 (fold) |
|---|---|---|---|---|---|
| 46 | >1000 | <20 | 20-200 | >200 | 101-200 |
| 48 | >1000 | 201-1000 | 201-1000 | <20 | <20 |
| 50 | >1000 | 20-200 | 20-200 | 101-200 | >200 |
| 54 | >1000 | 20-200 | 201-1000 | 20-100 | <20 |
| 55 | >1000 | <20 | 20-200 | >200 | 101-200 |
| 62 | >1000 | 20-200 | 20-200 | >200 | >200 |
| 71 | >1000 | <20 | <20 | >200 | >200 |
| 73 | >1000 | <20 | <20 | >200 | >200 |
| 74 | >1000 | <20 | <20 | >200 | >200 |
| 75 | >1000 | 20-200 | 20-200 | 101-200 | 101-200 |
| 76 | >1000 | 20-200 | 20-200 | 101-200 | 101-200 |
| 78 | >1000 | <20 | <20 | >200 | >200 |
| 79 | >1000 | 20-200 | 20-200 | 101-200 | 101-200 |
| 82 | >1000 | 20-200 | 20-200 | 101-200 | 101-200 |
| 84 | 20-200 | <20 | <20 | <20 | <20 |
| 86 | 201-1000 | <20 | <20 | 20-200 | 20-200 |
| 92 | >1000 | <20 | <20 | >200 | >200 |
| 93 | 201-1000 | <20 | <20 | 20-200 | 20-200 |
| 100 | >1000 | 20-200 | 20-200 | 101-200 | 101-200 |
| 106 | >1000 | 20-200 | 20-200 | 101-200 | 101-200 |
| 118 | 201-1000 | <20 | <20 | 20-200 | 20-200 |
| 122 | >1000 | <20 | <20 | >200 | >200 |
| 123 | >1000 | <20 | <20 | >200 | >200 |
| 124 | >1000 | <20 | <20 | >200 | >200 |
| 146 | >1000 | >1000 | >1000 | <20 | <20 |
| 147 | >1000 | >1000 | >1000 | <20 | <20 |
| 148 | >1000 | >1000 | >1000 | <20 | <20 |
| 149 | >1000 | >1000 | >1000 | <20 | <20 |
| 151 | >1000 | >1000 | >1000 | <20 | <20 |
| 154 | >1000 | 20-200 | 201-1000 | <20 | <20 |
| 155 | >1000 | 201-1000 | 201-1000 | <20 | <20 |
| 156 | >1000 | >1000 | >1000 | <20 | <20 |
| 157 | >1000 | >1000 | >1000 | <20 | <20 |
| 158 | >1000 | 20-200 | 201-1000 | <20 | <20 |
| 159 | >1000 | >1000 | >1000 | <20 | <20 |

3. Western Analysis

Compounds of the invention and references are tested for their effects on NSCLC cell lines to measure molecular potency against phosphorylation level of wildtype and mutant EGFR and illustrate selectivity over p-wildtype EGFR. The inhibition level of phosphorylation of mutant EGFR in NSCLC lines PC9 and H1975 should be illustrated to understand whether it is correlated with kinase enzyme potency and cellular potency of the compound. Based on these results, the selectivity of the compound against EGFR mutants over EGFR wildtype can be addressed in physiologically relevant molecular level.

Method

NSCLC lines H1299, PC9, and H1975 were treated with the indicated concentration of compounds for 4 hours. The first generation reversible inhibitor Erlotinib and the irreversible inhibitor Afatinib were used for reference inhibitor. For wild EGFR activation experiment, H1299 cell line was simultaneously treated with addition of 3 nM EGF ligand. Cells were lysed in RIPA buffer (25 mM Tris.HCl pH 7.6, 150 mM NaCl, 1% NP-40, 1% sodium deoxycholate, 0.1% SDS) containing protease and phosphatase inhibitor cocktail (Thermo scientific). Equivalent amounts of protein were separated by NuPAGE 4-12% Bis-Tris Gel system (Invitrogen™), and then transferred to polyvinylidene difluoride membranes. Membranes were probed with an anti-phospho-Y1067 EGFR antibody (Cell Signaling Technology™) and then stripped with Restore Western Blot Stripping Buffer (Thermo Scientific™). Membranes were probed again with an anti-EGFR or anti-actin antibody (Cell Signaling Technology™) for assessing loading control. The membranes were visualized by enhanced chemiluminescence.

To calculate inhibition of phosphorylation level of p-EGFR wildtype, p-EGFR del E746-A750 and p-EGFR L858R/T790M, the intensity of each band treated by indicated concentration of inhibitor was measured by densitometer to translate to numeric value and numeric value of each intensity was compared over that of each actin control at indicated concentration. The $IC_{50}$ value was determined by GraphPad Prism 5.

Result

As used herein, the half maximal inhibitory concentration ($IC_{50}$) indicates 50% inhibition on the given phosphorylation level at Y1068 of each EGFR protein (e.g., p-EGFR wildtype, p-EGFR del E746-A750 and p-EGFR L858R/T790M) by the compounds of Formula (I).

Table 7 shows inhibition of phosphorylation level of mutant EGFR as compared to wildtype EGFR and provides the selectivity ratio of wildtype to mutant for each test compound. Selected compounds of Formula (I) such as compound 26 and 73 exhibited a potent inhibition against p-EGFR del E746-A750 and p-EGFR L858R/T790M but not p-EGFR wildtype (shown in FIG. 1 and Table 7), while Afatinib showed potent inhibition against both p-EGFR wildtype, p-EGFR del E746-A750 and p-EGFR L858R/T790M. While Afatinib revealed 28.7 fold selectivity in p-EGFR del19/p-EGFR wildtype and 9.6 fold selectivity in p-EGFR L858R, T790M/p-EGFR wildtype, compound 26 displayed 572.4 fold and 1440.3 fold selectivity, respectively. Therefore, some of the compounds of the invention showed better EGFR wildtype selectivity in molecular potency level than Afatinib.

TABLE 7

The potency in phosphorylation level of EGFR wildtype and mutants by representative compounds of Formula (I)
Molecular potency: <20 nM, 20-200 nM, 201-1000 nM and >1000 nM
Fold comparison (selectivity): <20 fold, 20-100 fold, 101-200 fold and >200 fold

| | | | | Selectivity over wildtype | |
|---|---|---|---|---|---|
| Compound No | H1299 p-EGFR wild-type | PC9 p-EGFR del 19 (E746-A750) | H1975 p-EGFR L858R, T790M | p-wild-type over p-EGFR del19 | p-wild-type over p-EGFR L858R, T790M |
| Erlotinib | >1000 | <20 | >1000 | 20-100 | n.d. |
| Afatinib | 20-200 | <20 | <20 | 20-100 | <20 |
| 14 | >1000 | <20 | <20 | >200 | 20-100 |
| 26 | >1000 | <20 | <20 | >200 | >200 |
| 46 | 20-200 | <20 | <20 | 20-100 | 20-100 |
| 73 | 201-1000 | <20 | <20 | 20-100 | 20-100 |
| 74 | 201-1000 | <20 | <20 | 101-200 | 20-100 |
| 78 | >1000 | <20 | <20 | >200 | 101-200 |
| 122 | 201-1000 | <20 | <20 | 20-100 | 20-100 |

What is claimed is:
1. A compound of Formula (I):

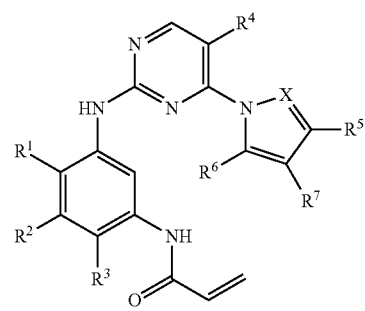

wherein:
X is CH or N;
$R^1$ is H, $R^8$ or —$OR^8$;
$R^2$ is hydrogen, $C_{1-6}$ alkyl, 6-10 membered monocyclic or bicyclic aryl, or 5-10 membered heteroaryl comprising 1-4 heteroatoms selected from N, O and S, wherein the heteroaryl or aryl is optionally and independently substituted at one or more carbon atoms with $R^{13}$; and wherein the heteroaryl having one or more nitrogen atoms is optionally and independently substituted at one or more nitrogen atoms with $R^8$;
$R^3$ is hydrogen, 4-7 membered monocyclic heterocyclyl comprising 1-2 heteroatoms selected from N, O and S, and optionally substituted with oxo, 5-6 membered heteroaryl comprising 1-3 heteroatoms selected from N, O and S, $NR^9R^{10}$, $NR^{11}R^{12}$, or phenyl, wherein the heteroaryl or phenyl is optionally and independently substituted at one or more carbon atoms with $R^{13}$; and wherein the heterocyclyl or heteroaryl having one or more nitrogen atoms is optionally and independently substituted at one or more nitrogen atoms with $R^8$;
$R^4$ is hydrogen, $C_{1-4}$ alkyl, $C_{3-5}$ cycloalkyl, F, Cl, Br, CN, or $CF_3$;
$R^5$ is hydrogen, $CF_3$, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with $R^{13}$;
$R^6$ is hydrogen or $C_{1-6}$ alkyl;
$R^7$ is hydrogen, —$CH_2OH$, —$CH_2OR^8$, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;
$R^8$ is selected from $C_{1-6}$ alkyl or $C_{3-7}$ cycloalkyl;
$R^9$ is selected from $C_{1-6}$ alkyl, $C_{3-7}$ cycloalkyl or 4-7 membered heterocyclyl comprising 1-2 heteroatoms selected from N, O and S, wherein the $C_{1-6}$ alkyl or $C_{3-7}$ cycloalkyl is optionally substituted with halogen or —$OR^8$, and wherein the 4-7 membered heterocyclyl having one nitrogen atom is optionally and independently substituted with —$R^8$, —$C(O)R^8$, —$C(O)OR^8$, or $C(O)NHR^8$;
$R^{10}$ is $C_{1-6}$ alkyl, $C_{3-7}$ cycloalkyl, or $(CH_2)_nNR^9R^9$, wherein each n is independently 1 or 2;
$R^{11}$ and $R^{12}$, taken together with nitrogen atom to which they are bonded form, independently for each occurrence,
i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbons with halogen, hydroxyl, —$OR^8$, —$NR^9R^{10}$, or —$NR^{11}R^{12}$; or ii) a 5-8 membered saturated or partially saturated monocyclic group having 1 or 2 heteroatoms, in addition to the nitrogen atom to which $R^{11}$ and $R^{12}$ are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms with —$R^8$, —$C(O)R^8$, —$C(O)OR^8$, —$C(O)NHR^8$, —$SO_2R^8$, —$SO_2NH_2$, or —$SO_2NR^8_2$; and $R^{13}$ is selected from halogen, CN, $CF_3$, $R^8$, —$OR^8$ or $C_{2-4}$ alkenyl, or a pharmaceutically acceptable salt thereof.

2. The compound of claim 1 or pharmaceutically acceptable salt thereof, wherein said compound is represented by Formula (II):

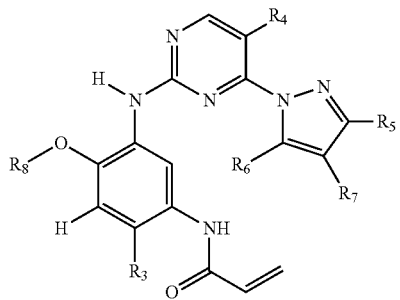

wherein:
$R^3$ is hydrogen, 4-7 membered monocyclic heterocyclyl comprising 1-2 heteroatoms selected from N, O and S, and optionally substituted with oxo, 5-6 membered heteroaryl comprising 1-3 heteroatoms selected from N, O and S, $NR^9R^{10}$, $NR^{11}R^{12}$, or phenyl, wherein the heteroaryl or phenyl is optionally and independently substituted at one or more carbon atoms with $R^{13}$; and wherein the heterocyclyl or heteroaryl having one or more nitrogen atoms is optionally and independently substituted at one or more nitrogen atoms with $R^8$;

$R^4$ is hydrogen, $C_{1-4}$ alkyl, $C_{3-5}$ cycloalkyl, F, Cl, Br, CN, or $CF_3$;

$R^5$ is hydrogen, $CF_3$, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with $R^{13}$;

$R^6$ is hydrogen or $C_{1-6}$ alkyl;

$R^7$ is hydrogen, —$CH_2OH$, —$CH_2OR^8$, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;

$R^8$ is selected from $C_{1-6}$ alkyl or $C_{3-7}$ cycloalkyl;

$R^9$ is selected from $C_{1-6}$ alkyl, $C_{3-7}$ cycloalkyl or 4-7 membered heterocyclyl comprising 1-2 heteroatoms selected from N, O and S, wherein $C_{1-6}$ alkyl or $C_{3-7}$ cycloalkyl is optionally substituted with halogen or —$OR^8$, wherein the 4-7 membered heterocyclyl having one nitrogen atom is optionally and independently substituted with —$R^8$, —$C(O)R^8$, —$C(O)OR^8$, or $C(O)NHR^8$;

$R^{10}$ is $C_{1-6}$ alkyl, $C_{3-7}$ cycloalkyl, or $(CH_2)_nNR^9R^9$, wherein each n is independently 1 or 2;

$R^{11}$ and $R^{12}$, taken together with nitrogen atom to which they are bonded form, independently for each occurrence, i) a 3-8 membered saturated or partially saturated monocyclic group having no heteroatom other than the nitrogen atom to which $R^{11}$ and $R^{12}$ are bonded, wherein said 3-8 membered saturated or partially saturated monocyclic group is optionally and independently substituted at one or more carbons with halogen, hydroxyl, —$OR^8$, —$NR^9R^{10}$, or —$NR^{11}R^{12}$; or ii) a 5-8 membered saturated or partially saturated monocyclic group having 1 or 2 heteroatoms, in addition to the nitrogen atom to which $R^{11}$ and $R^{12}$ are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms with —$R^8$, —$C(O)R^8$, —$C(O)OR^8$, —$C(O)NHR^8$, —$SO_2R^8$, —$SO_2NH_2$, or —$SO_2NR^8_2$; and $R^{13}$ is selected from halogen, CN, $CF_3$, $R^8$, —$OR^8$ or $C_{2-4}$ alkenyl.

3. The compound of claim 1, or pharmaceutically acceptable salt thereof, wherein said compound is represented by Formula (III):

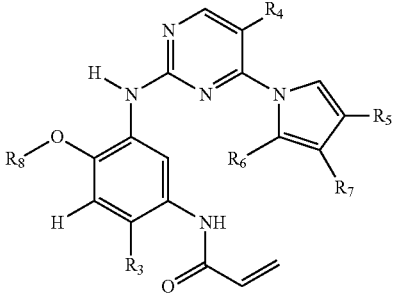

wherein:
$R^3$ is hydrogen, 4-7 membered monocyclic heterocyclyl comprising 1-2 heteroatoms selected from N, O and S, and optionally substituted with oxo, 5-6 membered heteroaryl comprising 1-3 heteroatoms selected from N, O and S, $NR^9R^{10}$, $NR^{11}R^{12}$, or phenyl, wherein the heteroaryl or phenyl is optionally and independently substituted at one or more carbon atoms with $R^{13}$; and wherein the heterocyclyl or heteroaryl having one or more nitrogen atoms is optionally and independently substituted at one or more nitrogen atoms with $R^8$;

$R^4$ is hydrogen, $C_{1-4}$ alkyl, $C_{3-5}$ cycloalkyl, F, Cl, Br, CN, or $CF_3$;

$R^5$ is hydrogen, $CF_3$, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with $R^{13}$;

$R^6$ is hydrogen or $C_{1-6}$ alkyl;

R⁷ is hydrogen, —CH₂OH, —CH₂OR⁸, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;

R⁸ is selected from $C_{1-6}$ alkyl or $C_{3-7}$ cycloalkyl;

R⁹ is selected from $C_{1-6}$ alkyl, $C_{3-7}$ cycloalkyl or 4-7 membered heterocyclyl comprising 1-2 heteroatoms selected from N, O and S, wherein $C_{1-6}$ alkyl or $C_{3-7}$ cycloalkyl is optionally substituted with halogen or —OR⁸, wherein the 4-7 membered heterocyclyl having one nitrogen atom is optionally and independently substituted with —R⁸, —C(O)R⁸, —C(O)OR⁸, or C(O)NHR⁸;

R¹⁰ is $C_{1-6}$ alkyl, $C_{3-7}$ cycloalkyl, or $(CH_2)_nNR^9R^9$, wherein each n is independently 1 or 2;

R¹¹ and R¹², taken together with nitrogen atom to which they are bonded form, independently for each occurrence, i) a 3-8 membered saturated or partially saturated monocyclic group having no heteroatom other than the nitrogen atom to which R¹¹ and R¹² are bonded, wherein said 3-8 membered saturated or partially saturated monocyclic group is optionally and independently substituted at one or more carbons with halogen, hydroxyl, —OR⁸, —NR⁹R¹⁰, or —NR¹¹R¹²; or ii) a 5-8 membered saturated or partially saturated monocyclic group having 1 or 2 heteroatoms, in addition to the nitrogen atom to which R¹¹ and R¹² are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms with —R⁸, —C(O)R⁸, —C(O)OR⁸, —C(O)NHR⁸, —SO₂R⁸, —SO₂NH₂, or —SO₂NR⁸₂; and R¹³ is selected from halogen, CN, CF₃, R⁸, —OR⁸ or $C_{2-4}$ alkenyl.

4. The compound of claim 1 or a pharmaceutically acceptable salt thereof, wherein said compound is represented by Formula (IV):

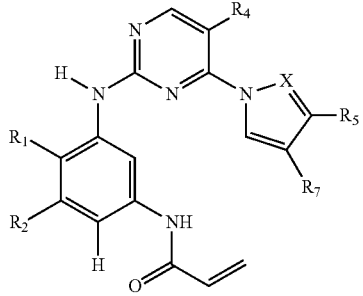

IV wherein:
X is CH or N;
R¹ is H, R⁸ or —OR⁸;
R² is hydrogen, $C_{1-6}$ alkyl, 6-10 membered monocyclic or bicyclic aryl, or 5-10 membered heteroaryl comprising 1-4 heteroatoms selected from N, O and S, wherein the heteroaryl or aryl is optionally and independently substituted at one or more carbon atoms with R¹³; and wherein the heteroaryl having one or more nitrogen atoms is optionally and independently substituted at one or more nitrogen atoms with R⁸;

R⁴ is hydrogen, $C_{1-4}$ alkyl, $C_{3-5}$ cycloalkyl, F, Cl, Br, CN, or CF₃;

R⁵ is hydrogen, CF₃, $C_{1-6}$ alkyl, $C_{3-7}$ cycloalkyl, 5-6 membered heteroaryl comprising 1-3 heteroatoms selected from N, O and S, or 6-10 membered monocyclic or bicyclic aryl, wherein the heteroaryl or aryl is optionally and independently substituted at one or more carbon atoms with R¹³;

R⁷ is hydrogen, —CH₂OH, —CH₂OR⁸, $C_{1-3}$ alkyl, $(CH_2)_nNR^9R^{10}$, $(CH_2)_nNR^{11}R^{12}$, $C(O)NR^9R^{10}$, or $C(O)NR^{11}R^{12}$, wherein each n is independently 1 or 2;

R⁸ is selected from $C_{1-6}$ alkyl or $C_{3-7}$ cycloalkyl;

R⁹ is selected from $C_{1-6}$ alkyl, $C_{3-7}$ cycloalkyl or 4-7 membered heterocyclyl comprising 1-2 heteroatoms selected from N, O and S, wherein $C_{1-6}$ alkyl or $C_{3-7}$ cycloalkyl is optionally substituted with halogen or —OR⁸, wherein the 4-7 membered heterocyclyl having one nitrogen atom is optionally and independently substituted with —R⁸, —C(O)R⁸, —C(O)OR⁸, or C(O)NHR⁸;

R¹⁰ is $C_{1-6}$ alkyl, $C_{3-7}$ cycloalkyl, or $(CH_2)_nNR^9R^9$, wherein each n is independently 1 or 2;

R¹¹ and R¹², taken together with nitrogen atom to which they are bonded form, independently for each occurrence, i) a 3-8 membered saturated or partially saturated monocyclic group having no heteroatom other than the nitrogen atom to which R¹¹ and R¹² are bonded, wherein said 3-8 membered saturated or partially saturated monocyclic group is optionally and independently substituted at one or more carbons with halogen, hydroxyl, —OR⁸, —NR⁹R¹⁰, or —NR¹¹R¹²; or ii) a 5-8 membered saturated or partially saturated monocyclic group having 1 or 2 heteroatoms, in addition to the nitrogen atom to which R¹¹ and R¹² are bonded, wherein said heteroatoms are independently selected from nitrogen, oxygen, sulfur, sulfone or sulfoxide, wherein said 5-8 membered saturated or partially saturated monocyclic group having 1 or 2 nitrogen atoms is optionally substituted at one or more carbon or nitrogen atoms with —R⁸, —C(O)R⁸, —C(O)OR⁸, —C(O)NHR⁸, —SO₂R⁸, —SO₂NH₂, or —SO₂NR⁸₂; and R¹³ is selected from halogen, CN, CF₃, R⁸, —OR⁸ or $C_{2-4}$ alkenyl.

5. The compound of claim 1, wherein R¹ is —OCH₃; R⁴ is H, —CH₃, F, or Cl; R⁵ is hydrogen, $C_{1-6}$ alkyl, $C_{3-7}$ cycloalkyl, pyridinyl, thiophenyl, furanyl, N-methyl pyrrolidinyl, N-methyl pyrazolyl, or phenyl; R⁸ is methyl; and n is 1.

6. The compound of claim 4, wherein R¹ is H; R² is furanyl, thiophenyl, N-methyl pyrazolyl, or phenyl; R⁴ is H, —CH₃, F, or Cl; R⁵ is hydrogen, $C_{1-6}$ alkyl, $C_{3-7}$ cycloalkyl, pyridinyl, thiophenyl, furanyl, N-methyl pyrrolyl, N-methyl pyrazolyl, or phenyl; and n is 1.

7. The compound of claim 5, wherein R² is H; R⁶ is H; R³ is morpholino, N-methyl piperazinyl, piperidinyl, azetidinyl, pyrrodinyl, 4-acetylpiperidinyl, N,N-dimethylamino, 1,4-oxazepan-4-yl, or 4-methyl-1,4,-diazepan-1-yl; and R⁷ is —(CH₂)NR⁹R¹⁰ or —(CH₂)NR¹¹R¹².

8. The compound of claim 6, wherein R⁷ is —(CH₂)NR⁹R¹⁰ or —(CH₂)NR¹¹R¹².

9. The compound of claim 7, wherein R⁹ is methyl, ethyl, propyl, cyclopropylmethyl, or cyclobutylmethyl; and R¹⁰ is methyl, ethyl, propyl, cyclopropylmethyl, oxetanyl, oxethanemethyl, N-methyazetinyl, N,N-dimethylethyl, or methoxyethyl; and NR¹¹R¹² is azetidinyl, 3-hydroxy azetidinyl, 3-methoxy azetidinyl, pyrrolidinyl, (S)-3-hydroxy pyrrolidinyl, (R)-3-hydroxy pyrrolidinyl, (3R,4S)-3,4-dihydroxypyrrolidinyl, (3S,4R)-3-hydroxy-4-methoxypyrrolidinyl, piperidinyl, morpholinyl, N-methylpiperazinyl, azamorpholinyl, N-methylazapiperazinyl, N-acetyl piperazinyl, or thiomorpholinyl.

10. The compound of claim 8, wherein $R^9$ is methyl, ethyl, propyl, cyclopropylmethyl, or cyclobutylmethyl; and $R^{10}$ is methyl, ethyl, propyl, cyclopropylmethyl, oxetanyl, oxethanemethyl, N-methyazetinyl, N,N-dimethylethyl, or methoxyethyl; and $NR^{11}R^{12}$ is azetidinyl, 3-hydroxy azetidinyl, 3-methoxy azetidinyl, pyrrolidinyl, (S)-3-hydroxy pyrrolidinyl, (R)-3-hydroxy pyrrolidinyl, (3R,4S)-3,4-dihydroxypyrrolidinyl, (3S,4R)-3-hydroxy-4-methoxypyrrolidinyl, piperidinyl, morpholinyl, N-methylpiperazinyl, azamorpholinyl, N-methylazapiperazinyl, N-acetyl piperazinyl, or thiomorpholinyl.

11. The compound of claim 5, wherein $R^5$ is hydrogen, methyl, isopropyl, t-butyl, cyclopropyl, 2-thiophenyl, 2-furanyl, 3-furanyl, 3-pyridyl, 4-pyridyl or phenyl.

12. The compound of claim 6, wherein $R^5$ is hydrogen, methyl, isopropyl, t-butyl, cyclopropyl, 2-thiophenyl, 2-furanyl, 3-furanyl, 3-pyridyl, 4-pyridyl or phenyl.

13. The compound of claim 1, selected from:
- N-(3-(4-(4-(azetidin-1-ylmethyl)-3-methyl-1H-pyrazol-1-yl)pyrimidin-2-ylamino)-4-methoxyphenyl)acrylamide,
- N-(3-(4-(4-((3-hydroxyazetidin-1-yl)methyl)-3-methyl-1H-pyrazol-1-yl)pyrimidin-2-ylamino)-4-methoxyphenyl)acrylamide,
- N-(3-(4-(4-(azetidin-1-ylmethyl)-3-methyl-1H-pyrazol-1-yl)pyrimidin-2-ylamino)phenyl)acrylamide,
- N-(3-(4-(4-((3-hydroxyazetidin-1-yl)methyl)-3-methyl-1H-pyrazol-1-yl)pyrimidin-2-ylamino)phenyl)acrylamide,
- N-(3-(4-(4-((3-hydroxyazetidin-1-yl)methyl)-3-methyl-1H-pyrazol-1-yl)pyrimidin-2-ylamino)-5-methylphenyl)acrylamide,
- N-(5-(4-(4-((dimethylamino)methyl)-3-(4-fluorophenyl)-1H-pyrazol-1-yl)pyrimidin-2-ylamino)-4-methoxy-2-morpholinophenyl)acrylamide,
- N-(5-(4-(3-tert-butyl-4-((dimethylamino)methyl)-1H-pyrazol-1-yl)-5-methylpyrimidin-2-ylamino)-4-methoxy-2-morpholinophenyl)acrylamide,
- N-(3-(4-(4-((3-hydroxyazetidin-1-yl)methyl)-3-methyl-1H-pyrazol-1-yl)-5-methylpyrimidin-2-ylamino)-4-methoxyphenyl)acrylamide,
- N-(4-methoxy-3-(4-(3-methyl-1H-pyrazol-1-yl)pyrimidin-2-ylamino)phenyl)acrylamide,
- N-(3-(4-(4-((3-hydroxyazetidin-1-yl)methyl)-3-methyl-1H-pyrazol-1-yl)-5-methylpyrimidin-2-ylamino)-5-methylphenyl)acrylamide,
- N-(3-(4-(4-((3-hydroxyazetidin-1-yl)methyl)-1H-pyrazol-1-yl)-5-methylpyrimidin-2-ylamino)-4-methoxyphenyl)acrylamide,
- N-(5-(4-(4-(azetidin-1-ylmethyl)-3-methyl-1H-pyrazol-1-yl)pyrimidin-2-ylamino)-2-morpholinophenyl)acrylamide,
- N-(2-(4-acetylpiperazin-1-yl)-5-(4-(4-(azetidin-1-ylmethyl)-3-methyl-1H-pyrazol-1-yl)pyrimidin-2-ylamino)phenyl)acrylamide,
- N-(5-(4-(4-(azetidin-1-ylmethyl)-3-methyl-1H-pyrazol-1-yl)pyrimidin-2-ylamino)-4-methoxy-2-morpholinophenyl)acrylamide,
- N-(5-(4-(4-((3-hydroxyazetidin-1-yl)methyl)-3-methyl-1H-pyrazol-1-yl)pyrimidin-2-ylamino)-4-methoxy-2-morpholinophenyl)acrylamide,
- N-(5-(4-(4-(azetidin-1-ylmethyl)-3-methyl-1H-pyrazol-1-yl)pyrimidin-2-ylamino)-2-((2-(dimethylamino)ethyl)(methyl)amino)-4-methoxyphenyl)acrylamide,
- N-(5-(4-(4-(azetidin-1-ylmethyl)-3-methyl-1H-pyrazol-1-yl)pyrimidin-2-ylamino)-4-methoxy-2-(4-methylpiperazin-1-yl)phenyl)acrylamide,
- N-(5-(4-(4-(azetidin-1-ylmethyl)-3-methyl-1H-pyrazol-1-yl)pyrimidin-2-ylamino)-4-methoxy-2-(piperidin-1-yl)phenyl)acrylamide,
- N-(5-(4-(4-((3-hydroxyazetidin-1-yl)methyl)-1H-pyrazol-1-yl)-5-methylpyrimidin-2-ylamino)-4-methoxy-2-morpholinophenyl)acrylamide,
- N-(5-(4-(4-(((3R,4S)-3,4-dihydroxypyrrolidin-1-yl)methyl)-1H-pyrazol-1-yl)-5-methylpyrimidin-2-ylamino)-4-methoxy-2-morpholinophenyl)acrylamide,
- N-(5-(4-(4-(((3S,4R)-3-hydroxy-4-methoxypyrrolidin-1-yl)methyl)-1H-pyrazol-1-yl)-5-methylpyrimidin-2-ylamino)-4-methoxy-2-morpholinophenyl)acrylamide,
- N-(5-(4-(4-((dimethylamino)methyl)-1H-pyrazol-1-yl)-5-methylpyrimidin-2-ylamino)-4-methoxy-2-morpholinophenyl)acrylamide,
- N-(4-methoxy-5-(5-methyl-4-(4-((methyl(1-methylazetidin-3-yl)amino)methyl)-1H-pyrazol-1-yl)pyrimidin-2-ylamino)-2-morpholinophenyl)acrylamide,
- N-(5-(4-(4-((3-hydroxyazetidin-1-yl)methyl)-3-methyl-1H-pyrazol-1-yl)-5-methylpyrimidin-2-ylamino)-4-methoxy-2-morpholinophenyl)acrylamide,
- N-(5-(4-(4-(((3R,4S)-3,4-dihydroxypyrrolidin-1-yl)methyl)-3-methyl-1H-pyrazol-1-yl)-5-methylpyrimidin-2-ylamino)-4-methoxy-2-morpholinophenyl)acrylamide,
- N-(5-(4-(4-(((3S,4R)-3-hydroxy-4-methoxypyrrolidin-1-yl)methyl)-3-methyl-1H-pyrazol-1-yl)-5-methylpyrimidin-2-ylamino)-4-methoxy-2-morpholinophenyl)acrylamide,
- (R)—N-(5-(4-(4-((3-hydroxypyrrolidin-1-yl)methyl)-3-methyl-1H-pyrazol-1-yl)-5-methylpyrimidin-2-ylamino)-4-methoxy-2-morpholinophenyl)acrylamide,
- (S)—N-(5-(4-(4-((3-hydroxypyrrolidin-1-yl)methyl)-3-methyl-1H-pyrazol-1-yl)-5-methylpyrimidin-2-ylamino)-4-methoxy-2-morpholinophenyl)acrylamide,
- N-(5-(4-(4-((3-hydroxyazetidin-1-yl)methyl)-3-methyl-1H-pyrazol-1-yl)-5-methylpyrimidin-2-ylamino)-4-methoxy-2-(4-methylpiperazin-1-yl)phenyl)acrylamide,
- N-(5-(4-(4-((3-hydroxyazetidin-1-yl)methyl)-3-methyl-1H-pyrazol-1-yl)-5-methylpyrimidin-2-ylamino)-4-methoxy-2-(piperidin-1-yl)phenyl)acrylamide,
- N-(2-((2-(dimethylamino)ethyl)(methyl)amino)-5-(4-(4-((3-hydroxyazetidin-1-yl)methyl)-3-methyl-1H-pyrazol-1-yl)-5-methylpyrimidin-2-ylamino)-4-methoxyphenyl)acrylamide,
- N-(5-(4-(4-(azetidin-1-ylmethyl)-1H-pyrazol-1-yl)-5-methylpyrimidin-2-ylamino)-4-methoxy-2-morpholinophenyl)acrylamide,
- N-(4-methoxy-5-(5-methyl-4-(4-(morpholinomethyl)-1H-pyrazol-1-yl)pyrimidin-2-ylamino)-2-(4-methylpiperazin-1-yl)phenyl)acrylamide,
- N-(5-(4-(4-(azetidin-1-ylmethyl)-1H-pyrazol-1-yl)pyrimidin-2-ylamino)-4-methoxy-2-morpholinophenyl)acrylamide,
- (S)—N-(5-(4-(4-((3-(dimethylamino)pyrrolidin-1-yl)methyl)-1H-pyrazol-1-yl)pyrimidin-2-ylamino)-4-methoxy-2-morpholinophenyl)acrylamide,
- N-(5-(4-(4-(azetidin-1-ylmethyl)-1H-pyrazol-1-yl)-5-methylpyrimidin-2-ylamino)-4-methoxy-2-(4-methylpiperazin-1-yl)phenyl)acrylamide, N-(2-(4-acetylpiperazin-1-yl)-5-(4-(4-(azetidin-1-ylmethyl)-1H-pyrazol-1-yl)-5-methylpyrimidin-2-ylamino)-4-methoxyphenyl)acrylamide,
N-(5-(4-(4-(azetidin-1-ylmethyl)-1H-pyrazol-1-yl)pyrimidin-2-ylamino)-2-(dimethylamino)-4-methoxyphenyl)acrylamide,
(R)—N-(5-(4-(4-(((3-(dimethylamino)pyrrolidin-1-yl)methyl)-1H-pyrazol-1-yl)pyrimidin-2-ylamino)-4-methoxy-2-morpholinophenyl)acrylamide,
N-(5-(4-(4-(azetidin-1-ylmethyl)-1H-pyrazol-1-yl)-5-methylpyrimidin-2-ylamino)-4-methoxy-2-(1,4-oxazepan-4-yl)phenyl)acrylamide,
N-(5-(4-(4-(azetidin-1-ylmethyl)-1H-pyrazol-1-yl)-5-methylpyrimidin-2-ylamino)-4-methoxy-2-(4-methyl-1,4-diazepan-1-yl)phenyl)acrylamide,
N-(5-(4-(4-(azetidin-1-ylmethyl)-1H-pyrazol-1-yl)-5-methylpyrimidin-2-ylamino)-2-((2-(dimethylamino)ethyl)(methyl)amino)-4-methoxyphenyl)acrylamide,
N-(2-((2-(dimethylamino)ethyl)(methyl)amino)-5-(4-(4-(((3S,4R)-3-hydroxy-4-methoxypyrrolidin-1-yl)methyl)-1H-pyrazol-1-yl)-5-methylpyrimidin-2-ylamino)-4-methoxyphenyl)acrylamide,
N-(4-methoxy-5-(4-(4-((3-methoxyazetidin-1-yl)methyl)-3-methyl-1H-pyrazol-1-yl)pyrimidin-2-ylamino)-2-morpholinophenyl)acrylamide,
N-(5-(4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide,
N-(5-(4-(4-((dimethylamino)methyl)-3-methyl-1H-pyrazol-1-yl)pyrimidin-2-ylamino)-4-methoxy-2-morpholinophenyl)acrylamide,
N-(5-(4-(4-((dimethylamino)methyl)-3-methyl-1H-pyrazol-1-yl)pyrimidin-2-ylamino)-4-methoxy-2-(4-methylpiperazin-1-yl)phenyl)acrylamide,
N-(5-(4-(3-((3-hydroxyazetidin-1-yl)methyl)-4-methyl-1H-pyrrol-1-yl)-5-methylpyrimidin-2-ylamino)-4-methoxy-2-morpholinophenyl)acrylamide,
N-(5-(5-chloro-4-(4-((3-hydroxyazetidin-1-yl)methyl)-3-methyl-1H-pyrazol-1-yl)pyrimidin-2-ylamino)-4-methoxy-2-morpholinophenyl)acrylamide,
N-(5-(4-(4-(azetidin-1-ylmethyl)-3-methyl-1H-pyrazol-1-yl)-5-chloropyrimidin-2-ylamino)-4-methoxy-2-morpholinophenyl)acrylamide,
N-(5-(5-chloro-4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide,
N-(5-(5-chloro-4-(4-((dimethylamino)methyl)-3-methyl-1H-pyrazol-1-yl)pyrimidin-2-ylamino)-4-methoxy-2-morpholinophenyl)acrylamide,
N-(5-(4-(4-(azetidin-1-ylmethyl)-3-methyl-1H-pyrazol-1-yl)pyrimidin-2-ylamino)-4-methoxy-2-(1H-pyrazol-1-yl)phenyl)acrylamide,
N-(5-(5-chloro-4-(4-(((3R,4S)-3,4-dihydroxypyrrolidin-1-yl)methyl)-3-methyl-1H-pyrazol-1-yl)pyrimidin-2-ylamino)-4-methoxy-2-(4-methylpiperazin-1-yl)phenyl)acrylamide,
N-(5-(4-(4-(azetidin-1-ylmethyl)-3-cyclopropyl-1H-pyrazol-1-yl)pyrimidin-2-ylamino)-4-methoxy-2-morpholinophenyl)acrylamide,
N-(5-(4-(3-cyclopropyl-4-(((3S,4R)-3-hydroxy-4-methoxypyrrolidin-1-yl)methyl)-1H-pyrazol-1-yl)pyrimidin-2-ylamino)-4-methoxy-2-morpholinophenyl)acrylamide,
N-(3-(4-(4-((3-hydroxyazetidin-1-yl)methyl)-3-methyl-1H-pyrazol-1-yl)pyrimidin-2-ylamino)-5-(1-methyl-1H-pyrazol-4-yl)phenyl)acrylamide,
N-(5-(4-(4-((3-hydroxyazetidin-1-yl)methyl)-3-methyl-1H-pyrazol-1-yl)pyrimidin-2-ylamino)-4-methoxy-2-(1-methyl-1H-pyrazol-4-yl)phenyl)acrylamide,
N-(5-(4-(4-(azetidin-1-ylmethyl)-1H-pyrazol-1-yl)pyrimidin-2-ylamino)-4-methoxy-2-(1-methyl-1,2,3,6-tetrahydropyridin-4-yl)phenyl)acrylamide,
N-(5-(4-(3-(azetidin-1-ylmethyl)-4-methyl-1H-pyrrol-1-yl)-5-fluoropyrimidin-2-ylamino)-4-methoxy-2-morpholinophenyl)acrylamide,
N-(5-(5-fluoro-4-(4-(((3S,4R)-3-hydroxy-4-methoxypyrrolidin-1-yl)methyl)-3-methyl-1H-pyrazol-1-yl)pyrimidin-2-ylamino)-4-methoxy-2-morpholinophenyl)acrylamide,
N-(5-(4-(4-(azetidin-1-ylmethyl)-3-methyl-1H-pyrazol-1-yl)-5-fluoropyrimidin-2-ylamino)-4-methoxy-2-morpholinophenyl)acrylamide,
N-(5-(4-(4-(azetidin-1-ylmethyl)-1H-pyrazol-1-yl)-5-methylpyrimidin-2-ylamino)-4-isopropoxy-2-morpholinophenyl)acrylamide,
N-(5-(4-(4-(azetidin-1-ylmethyl)-1H-pyrazol-1-yl)-5-methylpyrimidin-2-ylamino)-4-methoxy-2-(1-methyl-1,2,3,6-tetrahydropyridin-4-yl)phenyl)acrylamide,
N-(4-(4-(4-(azetidin-1-ylmethyl)-3-methyl-1H-pyrazol-1-yl)pyrimidin-2-ylamino)-5-methoxybiphenyl-2-yl)acrylamide,
N-(5-(4-(4-(hydroxymethyl)-3-methyl-1H-pyrazol-1-yl)pyrimidin-2-ylamino)-4-methoxy-2-morpholinophenyl)acrylamide,
N-(5-(4-(4-(azetidin-1-ylmethyl)-3-tert-butyl-1H-pyrazol-1-yl)-5-methylpyrimidin-2-ylamino)-4-methoxy-2-morpholinophenyl)acrylamide,
N-(4-(4-(4-(azetidin-1-ylmethyl)-3-methyl-1H-pyrazol-1-yl)pyrimidin-2-ylamino)-2',5-dimethoxybiphenyl-2-yl)acrylamide,
N-(5-(4-(4-(azetidin-1-ylmethyl)-3-methyl-1H-pyrazol-1-yl)pyrimidin-2-ylamino)-2-(4,4-difluoropiperidin-1-yl)-4-methoxyphenyl)acrylamide,
N-(5-(4-(4-(azetidin-1-ylmethyl)-3,5-dimethyl-1H-pyrazol-1-yl)pyrimidin-2-ylamino)-4-methoxy-2-morpholinophenyl)acrylamide,
N-(2-(dimethylamino)-5-(4-(4-((dimethylamino)methyl)-3-methyl-1H-pyrazol-1-yl)pyrimidin-2-ylamino)-4-methoxyphenyl)acrylamide,
N-(5-(4-(4-((3-fluoroazetidin-1-yl)methyl)-3-methyl-1H-pyrazol-1-yl)pyrimidin-2-ylamino)-4-methoxy-2-morpholinophenyl)acrylamide,
N-(5-(4-(4-((dimethylamino)methyl)-3-phenyl-1H-pyrazol-1-yl)pyrimidin-2-ylamino)-4-methoxy-2-morpholinophenyl)acrylamide,
N-(5-(4-(3-cyclopropyl-4-((dimethylamino)methyl)-1H-pyrazol-1-yl)pyrimidin-2-ylamino)-4-methoxy-2-morpholinophenyl)acrylamide,
N-(5-(4-(4-((dimethylamino)methyl)-3-methyl-1H-pyrazol-1-yl)-5-methylpyrimidin-2-ylamino)-4-methoxy-2-morpholinophenyl)acrylamide,
N-(5-(4-(4-(azetidin-1-ylmethyl)-3-methyl-1H-pyrazol-1-yl)-5-methylpyrimidin-2-ylamino)-4-methoxy-2-morpholinophenyl)acrylamide,
N-(5-(5-chloro-4-(4-((dimethylamino)methyl)-1H-pyrazol-1-yl)pyrimidin-2-ylamino)-4-methoxy-2-morpholinophenyl)acrylamide,
N-(5-(4-(4-(azetidin-1-ylmethyl)-3-phenyl-1H-pyrazol-1-yl)pyrimidin-2-ylamino)-4-methoxy-2-morpholinophenyl)acrylamide,
N-(5-(4-(4-((dimethylamino)methyl)-3-methyl-1H-pyrazol-1-yl)pyrimidin-2-ylamino)-2-(4-(2-fluoroethyl)piperazin-1-yl)-4-methoxyphenyl)acrylamide, N-(5-(4-(4-((dimethylamino)methyl)-3-p-tolyl-1H-pyrazol-1-yl)pyrimidin-2-ylamino)-4-methoxy-2-morpholinophenyl)acrylamide, N-(5-(4-(4-(azetidin-1-ylmethyl)-3-(4-fluorophenyl)-1H-pyrazol-1-yl)pyrimidin-2-ylamino)-4-methoxy-2-morpholinophenyl)acrylamide, N-(5-(4-(4-(azetidin-1-ylmethyl)-3-p-tolyl-1H-pyrazol-1-yl)pyrimidin-2-ylamino)-4-methoxy-2-morpholinophenyl)acrylamide, N-(2-(dimethylamino)-5-(4-(4-((dimethylamino)methyl)-3-phenyl-1H-pyrazol-1-yl)pyrimidin-2-ylamino)-4-methoxyphenyl)acrylamide, N-(2-(azetidin-1-yl)-5-(4-(4-((dimethylamino)methyl)-3-phenyl-1H-pyrazol-1-yl)pyrimidin-2-ylamino)-4-methoxyphenyl)acrylamide, N-(4-methoxy-2-(4-methylpiperazin-1-yl)-5-(4-(3-phenyl-1H-pyrazol-1-yl)pyrimidin-2-ylamino)phenyl)acrylamide, N-(5-(4-(3-tert-butyl-4-((dimethylamino)methyl)-1H-pyrazol-1-yl)pyrimidin-2-ylamino)-4-methoxy-2-morpholinophenyl)acrylamide, N-(2-(azetidin-1-yl)-5-(4-(4-(azetidin-1-ylmethyl)-3-phenyl-1H-pyrazol-1-yl)pyrimidin-2-ylamino)-4-methoxyphenyl)acrylamide, N-(5-(4-(4-((dimethylamino)methyl)-3-(thiophen-2-yl)-1H-pyrazol-1-yl)pyrimidin-2-ylamino)-4-methoxy-2-morpholinophenyl)acrylamide, N-(5-(4-(4-((dimethylamino)methyl)-3-(2,5-dimethylphenyl)-1H-pyrazol-1-yl)pyrimidin-2-ylamino)-4-methoxy-2-morpholinophenyl)acrylamide, N-(4-methoxy-2-morpholino-5-(4-(3-phenyl-4-(pyrrolidin-1-ylmethyl)-1H-pyrazol-1-yl)pyrimidin-2-ylamino)phenyl)acrylamide, N-(5-(4-(4-(hydroxymethyl)-3-phenyl-1H-pyrazol-1-yl)pyrimidin-2-ylamino)-4-methoxy-2-morpholinophenyl)acrylamide, N-(5-(4-(4-((ethyl(methyl)amino)methyl)-3-phenyl-1H-pyrazol-1-yl)pyrimidin-2-ylamino)-4-methoxy-2-morpholinophenyl)acrylamide, N-(5-(4-(4-((dimethylamino)methyl)-3-isopropyl-1H-pyrazol-1-yl)pyrimidin-2-ylamino)-4-methoxy-2-morpholinophenyl)acrylamide, N-(5-(4-(4-((dimethylamino)methyl)-3-phenyl-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-phenyl-1H-pyrazol-1-yl)pyrimidin-2-ylamino)-4-methoxy-2-((2-methoxyethyl)(methyl)amino)phenyl)acrylamide, N-(5-(4-(4-((dimethylamino)methyl)-3-phenyl-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-phenyl-1H-pyrazol-1-yl)pyrimidin-2-ylamino)-4-methoxy-2-(methyl(oxetan-3-yl)amino)phenyl)acrylamide, N-(5-(4-(4-((dimethylamino)methyl)-3-phenyl-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-phenyl-1H-pyrazol-1-yl)pyrimidin-2-ylamino)-4-methoxy-2-(pyrrolidin-1-yl)phenyl)acrylamide, N-(5-(4-(3-tert-butyl-4-((dimethylamino)methyl)-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-tert-butyl-1H-pyrazol-1-yl)pyrimidin-2-ylamino)-4-methoxy-2-((2-methoxyethyl)(methyl)amino)phenyl)acrylamide, N-(5-(4-(3-tert-butyl-4-((dimethylamino)methyl)-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-tert-butyl-1H-pyrazol-1-yl)pyrimidin-2-ylamino)-4-methoxy-2-(methyl(oxetan-3-yl)amino)phenyl)acrylamide, N-(5-(4-(3-tert-butyl-4-((dimethylamino)methyl)-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-tert-butyl-1H-pyrazol-1-yl)pyrimidin-2-ylamino)-4-methoxy-2-(pyrrolidin-1-yl)phenyl)acrylamide, N-(5-(4-(3-cyclopropyl-4-((dimethylamino)methyl)-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-cyclopropyl-1H-pyrazol-1-yl)pyrimidin-2-ylamino)-4-methoxy-2-((2-methoxyethyl)(methyl)amino)phenyl)acrylamide, N-(5-(4-(3-cyclopropyl-4-((dimethylamino)methyl)-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-cyclopropyl-1H-pyrazol-1-yl)pyrimidin-2-ylamino)-4-methoxy-2-(methyl(oxetan-3-yl)amino)phenyl)acrylamide, N-(5-(4-(3-cyclopropyl-4-((dimethylamino)methyl)-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-cyclopropyl-1H-pyrazol-1-yl)pyrimidin-2-ylamino)-4-methoxy-2-(pyrrolidin-1-yl)phenyl)acrylamide, N-(5-(4-(4-((dimethylamino)methyl)-3-isopropyl-1H-pyrazol-1-yl)pyrimidin-2-ylamino)-4-methoxy-2-((2-methoxyethyl)(methyl)amino)phenyl)acrylamide, N-(5-(4-(4-(azetidin-1-ylmethyl)-3-isopropyl-1H-pyrazol-1-yl)pyrimidin-2-ylamino)-4-methoxy-2-((2-methoxyethyl)(methyl)amino)phenyl)acrylamide, N-(5-(4-(4-((dimethylamino)methyl)-3-isopropyl-1H-pyrazol-1-yl)pyrimidin-2-ylamino)-4-methoxy-2-(methyl(oxetan-3-yl)amino)phenyl)acrylamide, N-(5-(4-(4-(azetidin-1-ylmethyl)-3-isopropyl-1H-pyrazol-1-yl)pyrimidin-2-ylamino)-4-methoxy-2-(methyl(oxetan-3-yl)amino)phenyl)acrylamide, N-(5-(4-(4-((dimethylamino)methyl)-3-isopropyl-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-isopropyl-1H-pyrazol-1-yl)pyrimidin-2-ylamino)-4-methoxy-2-(pyrrolidin-1-yl)phenyl)acrylamide, N-(5-(4-(4-(azetidin-1-ylmethyl)-3-(thiophen-2-yl)-1H-pyrazol-1-yl)pyrimidin-2-ylamino)-4-methoxy-2-morpholinophenyl)acrylamide, N-(5-(4-(4-(azetidin-1-ylmethyl)-3-isopropyl-1H-pyrazol-1-yl)pyrimidin-2-ylamino)-4-methoxy-2-morpholinophenyl)acrylamide, N-(5-(4-(4-((dimethylamino)methyl)-3-phenyl-1H-pyrazol-1-yl)-5-methylpyrimidin-2-ylamino)-4-methoxy-2-morpholinophenyl)acrylamide, N-(5-(4-(4-(azetidin-1-ylmethyl)-3-phenyl-1H-pyrazol-1-yl)-5-methylpyrimidin-2-ylamino)-4-methoxy-2-morpholinophenyl)acrylamide, N-(5-(4-(3-cyclopropyl-4-((dimethylamino)methyl)-1H-pyrazol-1-yl)-5-methylpyrimidin-2-ylamino)-4-methoxy-2-morpholinophenyl)acrylamide, N-(5-(4-(4-(azetidin-1-ylmethyl)-3-cyclopropyl-1H-pyrazol-1-yl)-5-methylpyrimidin-2-ylamino)-4-methoxy-2-morpholinophenyl)acrylamide, N-(5-(4-(4-((dimethylamino)methyl)-3-isopropyl-1H-pyrazol-1-yl)-5-methylpyrimidin-2-ylamino)-4-methoxy-2-morpholinophenyl)acrylamide, N-(5-(4-(4-(azetidin-1-ylmethyl)-3-isopropyl-1H-pyrazol-1-yl)-5-methylpyrimidin-2-ylamino)-4-methoxy-2-morpholinophenyl)acrylamide, N-(5-(4-(3-tert-butyl-4-((dimethylamino)methyl)-1H-pyrazol-1-yl)pyrimidin-2-ylamino)-2-(ethyl(2-methoxyethyl)amino)-4-methoxyphenyl)acrylamide, N-(5-(4-(4-((dimethylamino)methyl)-3-(furan-3-yl)-1H-pyrazol-1-yl)pyrimidin-2-ylamino)-4-methoxy-2-morpholinophenyl)acrylamide, N-(5-(4-(4-((dimethylamino)methyl)-3-(pyridin-3-yl)-1H-pyrazol-1-yl)pyrimidin-2-ylamino)-4-methoxy-2-morpholinophenyl)acrylamide, N-(2-(4-acetylpiperazin-1-yl)-5-(4-(3-cyclopropyl-4-((dimethylamino)methyl)-1H-pyrazol-1-yl)pyrimidin-2-ylamino)-4-methoxyphenyl)acrylamide, N-(5-(4-(3-(azetidin-1-ylmethyl)-4-(furan-3-yl)-1H-pyrrol-1-yl)-5-fluoropyrimidin-2-ylamino)-4-methoxy-2-morpholinophenyl)acrylamide, N-(5-(4-(3-((dimethylamino)methyl)-4-(furan-3-yl)-1H-pyrrol-1-yl)-5-fluoropyrimidin-2-ylamino)-4-methoxy-2-morpholinophenyl)acrylamide, N-(5-(4-(3-cyclopropyl-4-((dimethylamino)methyl)-1H-pyrazol-1-yl)-5-methylpyrimidin-2-ylamino)-4-methoxy-2-(methyl(oxetan-3-yl)amino)phenyl)acrylamide, N-(2-(4-acetylpiperazin-1-yl)-5-(4-(4-(azetidin-1-ylmethyl)-3-phenyl-1H-pyrazol-1-yl)pyrimidin-2-ylamino)-4-methoxyphenyl)acrylamide, N-(2-(4-acetylpiperazin-1-yl)-5-(4-(4-((dimethylamino)methyl)-3-phenyl-1H-pyrazol-1-yl)pyrimidin-2-ylamino)-4-methoxyphenyl)acrylamide, N-(5-(4-(4-((dimethylamino)methyl)-3-(pyridin-4-yl)-1H-pyrazol-1-yl)pyrimidin-2-ylamino)-4-methoxy-2-morpholinophenyl)acrylamide, N-(2-(4-acetylpiperazin-1-yl)-5-(4-(3-cyclopropyl-4-((ethyl(methyl)amino)methyl)-1H-pyrazol-1-yl)pyrimidin-2-ylamino)-4-methoxyphenyl)acrylamide, N-(2-(4-acetylpiperazin-1-yl)-5-(4-(4-(azetidin-1-ylmethyl)-3-cyclopropyl-1H-pyrazol-1-yl)pyrimidin-2-ylamino)-4-methoxyphenyl)acrylamide, N-(2-(azetidin-1-yl)-5-(4-(4-(azetidin-1-ylmethyl)-3-cyclopropyl-1H-pyrazol-1-yl)pyrimidin-2-ylamino)-4-methoxyphenyl)acrylamide, N-(5-(4-(3-cyclopropyl-4-((ethyl(methyl)amino)methyl)-1H-pyrazol-1-yl)pyrimidin-2-ylamino)-4-methoxy-2-morpholinophenyl)acrylamide, N-(2-(azetidin-1-yl)-5-(4-(3-(azetidin-1-ylmethyl)-4-methyl-1H-pyrrol-1-yl)-5-fluoropyrimidin-2-ylamino)-4-methoxyphenyl)acrylamide, N-(5-(4-(3-(azetidin-1-ylmethyl)-4-methyl-1H-pyrrol-1-yl)-5-fluoropyrimidin-2-ylamino)-2-(dimethylamino)-4-methoxyphenyl)acrylamide, N-(2-(dimethylamino)-5-(4-(3-((dimethylamino)methyl)-4-methyl-1H-pyrrol-1-yl)-5-fluoropyrimidin-2-ylamino)-4-methoxyphenyl)acrylamide, N-(2-((2-(dimethylamino)ethyl)(methyl)amino)-5-(4-(3-((dimethylamino)methyl)-4-(trifluoromethyl)-1H-pyrrol-1-yl)-5-fluoropyrimidin-2-ylamino)-4-methoxyphenyl)acrylamide, N-(5-(4-(4-((ethyl(methyl)amino)methyl)-3-methyl-1H-pyrazol-1-yl)pyrimidin-2-ylamino)-4-methoxy-2-morpholinophenyl)acrylamide, or a pharmaceutically acceptable salt thereof.

14. A method of treating cancer, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, atherosclerosis, restenosis, asthma, transplantation rejection, inflammation, thrombosis, inflammatory bowel disease, Crohn's disease, ulcerative colitis, lupus, chronic pancreatitis, Alzheimer's disease, and Parkinson's disease, in a subject in need thereof, comprising administering to said subject a therapeutically effective amount of a compound of claim 1 or a pharmaceutically acceptable salt thereof.

15. A method of inhibiting at least one mutant of EGFR selectively as compared to wild type EGFR, in biological sample comprising contacting the biological sample with a compound according to claim 1, or a composition thereof.

16. The method according to claim 15, wherein the at least one mutant is Del E746-A750, L858R or T790M.

17. The method according to claim 15, wherein the at least one mutant is at least one double mutant selected from Del E746-A750/T790M or L858R/T790M.

18. A pharmaceutical composition comprising a compound of claim 1 together with a pharmaceutically acceptable carrier, diluent or excipient.

19. The method of claim 14 wherein the cancer is selected from the group consisting of infantile hemangiomas, non-small cell lung, bladder and head and neck cancers, prostate cancer, breast cancer, ovarian cancer, gastric and pancreatic cancer.

20. The method of claim 14 wherein the transplant rejection is bone marrow transplant rejection.

* * * * *